(12) United States Patent
Kircher et al.

(10) Patent No.: US 10,919,089 B2
(45) Date of Patent: Feb. 16, 2021

(54) ANISOTROPIC PARTICLES, METHODS AND USES THEREOF

(71) Applicant: Memorial Sloan Kettering Cancer Center, New York, NY (US)

(72) Inventors: Moritz Kircher, New York, NY (US); Matthew Wall, New York, NY (US); Stefan Harmsen, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 0 days.

(21) Appl. No.: 15/737,553

(22) PCT Filed: Jun. 30, 2016

(86) PCT No.: PCT/US2016/040250
§ 371 (c)(1),
(2) Date: Dec. 18, 2017

(87) PCT Pub. No.: WO2017/004301
PCT Pub. Date: Jan. 5, 2017

(65) Prior Publication Data
US 2018/0193910 A1    Jul. 12, 2018

Related U.S. Application Data

(60) Provisional application No. 62/187,703, filed on Jul. 1, 2015.

(51) Int. Cl.
*B22F 9/24* (2006.01)
*B22F 1/00* (2006.01)
(Continued)

(52) U.S. Cl.
CPC .......... *B22F 1/0018* (2013.01); *A61K 9/0009* (2013.01); *A61K 9/5115* (2013.01);
(Continued)

(58) Field of Classification Search
None
See application file for complete search history.

(56) References Cited

U.S. PATENT DOCUMENTS 4,127,329 A    11/1978    Chang et al.
4,604,992 A    8/1986    Sato
(Continued)

FOREIGN PATENT DOCUMENTS

CN    101679022 A    3/2010
CN    102015020 A    4/2011
(Continued)

OTHER PUBLICATIONS

English Translation of CN 104551012 (originally published Apr. 2015) from Espacenet.*
(Continued)

*Primary Examiner* — George Wyszomierski
(74) *Attorney, Agent, or Firm* — Wolf, Greenfield & Sacks, P.C.

(57) ABSTRACT

The present disclosure, among other things, provides new technologies for preparation of anisotropic nanoparticle cores (e.g., anisotropic gold nanoparticle cores) and compositions thereof. Provided technologies show a number of advantages as compared with previously available options for preparing anisotropic nanoparticle cores, including, for example, that they typically utilize mild reaction conditions and, in many embodiments, only environmentally benign agents. The present invention therefore provides "green" nanoparticle technologies. Surprisingly, in many cases, the same set of reactants can be used, under modestly different conditions, to generate nanoparticle cores of different shapes. The present invention provides selection rules for reaction conditions that generate populations containing particular shapes of interest.

20 Claims, 62 Drawing Sheets

(51) Int. Cl.
  *A61K 9/51* (2006.01)
  *A61K 9/00* (2006.01)
  *B82Y 30/00* (2011.01)

(52) U.S. Cl.
  CPC .............. *B22F 9/24* (2013.01); *A61K 9/5192* (2013.01); *B22F 2001/0037* (2013.01); *B22F 2301/255* (2013.01); *B22F 2998/10* (2013.01); *B22F 2999/00* (2013.01); *B82Y 30/00* (2013.01)

(56) References Cited

U.S. PATENT DOCUMENTS

| | | |
|---|---|---|
| 4,669,467 A | 6/1987 | Willet et al. |
| 4,938,205 A | 7/1990 | Nudelman |
| 5,275,594 A | 1/1994 | Baker et al. |
| 5,293,872 A | 3/1994 | Alfano et al. |
| 5,300,097 A | 4/1994 | Lemer et al. |
| 5,306,403 A | 4/1994 | Vo-Dinh |
| 5,491,510 A | 2/1996 | Gove |
| 5,594,497 A | 1/1997 | Ahern et al. |
| 5,609,907 A | 3/1997 | Natan |
| 5,713,364 A | 2/1998 | DeBaryshe et al. |
| 5,721,102 A | 2/1998 | Vo-Dinh |
| 5,813,987 A | 9/1998 | Modell et al. |
| 5,949,388 A | 9/1999 | Atsumi et al. |
| 6,002,471 A | 12/1999 | Quake |
| 6,006,126 A | 12/1999 | Cosman |
| 6,008,889 A | 12/1999 | Zeng et al. |
| 6,019,719 A | 2/2000 | Schulz et al. |
| 6,025,202 A | 2/2000 | Natan |
| 6,127,120 A | 10/2000 | Graham et al. |
| 6,174,291 B1 | 1/2001 | McMahon et al. |
| 6,174,677 B1 | 1/2001 | Vo-Dinh |
| 6,219,137 B1 | 4/2001 | Vo-Dinh |
| 6,228,076 B1 | 5/2001 | Winston et al. |
| 6,242,264 B1 | 6/2001 | Natan et al. |
| 6,251,127 B1 | 6/2001 | Biel |
| 6,254,852 B1 | 7/2001 | Glajch et al. |
| 6,514,767 B1 | 2/2003 | Natan |
| 6,579,726 B1 | 6/2003 | Natan et al. |
| 6,624,886 B2 | 9/2003 | Natan et al. |
| 6,640,130 B1 | 10/2003 | Freeman et al. |
| 6,788,860 B1 | 9/2004 | Treado et al. |
| 6,959,024 B2 | 10/2005 | Paldus et al. |
| 7,076,092 B2 | 7/2006 | Hollars et al. |
| 7,192,778 B2 | 3/2007 | Natan |
| 7,443,489 B2 | 10/2008 | Natan |
| 7,538,859 B2 | 5/2009 | Tearney et al. |
| 7,656,525 B2 | 2/2010 | Zhao et al. |
| 7,738,096 B2 | 6/2010 | Zhao et al. |
| 7,760,352 B2 | 7/2010 | Armstrong et al. |
| 7,826,176 B2 | 11/2010 | Shirotori et al. |
| 7,829,140 B1 | 11/2010 | Zhong et al. |
| 8,054,463 B2 | 11/2011 | Morris et al. |
| 8,320,650 B2 | 11/2012 | Demos et al. |
| 8,409,862 B2 | 4/2013 | Caulfield et al. |
| 8,409,863 B2 | 4/2013 | Natan et al. |
| 8,416,405 B2 | 4/2013 | Panza et al. |
| 8,497,131 B2 | 7/2013 | Natan et al. |
| 8,568,878 B2 | 10/2013 | Wilson et al. |
| 8,771,978 B2 | 7/2014 | Ragan |
| 8,795,628 B2 | 8/2014 | Gambhir et al. |
| 8,918,161 B2 | 12/2014 | Natan et al. |
| 9,086,533 B1 | 7/2015 | Wach |
| 9,295,391 B1 | 3/2016 | Tearney et al. |
| 9,314,849 B2 | 4/2016 | Tracy et al. |
| 9,561,292 B1 | 2/2017 | Vo-Dinh et al. |
| 9,789,154 B1* | 10/2017 | Vo-Dinh ............... A61K 38/02 |
| 9,833,144 B2 | 12/2017 | Kircher et al. |
| 10,105,456 B2 | 10/2018 | Harmsen et al. |
| 10,322,194 B2 | 6/2019 | Kircher et al. |
| 10,688,202 B2 | 6/2020 | Wall et al. |
| 2002/0045266 A1 | 4/2002 | Fenniri |
| 2002/0082498 A1 | 6/2002 | Wendt et al. |
| 2002/0163482 A1 | 11/2002 | Sullivan |
| 2002/0165594 A1 | 11/2002 | Biel |
| 2003/0055307 A1 | 3/2003 | Elmaleh et al. |
| 2003/0191379 A1 | 10/2003 | Benaron et al. |
| 2003/0201208 A1 | 10/2003 | Koch et al. |
| 2004/0009341 A1 | 1/2004 | Naasani |
| 2004/0010192 A1 | 1/2004 | Benaron et al. |
| 2004/0073120 A1 | 4/2004 | Motz et al. |
| 2004/0225222 A1 | 11/2004 | Zeng et al. |
| 2004/0254419 A1 | 12/2004 | Wang et al. |
| 2004/0254454 A1 | 12/2004 | Kockro |
| 2005/0014851 A1 | 1/2005 | Bringley |
| 2005/0074779 A1 | 4/2005 | Vo-Dinh |
| 2005/0143662 A1 | 6/2005 | Marchitto et al. |
| 2005/0221494 A1 | 10/2005 | Natan |
| 2005/0272160 A1 | 12/2005 | Natan |
| 2005/0277816 A1 | 12/2005 | Maier et al. |
| 2006/0008924 A1 | 1/2006 | Anker et al. |
| 2006/0054506 A1 | 3/2006 | Natan et al. |
| 2006/0098194 A1 | 5/2006 | Tuschel |
| 2006/0173293 A1 | 8/2006 | Marquart et al. |
| 2006/0250613 A1 | 11/2006 | Demuth et al. |
| 2007/0010809 A1 | 1/2007 | Hovda et al. |
| 2007/0134805 A1 | 6/2007 | Gilbert |
| 2007/0167838 A1 | 7/2007 | Hubble et al. |
| 2007/0178067 A1 | 8/2007 | Maier et al. |
| 2007/0196281 A1 | 8/2007 | Jin et al. |
| 2007/0232874 A1 | 10/2007 | Ince |
| 2007/0238953 A1 | 10/2007 | Lucassen et al. |
| 2007/0255356 A1 | 11/2007 | Rose et al. |
| 2007/0260295 A1 | 11/2007 | Chen et al. |
| 2007/0269382 A1 | 11/2007 | Santra et al. |
| 2007/0282190 A1 | 12/2007 | Dekel et al. |
| 2007/0299550 A1 | 12/2007 | Nishijima et al. |
| 2008/0007716 A1 | 1/2008 | Igarashi |
| 2008/0058908 A1 | 3/2008 | Bornstein |
| 2008/0089839 A1 | 4/2008 | Lu et al. |
| 2008/0095852 A1 | 4/2008 | Kong |
| 2008/0118912 A1 | 5/2008 | Dickson et al. |
| 2008/0119832 A1 | 5/2008 | Cronin |
| 2008/0295646 A1 | 12/2008 | Mirkin et al. |
| 2008/0305045 A1 | 12/2008 | Kuniyil et al. |
| 2009/0137666 A1 | 5/2009 | Wang et al. |
| 2009/0171330 A1 | 7/2009 | Taylor et al. |
| 2009/0204111 A1 | 8/2009 | Bissig et al. |
| 2009/0218550 A1 | 9/2009 | Koyakutty et al. |
| 2009/0237648 A1 | 9/2009 | Armstrong et al. |
| 2009/0263485 A1 | 10/2009 | Li et al. |
| 2009/0281536 A1 | 11/2009 | Beckman et al. |
| 2009/0285766 A1 | 11/2009 | Kishen et al. |
| 2009/0294692 A1 | 12/2009 | Bourke, Jr. et al. |
| 2009/0304581 A1 | 12/2009 | Scheinberg et al. |
| 2010/0016783 A1 | 1/2010 | Bourke, Jr. et al. |
| 2010/0045778 A1 | 2/2010 | Yelin |
| 2010/0166650 A1 | 7/2010 | Gambhir |
| 2010/0197937 A1 | 8/2010 | Minami et al. |
| 2010/0211137 A1 | 8/2010 | Kim et al. |
| 2010/0233147 A1 | 9/2010 | Schwartz et al. |
| 2010/0255599 A1 | 10/2010 | Drake et al. |
| 2010/0279272 A1 | 11/2010 | Burrell et al. |
| 2010/0322471 A1 | 12/2010 | Treado et al. |
| 2011/0020239 A1 | 1/2011 | Suite et al. |
| 2011/0021970 A1 | 1/2011 | Vo-Dinh et al. |
| 2011/0045081 A1 | 2/2011 | Steitz et al. |
| 2011/0123439 A1 | 5/2011 | Cheon et al. |
| 2011/0152692 A1 | 6/2011 | Nie |
| 2011/0165077 A1 | 7/2011 | Qian et al. |
| 2011/0182881 A1 | 7/2011 | Chin et al. |
| 2011/0189483 A1* | 8/2011 | Zubarev ............... B82Y 30/00 428/402 |
| 2011/0190760 A1 | 8/2011 | Niver et al. |
| 2011/0207231 A1 | 8/2011 | Natan et al. |
| 2011/0230760 A1 | 9/2011 | Gambhir et al. |
| 2011/0242533 A1 | 10/2011 | Treado et al. |
| 2011/0261351 A1 | 10/2011 | Treado et al. |
| 2011/0262351 A1 | 10/2011 | Chung et al. |
| 2011/0263920 A1 | 10/2011 | Bourke, Jr. et al. |
| 2011/0282181 A1 | 11/2011 | Wang et al. |
| 2012/0123205 A1 | 5/2012 | Nie et al. |

(56) References Cited

U.S. PATENT DOCUMENTS

| | | | |
|---|---|---|---|
| 2012/0136241 A1 | 5/2012 | Chen et al. |
| 2012/0141380 A1 | 6/2012 | Margel et al. |
| 2012/0141981 A1 | 6/2012 | Pantazis et al. |
| 2012/0164624 A1 | 6/2012 | Natan et al. |
| 2012/0164680 A1 | 6/2012 | McNaughton et al. |
| 2012/0179029 A1 | 7/2012 | Kircher et al. |
| 2012/0212733 A1 | 8/2012 | Kodali et al. |
| 2012/0226139 A1 | 9/2012 | Peyman |
| 2012/0251450 A1 | 10/2012 | Punnoose et al. |
| 2012/0282632 A1 | 11/2012 | Chiu et al. |
| 2012/0283336 A1 | 11/2012 | Grigorenko et al. |
| 2012/0283379 A1 | 11/2012 | Auger et al. |
| 2012/0302940 A1 | 11/2012 | Ray |
| 2013/0012794 A1 | 1/2013 | Zeng et al. |
| 2013/0023770 A1 | 1/2013 | Courtney et al. |
| 2013/0029360 A1 | 1/2013 | Suh et al. |
| 2013/0040292 A1 | 2/2013 | Lopez et al. |
| 2013/0137944 A1 | 5/2013 | Jeong et al. |
| 2013/0164842 A1 | 6/2013 | Ujihara et al. |
| 2013/0231573 A1 | 9/2013 | Zena et al. |
| 2013/0309280 A1 | 11/2013 | Choi et al. |
| 2013/0330839 A1 | 12/2013 | Suh et al. |
| 2013/0342683 A1 | 12/2013 | Nelson et al. |
| 2014/0140594 A1 | 5/2014 | Mahadevan-Jansen et al. |
| 2014/0316255 A1 | 10/2014 | Garai et al. |
| 2014/0329089 A1 * | 11/2014 | Yin ........................ B82Y 30/00 428/390 |
| 2014/0350534 A1 | 11/2014 | Kircher et al. |
| 2015/0018807 A1 | 1/2015 | Kircher et al. |
| 2015/0125952 A1 | 5/2015 | Kim et al. |
| 2015/0182296 A1 | 7/2015 | Daon et al. |
| 2015/0258218 A1 | 9/2015 | Kircher et al. |
| 2015/0328346 A1 | 11/2015 | Harmsen et al. |
| 2016/0000329 A1 | 1/2016 | Kircher et al. |
| 2016/0000330 A1 | 1/2016 | Huang et al. |
| 2016/0018404 A1 | 1/2016 | Iyer et al. |
| 2016/0166194 A1 | 6/2016 | Gareau et al. |
| 2016/0367668 A1 | 12/2016 | Kircher et al. |
| 2017/0138860 A1 | 5/2017 | Huang |
| 2017/0266328 A1 | 9/2017 | Wall et al. |
| 2017/0296293 A1 | 10/2017 | Mak et al. |
| 2018/0271502 A1 | 9/2018 | Zarrine-Afsar |
| 2020/0230070 A1 | 7/2020 | Kircher et al. |

FOREIGN PATENT DOCUMENTS

| | | |
|---|---|---|
| CN | 102175655 A | 9/2011 |
| CN | 102410994 A | 4/2012 |
| CN | 102686181 A | 9/2012 |
| CN | 102770071 A | 11/2012 |
| CN | 102559190 B | 9/2013 |
| CN | 104551012 A * | 4/2015 |
| DE | 102 49 674 A1 | 5/2004 |
| DE | 102005030986 A1 | 1/2007 |
| DE | 10 2011 103 950 A1 | 12/2012 |
| EP | 2671613 A2 | 12/2013 |
| JP | H09-005666 A | 1/1997 |
| JP | H11-084307 A | 3/1999 |
| JP | 2002-534199 A | 9/2002 |
| JP | 2003-503135 A | 1/2003 |
| JP | 2004-193545 A | 7/2004 |
| JP | 2005-306827 A | 11/2005 |
| JP | 2009-011546 A | 1/2009 |
| JP | 2009-508571 A | 3/2009 |
| JP | 2009-511891 A | 3/2009 |
| JP | 2009-115546 A | 5/2009 |
| JP | 2009-222713 A | 10/2009 |
| JP | 2010-523983 A | 7/2010 |
| JP | 2011-158334 A | 8/2011 |
| TW | 572748 B | 1/2004 |
| WO | WO 1990/03803 A1 | 4/1990 |
| WO | WO 1993/03672 A1 | 3/1993 |
| WO | WO 2000/41611 A2 | 7/2000 |
| WO | WO 2001/01854 A2 | 1/2001 |
| WO | WO 2001/81923 A1 | 11/2001 |
| WO | WO 2002/100285 A1 | 12/2002 |
| WO | WO 2005/107623 A2 | 11/2005 |
| WO | WO 2008/122035 A1 | 10/2008 |
| WO | WO 2010/096828 A1 | 8/2010 |
| WO | WO 2010/111066 A2 | 9/2010 |
| WO | WO 2011/025640 A1 | 3/2011 |
| WO | WO 2011/084528 A1 | 7/2011 |
| WO | WO 2012/065163 A2 | 5/2012 |
| WO | WO 2012/070893 A2 | 5/2012 |
| WO | WO 2012/166796 A1 | 12/2012 |
| WO | WO-2013/128458 A1 * | 9/2013 |
| WO | WO 2014/036470 A1 | 3/2014 |
| WO | WO 2014/089247 A2 | 6/2014 |
| WO | WO 2014/100380 A2 | 6/2014 |
| WO | WO 2014/130736 A1 | 8/2014 |
| WO | WO 2015/134620 A1 | 9/2015 |
| WO | WO 2016/018896 A1 | 2/2016 |
| WO | WO 2016/028749 A1 | 2/2016 |
| WO | WO 2016/149378 A1 | 9/2016 |
| WO | WO 2016/179260 A1 | 11/2016 |
| WO | WO 2017/040915 A1 | 3/2017 |
| WO | WO 2018/213851 A1 | 11/2018 |

OTHER PUBLICATIONS

Extended European Search Report, dated Apr. 20, 2016, in connection with Application No. EP 13832980.0.
International Search Report and Written Opinion, dated Jan. 3, 2014, in connection with Application No. PCT/US2013/057636.
International Preliminary Report on Patentability, dated Aug. 1, 2014, in connection with Application No. PCT/US2013/057636.
International Search Report and Written Opinion, dated Jun. 16, 2014, in connection with Application No. PCT/US2013/076475.
Supplementary Partial European Search Report, dated Oct. 20, 2016, in connection with Application No. EP 14753802.9.
European Search Report, dated May 27, 2019, in connection with Application No. EP 14753802.9.
International Search Report and Written Opinion, dated May 12, 2014, in connection with Application No. PCT/US2014/017508.
International Search Report and Written Opinion, dated Nov. 27, 2015, in connection with Application No. PCT/US2015/045646.
International Search Report and Written Opinion, dated Nov. 22, 2016, in connection with Application No. PCT/US2016/050090.
International Search Report and Written Opinion, dated May 27, 2015, in connection with Application No. PCT/US2015/018746.
International Search Report and Written Opinion, dated Oct. 19, 2015, in connection with Application No. PCT/US2015/042441.
International Search Report and Written Opinion, dated Dec. 22, 2016, in connection with Application No. PCT/US2016/040250.
International Preliminary Report on Patentability, dated Jan. 2, 2018, in connection with Application No. PCT/US2016/040250.
Adiseshaiah et al., Nanomaterial standards for efficacy and toxicity assessment. Advanced Review. Jan. 2009;2(1):99-112.
Agarwal et al., Targeted gold nanorod contrast agent for prostate cancer detection by photoacoustic imaging. J. App. Phys. Sep. 15, 2007;102(6):064701-4.
Aggarwal et al., What's fueling the biotech engine—2009-2010. Nat. Biotechnol. Nov. 2010;28(11):1165-71.
Ahmed et al., Goldberg, S. N. Principles of and Advances in Percutaneous Ablation. Radiology. Feb. 2011; 258(2):351-369.
Akbari et al., Cancer detection using infrared hyperspectral imaging. Cancer Sci. Apr. 2011;102(4):852-7. doi: 10.1111/j.1349-7006. 2011.01849.x. Epub Feb. 11, 2011.
Akerman et al., Nanocrystal targeting in vivo. Proc Natl Acad Sci U S A. Oct. 1, 2002;99(20):12617-21. Epub Sep. 16, 2002.
Amstad et al., Triggered Release from Liposomes through Magnetic Actuation of Iron Oxide Nanoparticle Containing Membranes. Nano Letters. Apr. 13, 2011;11(4):1664-70.
Asfari et al., Establishment of 2-Mercaptoethanol-Dependent Differentiated Insulin-Secreting Cell Lines. Endocrinology. Jan. 1. 1992;130(1):167-178.

(56) References Cited

OTHER PUBLICATIONS

Bekis et al., A new agent for sentinel lymph node detection: preliminary results. J Radioanal. Nucl. Chem. Nov. 1, 2011;290(2):277-82. doi: 10.1007/s10967-011-1250-4.
Beljebbar et al., Ex vivo and in vivo diagnosis of C6 glioblastoma development by Raman spectroscopy coupled to a microprobe. Anal. Bioanal. Chem. Sep. 1, 2010;398(1):477-87.
Binkley et al., RNA ligands to human nerve growth factor. Nucleic Acids Research. Aug. 25, 1995;23(16):3198-3205.
Bogart et al., Photothermal Microscopy of the Core of Dextran-Coated Iron Oxide Nanoparticles During Cell Uptake. ACS Nano. Jul. 24, 2012;6(7):5961-71.
Bucci et al., Near Complete Surgical Resection Predicts a Favorable Outcome in Pediatric Patients with Nonbrainstem, Malignant Gliomas. Cancer. Aug. 15, 2004;101(4): 817-824.
Burckhardt et al., Virus Movements on the Plasma Membrane Support Infection and Transmission between Cells. PLoS Pathogens. Nov. 2009;5(11):e1000621:1-9.
Chen et al., Chelator-free synthesis of a dual-modality PET/MRI agent. Angew Chem Int Ed Engl. Dec. 9, 2013;52(50):13319-23. doi: 10.1002/anie.201306306. Epub Oct. 24, 2013.
Cho et al., A magnetic switch for the control of cell death signaling in in vitro and in vivo systems. Nat. Mater. Dec. 2012;11(12):1038-43.
Cirman et al., Selective Disruption of Lysosomes in Hela Cella Triggers Apoptosis Mediated by Cleavage of Bid by Multiple Papain-Like Lysosomal Cathepsins. J. of Biological Chem. Jan. 30, 2004;279(5):3578-3587.
Corchero et al., Biomedical applications of distally controlled magnetic nanoparticles. Trends Biotechnol. Aug. 2009;27(8):468-476.
Creixell et al., EGFR-Targeted Magnetic Nanoparticle Heaters Kill Cancer Cells without a Perceptible Temperature Rise. ACS Nano. Sep. 27, 2011;5(9):7124-7129.
Daniel et al., Lysosomal trapping as an important mechanism involved in the cellular distribution of perazine and in pharmacokinetic interaction with antidepressants. European Neuropsychopharmacology. Dec. 1, 1999;9(6):483-491.
De La Zerda et al., A Comparison Between Time Domain and Spectral Imaging Systems for Imaging Quantum Dots in Small Living Animals. Molecular Imaging and Biology. Oct. 1, 2010;12(5):500-508.
De La Zerda et al., Advanced contrast nanoagents for photoacoustic molecular imaging, cytometry, blood test and photothermal theranostics. Contrast Media Mol. Imaging. Sep. 2011;6(5):346-369.
De La Zerda et al., Carbon nanotubes as photoacoustic molecular imaging agents in living mice. Letters, Nature Nanotechnology. Sep. 2008;3(9):557-562.
De La Zerda et al., Ultrahigh Sensitivity Carbon Nanotube Agents for Photoacoustic Molecular Imaging in Living Mice. Nano Letters. Jun. 9, 2010;10(6):2168-2172.
Debbage et al., Molecular imaging with nanoparticles: giant roles for dwarf actors. Histochem. Cell. Biol. Nov. 1, 2008;130(5):845-75.
Declaration of Moritz Kircher for U.S. Appl. No. 14/464,642, 16 pages, executed Dec. 5, 2016.
Dobson, Remote control of cellular behaviour with magnetic nanoparticles. Nature Nanotechnology. Mar. 2008;3(3):139-143.
Domenech et al., Lysosomal Membrane Permeabilization by Targeted Magnetic Nanoparticles in Alternating Magnetic Fields. ACS Nano. Jun. 25, 2013;7(6):5091-5101.
Eghtedari et al., High Sensitivity of In Vivo Detection of Gold Nanorods Using a Laser Optoacoustic Imaging System. Nano Letters. Jul. 11, 2007;7(7):1914-1918.
El-Dakdouki et al., Development of Multifunctional Hyaluronan-Coated Nanoparticles for Imaging and Drug Delivery to Cancer Cells. Biomacromolecules. Apr. 9, 2012;13(4):1144-1151.
Ermilov et al., Laser optoacoustic imaging system for detection of breast cancer. Journal of Biomedical Optics. Mar.-Apr. 2009;14(2):024007-1-14.
Esenturk et al., Surface-enhanced Raman scattering spectroscopy via aold nanostars. Journal of Raman Spectroscopy. Jan. 2009;40(1): 86-91.
Eto et al., Glucose metabolism and glutamate analog acutely alkalinize pH of insulin secretory vesicles of pancreatic beta-cells. Am. J. Physiol. Endocrinol. Metab. Aug. 2003;285(2):E262-E271.
Fales et al., Silica-coated gold nanostars for combined surface-enhanced Raman scattering (SERS) detection and singlet-oxygen generation: a potential nanoplatform for theranostics. Langmuir. Oct. 4, 2011;27(19):12186-90.
Gaster et al., Matrix-insensitive protein assays push the limits of biosensors in medicine. Nature Medicine. Nov. 2009;15(11):1327-1332.
Ghosh et al., M13-templated magnetic nanoparticles for targeted in vivo imaging of prostate cancer. Nat. Nanotechnol. Oct. 2012;7(10):677-682.
Grimm et al., Cell Tracking. Principles and Applications. Radiologe. Jan. 1, 2007;47(1):25-33.
Grüttner et al., Synthesis and antibody conjugation of magnetic nanoparticles with improved specific power absorption rates for alternating magnetic field cancer therapy. Journal of Magnetism and Magnetic Materials. Apr. 1, 2007;311(1):181-186.
Guo et al., Multifunctional superparamagnetic nanocarriers with folate-mediated and pH-responsive targeting properties for anticancer drug delivery. Biomaterials. Jan. 1, 2011;32(1):185194.
Gupta et al., Cytotoxicity suppression and cellular uptake enhancement of surface modified magnetic nanoparticles. Biomaterials. May 1, 2005;26(13),:1565-1573.
Haaland et al., Improved Sensitivity of Infrared Spectroscopy by the APPiication of Least Squares Methods. APPiied SpectroscoPv. Sep. 1980;34(5):539-548.
Harmsen et al., Rational design of a chalcogenopyrylium-based surface-enhanced resonance Raman scattering nanoprobe with attomolar sensitivity. Nature Communications. Mar. 24, 2015;6(1):6570 I DOI: 10.1038/ncomms7570, pp. 1-9, Additional Information added, 8 pages.
Harmsen et al., Surface-enhanced resonance Raman scattering nanostars for high-precision cancer imaging. Science Translational Medicine. Jan. 21, 2015;7(271):1-8.
Haun et al., Magnetic nanoparticle biosensors. Wiley lnterdiscip Rev Nanomed Nanobiotechnol. May 2010;2(3):291-304.
Haun et al., Micro-NMR for Rapid Molecular Analysis of Human Tumor Samples. Science Translation Medicine. Feb. 23, 2011;3(71):1-13 with 2 additional pages of Editor's Summary.
Haun et al., Probing Intracellular Biomarkers and Mediators of Cell Activation Using Nanosensors and Bioorthogonal. ACS Nano. Apr. 26, 2011;5(4):3204-13.
Hofmann-Amtenbrink et al., Superparamagnetic nanoparticles for biomedical applications. Nanostructured Materials for Biomedical Applications. Jan. 2009:119-49.
Huang et al., Gold nanoparticles: interesting optical properties and recent applications in cancer diaanostics and theraov. Nanomedicine. Oct. 2007;2(5):681-693.
Huang et al., High Precision Imaging of Microscopic Spread of Blioblastoma with a Targeted Ultrasensitive SER RS Molecular Imaging Probe. Theranostics. May 7, 2016;6(8):1075-84.
Huang et al., Preparation of Silica-Encapsulated Hollow Gold Nanosphere Tags Using Layer-by-Layer Method for Multiplex Surface-Enhanced Raman Scattering Detection. Langmuir. Aug. 16, 2011;27(16):10228-10233.
Ivkov et al., Application of High Amplitude Alternating Magnetic Fields for Heat Induction of Nanoparticles Localized in Cancer. Clin Cancer Res. Oct. 1, 2005;11(19 Suppl):7093s-7103s.
Jellinek et al., Inhibition of Receptor Binding by High-Affinity RNA Ligands to Vascular Endothelial Growth Factor. Biochemistry. Aug. 1, 1994;33(34):10450-10456.
Kaaki et al., Magnetic Nanocarriers of Doxorubicin Coated with Poly(ethylene glycol) and Folic Acid: Relation between Coating Structure, Surface Properties, Colloidal Stability, and Cancer Cell Targeting. Langmuir. Jan. 17, 2012;28(2):1496-1505.

(56) References Cited

OTHER PUBLICATIONS

Kantelhardt et al., Multiphoton Excitation Fluorescence Microscopy of 5-Aminolevulinic Acid Induced Fluorescence in Experimental Gliomas. Laser in Surgery and Medicine. Apr. 2008;40(4):273-281.
Keren et al., Noninvasive molecular imaging of small living subjects using Raman spectroscopy. PNAS. Apr. 15, 2008;105(15):5844-5849.
Kim et al., Golden carbon nanotubes as multimodal photoacoustic and photothermal high-contrast molecular agents. Nature Nanotechnology. Oct. 2009;4(10):688-694.
Kim et al., Indocyanine-green-embedded PEBBLEs as a contrast agent of photoacoustic imaging. Journal of Biomedical Optics. Jul. 2007;12(4):044020-1-8.
Kim et al., Multifunctional nanstructured materials for multimodal imaging, and simultaneous imaging and therapy. Chem. Soc. Rev. Feb. 2009;38(2):372-90.
Kim et al., Silver-Coated Dye-Embedded Silica Beads: A Core Material of Dual Tagging Sensors Based on Fluorescence and Raman Scattering. ACS Applied Materials & Interfaces. Feb. 23, 2011;3(2):324-330.
Kim et al., Silver-particle-based surface-enhanced resonance Raman scattering spectroscopy for biomolecular sensing and recognition. Anal Bioanal Chem. May 1, 2007;388(1):81-8.
Kircher et al., A brain tumor molecular imaging strategy using a new triple-modality MRI-photoacoustic-Raman nanoparticle. Nature Medicine. May 2012;18(5):829-834.
Kircher et al., A Multimodal Nanoparticle for Preoperative Magnetic Resonance Imaging and Intraoperative Optical Brain Tumor Delineation. Cancer Research. Dec. 1, 2003;63(23):81228125.
Kircher et al., Molecular Body Imaging: MR Imaging, CT, and US. Part II. Applications, Radiology. Aug. 2012;264(2):349-368.
Kircher et al., Noninvasive cell-tracking methods. Nature Reviews: Clinical Oncology. Nov. 2011;8(11):677-688.
Knauth et al., Low-field interventional MRI in neurosurgery: finding the right dose of contrast medium. Neuroradiology. Mar. 1, 2001;43(3):254-258.
Knauth et al., Surgically Induced Intracranial Contrast Enhancement: Potential Source of Diagnostic Error in Intraoperative MR imaging. AJNR Am J Neuroradiol. Sep. 1, 1999;20(8):1547-1553.
Kodali et al., Optimally designed nanolayered metal-dielectric particles as probes for massively multiplexed and ultrasensitive molecular assays. PNAS. Aug. 3, 2010;107(31):13620-5.
Koljenovic et al., Raman Spectroscopic Characterization of Porcine Brain Tissue Using a Single Fiber-Optic Probe. Anal. Chem. Jan. 15, 2007;79(2):557-564.
Kornhuber et al., Lipophilic Cationic Drugs Increase the Permeability of Lysosomal Membranes in a Cell Culture System. Journal of Cellular Physiology. Jul. 2010;224(1):152-164.
Kozissnik et al., Magnetic fluid hyperthermia: Advances, challenges, and opportunity. International Journal of Hyperthermia. Dec. 1, 2013;29(8):706-714.
Kumar et al., Magnetic nanomaterials for hyperthermia-based therapy and controlled drug delivery. Advanced Drug Delivery Reviews. Aug. 14, 2011;63(9):789-808.
Laurent et al., Magnetic fluid hyperthermia: Focus on superparamagnetic iron oxide nanoparticles. Advances in Colloid Interface Science. Aug. 10, 2011;166(1-2):8-23.
Lee et al., Exchange-coupled magnetic nanoparticles for efficient heat induction. Nature Nanotechnology. Jul. 2011;6(7):418-422.
Lee et al., Mesoporous silica nanoparticle pretargeting for PET imaging based on a rapid bioorthogonal reaction in a living body. Angew Chem Int Ed Engl. Sep. 27, 2013;52(40):1054952. doi: 10.1002/anie.201304026. Epub Aug. 16, 2013.
Loening et al., A Free Software Tool for Multimodality Medical Imaqe Analysis. Molecular Imaqinq. Jul. 1, 2003;2(3):131-137.
Ludemann et al., Pharmacokinetic analysis of glioma compartments with dynamic Gd-DTPA-enhanced magnetic resonance imaging. Magnetic Resonance Imaging. Dec. 1, 2000;18(10):1201-1214.

Lusic et al., X-ray-computed tomography contrast agents. Chem. Rev. Mar. 13, 2013;113(3):1641-66.
Maeda et al., Tumor vascular permeability and the EPR effect in macromolecular therapeutics: a review. Journal of Controlled Release. Mar. 1, 2000;65(1-2):271-284.
Mannix et al., Nanomagnetic actuation of receptor-mediated signal transduction. Nature Nanotechnology. Jan. 2008;3(1):36-40.
Mansfield et al., Autofluorescence removal, multiplexing, and automated analysis methods for in-vivo fluorescence imaging. Journal of Biomedical Optics. Jul. 2005;10(4):041207-1-9.
Martin et al., Synthesis of bombesin-functionalized iron oxide nanoparticles and their specific uptake in prostate cancer cells. J. Nanopart. Res. Jun. 1, 2010;12(5):1599-1608.
Massoud et al., Molecular imaging in living subjects: seeing fundamental biological processes in a new light. Genes Dev. Mar. 1, 2003;17(5):545-80.
McNay et al., Surface-Enhanced Raman Scattering (SERS) and Surface-Enhanced Resonance Raman Scattering (SERRS): A Review of Applications. Applied Spectroscopy. Aug. 1, 2011;65(8):825-837.
Ozawa et al., Bromophenol Blue Staining of Tumors in a Rat Glioma Model. Neurosurgery. Nov. 1, 2005;57(4):1041-1047.
Pelletier, Quantitative Analysis Usingq Raman Spectrometry. Applied spectroscopy. Jan. 1, 2003;57(1):20A-42A.
Popp et al., Raman meets Medicine—Raman spectroscopy: a powerful tool in Biophotonics. Proc. of the SPIE. Oct. 5, 2009;7503: 6 pages. doi: 10.1117/12.837623.
Qian et al., In vivo tumor targeting and spectroscopic detection with surface-enhanced Raman nanoparticle tags. Nature Biotechnology. Jan. 2008;26(1):83-90.
Razansky et al., Multispectral opto-acoustic tomography of deep-seated fluorescent proteins in vivo. Nature Photonics. Jul. 2009;3(7):412-417.
Reinges et al., Course of brain shift during microsurgical resection of supratentorial cerebral lesions: limits of conventional neuronaviqation. Acta Neurochir. Apr. 1, 2004;146(4):369-377.
Robbins et al., Neoplasia and Other Disturbances of Cell Growth. Basic Pathology: Non-Neoplastic Cell Growth. 1976;2(3):68-105.
Sa et al, Development of Nanoaptamers Using a Mesoporous Silica Model Labeled with 99mTc for Cancer Taraetina. Oncoloav. 2012;82(4):213-217.
Schneider et al., Intraoperative MRI to guide the resection of primary supratentorial glioblastoma multiforme—a quantitative radiological analysis. Neuroradiology. Jul. 1, 2005;47(7):489-500.
Schulze et al., Uptake and Biocompatibility of Functionalized Poly(vinylalcohol) Coated Superparamagnetic Maghemite Nanoparticles by Synoviocytes InVitro. Journal of Nanoscience and Nanotechnology. Sep. 1, 2006;6(9-10):2829-2840.
Shinoda et al., Fluorescence-guided resection of glioblastoma multiforme by using high- dose fluorescein sodium. J Neurosurq. Sep. 1, 2003;99(3):597-603.
Short et al., Development and preliminary results of an endoscopic Raman probe for potential in vivo diagnosis of lung cancers. Optics Letters. Apr. 1, 2008;33(7):711-713.
Stewart et al., Raman Imaging. Annual Review of Analytical Chemistry. Jul. 19, 2012;5:337-360.
Stumm ER et al., Fluorescence-guided surgery with 5-aminolevulinic acid for resection of malignant glioma: a randomised controlled multicentre phase III trial. Oncology: The Lancet. May 1, 2006;7(5):392-401.
Stupp et al., Changing Paradigms—An Update on the Multidisciplinary Management of Malignant Glioma. The Oncologist. Feb. 1, 2006;11(2):165-180.
Sun et al, Self-Illuminating 64Cu-Doped CdSe/ZnS Nanocrystals in Vivo Tumor Imaging. Journal of the American Chemical Society. Feb. 5, 2014;136(5):1706-1709.
Thakor et al., Oxidative Stress Mediates the Effects of Raman-Active Gold Nanoparticles in Human Cells. Nanoparticle Cytotoxicity. Jan. 3, 2011;7(1):126-136.
Thakor et al.. The Fate and Toxicity of Raman-Active Silica-Gold Nanoparticles in Mice, Drug Delivery. Science Translation Medicine. Apr. 20, 2011;3(79):1-11.

(56) References Cited

OTHER PUBLICATIONS

Therasse et al., New guidelines to evaluate the response to treatment in solid tumors. J. Natl. Cancer Inst. Feb. 2, 2000;92(3):205-216.
Tognalli et al., From Single to Multiple Ag-Layer Modification of Au Nanocavity Substrates: A Tunable Probe of the Chemical Surface-Enhanced Raman Scattering Mechanism. ACS Nano. Jul. 26, 2011;5(7):5433-5443.
Tomasini et al., Molecular dynamics simulations of rupture in lipid bilayers. Experimental Biology Medicine. Feb. 2010;235(2):181-188.
Toms et al., lntraoperative Optical Spectroscopy Identifies Infiltrating Glioma Margins with High Sensitivity. Operative Neurosurgery. Oct. 1, 2005;57(4):382-391.
Tréhin et al., Fluorescen Nanoparticle Uptake for Brain Tumore Visualization. Neoplasia. Apr. 2006;8(4):302-11.
Tseng et al., Magnetic nanoparticle-mediated massively parallel mechanical modulation of single-cell behavior. Nature Methods. Nov. 2012;9(11):1113-19.
Tuerk et al., In vitro evolution of functional nucleic acids: high-affinity RNA ligands of HIV-1 proteins. Gene. Dec. 27, 1993;137(1):33-9.
Vikman et al., Insulin secretion is highly sensitive to desorption of plasma membrane cholesterol. The FASEB Journal. Jan. 2009;23(1):58-67.
Von Maltzahn et al., SERS-Coded Gold Nanorods as a Multifuntional Platform for Densely Multiplexed Near-Infrared Imaging and Photothermal Heating. Advanced Material Aug. 21, 2009;21(31):3175-3180.
Wahajuddin et al., Superparamagnetic iron oxide nanoparticles: magnetic nanoplatforms as drug carriers. Int. J. of Nanomedicine. 2012;7:3445-71.
Wang, Multiscale photoacoustic microscopy and computer tomography. Nature Photonics. Sep. 2009;3(9):503-9.
Wieboldt, Understanding Raman Spectroscopy Parameters. Spectrscopy, Special Issue. Jun. 1, 2010: 6 pages.
Wust et al., Hyperthermia in combined treatment of cancer. The Lancet Oncology.Aug. 1, 2002;3(8):487-497.
Xu et al., Differential Internalization of Superparamagnetic Iron Oxide Nanoparticles in Different Types of Cells. J. Nanoscience Nanotechnology. Nov. 1, 2010;10(11):7406-7410.
Yi et al, Facile preparation of Au/Ag bimetallic hollow nanospheres and its application in surface-enhanced Raman scatterina. Applied Surface Science. Oct. 15, 2011;258(1):212-217.
Yigit et al, Noninvasive MRI-SERS Imaging in Living Mice Using an Innately Bimodal Nanomaterial. ACS NANO. Feb. 22, 2011;5(2):1056-1066.
Yigit et al., In vivo and ex vivo applications of gold nanoparticls for biomedical SERS imaging. Am. J. Nucl. Med. Mol. Imaging. 2012;2(2):323-341.
Yuan et al., Quantitative Surface-Enhanced Resonant Raman Scattering Multiplexing of Biocompatible Gold Nanostars for in Vitro and ex Vivo Detection. Analytical Chemistry. Jan. 2, 2013;85(1):208-212.
Zavaleta et al., Multiplexed imaging of surface enhanced Raman scattering nanotags in living mice using noninvasive Rama spectroscopy. PNAS. Aug. 11, 2009;106(32):13511-6.
Zavaleta et al., Noninvasive Raman Spectroscopy in Living Mice for Evaluation of Tumor Targeting with Carbon Nanotubes. Nano Letters. Sep. 10, 2008;8(9):2800-5.
Zavaleta et al., Preclinical Evaluation of Raman Nanoparticle Biodistribution for their Potential Use in Clinical Edoscopy Imaging. Small. Aug. 8, 2011;7(15):2232-40.
Zavaleta et al., Raman's "Effect" on Molecular Imaging. J. Nucl. Med. Dec. 1, 2011;52(12):1839-44.
Zhang et al. Alternating Magnetic Fields Trigger Apoptosis by Destruction of Lysosomes with LAMP1-Targeted Nanoparticles. Biophysical Journal. Feb. 2, 2011;100(3):472.
Zhang et al., Dynamic magnetic fields remote-control apoptosis via nanoparticle rotation. ACS Nano. Apr. 22, 2014;8(4):3192-201.
Zhang et al., Molecular Imaging with SERS-Active Nanoparticles. Small. Dec. 2, 2011;7(23):3261-9.
Zong et al., A SERS and fluorescence dual mode cancer cell targeting probe based on silica coated AulmAa core-shell nanorods, Talanta, Aug. 15, 2012;97:368-375.
U.S. Appl. No. 14/423,946, filed Feb. 25, 2015, Kircher et al.
U.S. Appl. No. 14/653,177, filed Jun. 17, 2015, Harmsen et al.
U.S. Appl. No. 16/123,361, filed Sep. 6, 2018, Harmsen et al.
U.S. Appl. No. 14/768,117, filed Aug. 14, 2015, Kircher et al.
U.S. Appl. No. 14/464,642, filed Aug. 20, 2014, Kircher et al.
U.S. Appl. No. 15/255,611, filed Sep. 2, 2016, Kircher et al.
U.S. Appl. No. 15/329,876, filed Jan. 27, 2017, Wall et al.
EP 13832980.0, Apr. 20, 2016, Extended European Search Report.
PCT/US2013/057636, Jan. 3, 2014, International Search Report and Written Opinion.
PCT/US2013/057636, Aug. 1, 2014, International Preliminary Report on Patentability.
PCT/US2013/076475, Jun. 16, 2014, International Search Report and Written Opinion.
EP 14753802.9, Oct. 20, 2016, Supplemental Partial European Search Report.
EP 14753802.9, May 27, 2019, European Search Report.
PCT/US2014/017508, May 12, 2014, International Search Report and Written Opinion.
PCT/US2015/045646, Nov. 27, 2015, International Search Report and Written Opinion.
PCT/US2016/050090, Nov. 22, 2016, International Search Report and Written Opinion.
PCT/US2015/018746, May 27, 2015, International Search Report and Written Opinion.
PCT/US2015/042441, Oct. 19, 2015, International Search Report and Written Opinion.
PCT/US2016/040250, Dec. 22, 2016, International Search Report and Written Opinion.
PCT/US2016/040250, Jan. 2, 2018, International PreliminaryGW/ Report on Patentability.
U.S. Appl. No. 16/888,215, filed May 29, 2020, Wall et al.
U.S. Appl. No. 16/632,317, filed Jan. 17, 2020, Kircher et al.
PCT/US2018/042984, Oct. 12, 2018, International Search Report and Written Opinion.
PCT/US2018/042984, Jan. 30, 2020, International Preliminary Report on Patentability.
International Search Report and Written Opinion, dated Oct. 12, 2018, in connection with Application No. PCT/US2018/042984.
International Preliminary Report on Patentability, dated Jan. 30, 2020, in connection with Application No. PCT/US2018/042984.
Pestovskii et al., Investigation into the growth of gold nanoparticles immobilized on a mica surface due to tetrachloroauric acid reduction by hydorgen peroxide. Nanotechnologis in Russia. May 1, 2011; 6(3-4):189-195.

* cited by examiner

| Product | Seed | Reduction Rate |
|---|---|---|
|  |  | $\geq 1.4 \times 10^{-4}\ M\ s^{-1}$ |
|  |  | $\geq 1.4 \times 10^{-4}\ M\ s^{-1}$ |
|  |  | $\geq 1.4 \times 10^{-4}\ M\ s^{-1}$ |
|  |  | $\geq 7.3 \times 10^{-6}\ M\ s^{-1}$<br>$\leq 1.4 \times 10^{-4}\ M\ s^{-1}$ |
|  |  | $\geq 7.3 \times 10^{-6}\ M\ s^{-1}$<br>$\leq 1.4 \times 10^{-4}\ M\ s^{-1}$ |
|  |  | $\geq 9.3 \times 10^{-8}\ M\ s^{-1}$<br>$\leq 7.3 \times 10^{-6}\ M\ s^{-1}$ |
|  |  | $\geq 9.3 \times 10^{-8}\ M\ s^{-1}$<br>$\leq 7.3 \times 10^{-6}\ M\ s^{-1}$ |

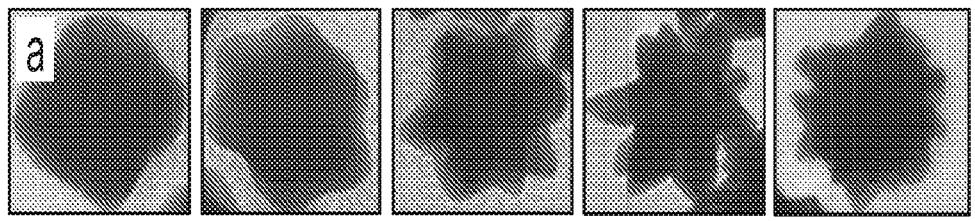
Figure 30A
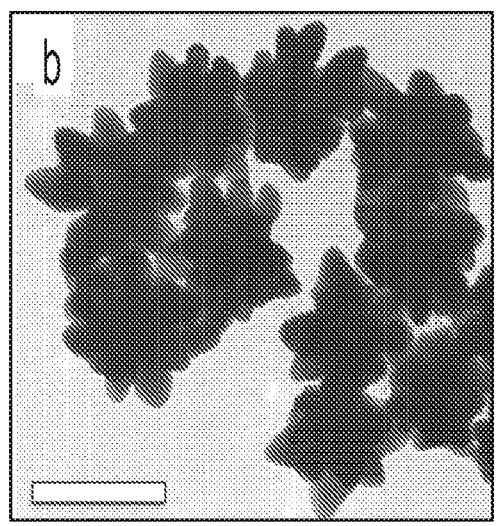
Figure 30B
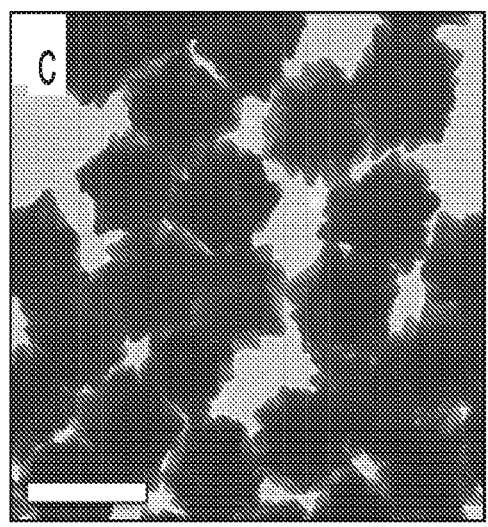
Figure 30C
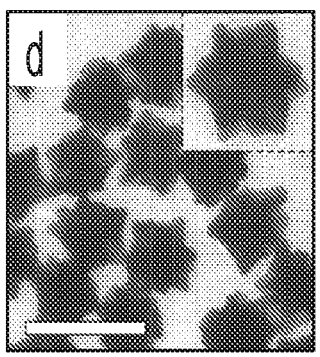 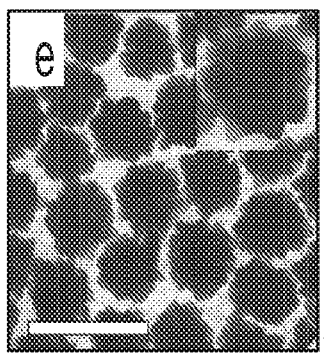 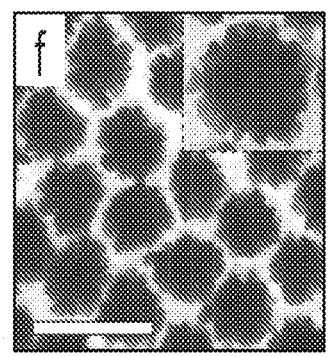
Figure 30D  Figure 30E  Figure 30F a b m = Total # of sites in step
n = # of sites in largest fragment
m = 7, n = 4 c d e

ANISOTROPIC PARTICLES, METHODS AND USES THEREOF

CROSS REFERENCE TO RELATED APPLICATIONS

This application is a national stage filing under 35 U.S.C. § 371 of International PCT Application, PCT/US2016/040250, filed Jun. 30, 2016, which claims priority under 35 U.S.C. § 119(e) to U.S. Provisional Application Ser. No. 62/187,703, filed Jul. 1, 2015, each of which is hereby incorporated by reference.

GOVERNMENT SUPPORT

This invention was made with government support under grant nos. K08 CA163961, P30 CA008748, R01 EB017748, CA163961, IGERT-0965983 (C.M.D.), and CHE-0847997 (C.M.D.) awarded by the National Institutes of Health and the National Science Foundation. The government has certain rights in the invention.

BACKGROUND

Nanoparticle systems (e.g., gold nanoparticles) have tremendous potential and are useful in a wide variety of contexts, including in electronics (e.g., as transistors or conductors, useful among other things in printable inks and/or electronic chips, for example, to connect components such as resistors, conductors, and/or other elements), to generate heat (e.g., when excited by radiation, for use in photodynamic and/or hyperthermia therapy), to deliver payloads (e.g., therapeutic, diagnostic, and/or imaging payloads), sensor technologies (e.g., colorimetric sensors, for example that identify foods suitable for consumption), for imaging indications (e.g., utilizing transmission electron microscopy, surface enhanced Raman spectroscopy and/or light scattering technologies), and catalysis (e.g., to catalyze selective oxidation reactions and/or to reduce production of nitrogen oxides or other toxic or environmentally harmful compounds). Nanoparticle systems are of particular interest for use in imaging tumor resection boundaries and/or for detecting biomarkers (e.g., in the diagnosis of heart diseases, cancer, infection, etc.). Nanoparticle systems are also often employed in lateral flow assays such as home pregnancy tests. Certain nanoparticle systems are also being developed for fuel cell and/or alternative energy applications.

There is a continuing need for improved nanoparticle systems, for both medical and/or non-medical applications. There is further a need for improved nanoparticle systems with unpassivated surfaces.

SUMMARY

The present invention provides new nanoparticle systems and technologies relating thereto. Among other things, the present invention provides systems for preparing nanoparticle cores of particular shapes (e.g., anisotropic metallic nanoparticle cores). The present invention recognizes the source of a problem in various standard strategies for producing shaped nanoparticle cores, and particularly appreciates that most such standard strategies utilize toxic materials that are difficult or impossible to remove completely from produced nanoparticle compositions. Furthermore, the present invention develops, in some embodiments, new methods of precisely controlling shapes and sizes of the produced nanoparticles without surface passivation.

The present invention provides, among other things, nanoparticle core preparation technologies that utilize only green chemicals. The present invention provides nanoparticle core preparation that can permit preparation of cores of a variety of different shapes utilizing the same set of reactants. In some embodiments, the present invention provides sets of reaction components that are sufficient to generate any of a variety of different nanoparticle core shapes.

In some embodiments, the present invention recognizes the source of a problem with certain technologies that attempt to control nanoparticle core shape by blocking growth in particular direction(s) (e.g., surface passivation). In some embodiments, the present invention provides nanoparticle core preparation technologies that activate core growth in particular desired direction(s) to produce nanoparticles having desired shapes (e.g., nanoplates, nanorods, nanostars, etc.) (e.g., as opposed to some conventional systems that achieved synthesis of nanoparticles at the expense of surface passivation). In some embodiments, steps may also be taken to block growth in some directions; in some embodiments, no such blocking steps are taken.

In some embodiments, the present invention recognizes the source of a problem with certain technologies that attempt to control nanoparticle core shape, which problem arises from and/or is embodied in presence of potentially reactive entities that persist in nanoparticle core preparation systems. In some embodiments, the present invention provides nanoparticle core preparation technologies that utilize dialysis and/or other strategies to remove potentially reactive species.

In some embodiments, the present invention develops and defines "rules" (e.g., relating ratios of reaction components and/or rates of reaction to degree, type, and/or location of surface activation) for nanoparticle core surface activation and/or etching, so that substantially any shape of nanoparticle core can be prepared by following the rules.

In some embodiments, the present invention provides nanoparticle compositions prepared according to methodologies described herein. In some embodiments, the present invention provides nanoparticle core preparations that are substantially free of at least certain specified toxic components and/or surfactants. In some embodiments, the present invention provides nanoparticle core preparations that are substantially free of at least certain specified polymer surface blocker components. In some embodiments, a provided composition is substantially free of surface-bound chemical species containing nitrogen, sulfur, or phosphorus. In some embodiments, a provided composition is substantially free of any chemical species, surface bound or otherwise, containing nitrogen, sulfur, or phosphorus. In some embodiments, a provided composition is substantially free of surface-bound chemical species containing atoms other than oxygen and hydrogen. In some embodiments, a provided composition is substantially free of chemical species, surface bound or otherwise, containing atoms other than the relevant metal, oxygen and hydrogen. In some embodiments, the present invention provides nanoparticle core preparations that are substantially free of at least certain specified reactive species. In some embodiments, a provided composition is considered to be "substantially free of" a particular species, agent or compound if the relevant species, agent or compound is not detected upon analysis using a technology such as high-resolution X-ray photoelectron spectroscopy.

In some embodiments, the present invention provides nanoparticle compositions in which at least 50, 55%, 60%, 65%, 70%, 75%, 80%, 85%, 90%, 95% or more have a core of common defined core shape. In some embodiments, the present invention provides nanoparticle compositions in which between 50-95%, 50-60%, 50-70%, 60-80%, 70-90%, 85-95% or more have a core of common defined core shape.

In some embodiments, the present invention provides nanoparticle compositions comprised of at least two distinct nanoparticle subpopulations, wherein each subpopulation is defined by a distinct shape of nanoparticle core.

In some embodiments, the present invention provides nanoparticle compositions comprised of at least two distinct nanoparticle subpopulations which are distinguishably detectable from one another. In some such embodiments, different subpopulations differ based on shape of the nanoparticle core, presence or thickness of a coating layer (e.g., a silica layer), and/or both.

In some embodiments, relevant nanoparticle core shapes are, for example, cages, cones, cylinders, cubes cuboids, hexagons, high index facet shapes (particularly for use in catalysis applications), icosahedra, octahedra, plates, prisms, pyramids, rings, rods, shells, spheres, stars, tetrahedra, etc. In some embodiments, relevant nanoparticle core shapes are discs, plates, rods, spheres, squares, or stars; in some embodiments, they are plates, rods, or stars. In some embodiments, a combination of any of the shapes listed above may be produced.

In some embodiments, the present invention provides nanoparticle compositions in which nanoparticle cores are characterized by a specified degree, type, and/or location of surface availability (e.g., of active surface area unpoisoned by chemical adsorbates) for a given application. In some embodiments, this specified degree is sufficient to outperform otherwise comparable nanoparticle compositions with less or different surface availability. In some embodiments, surface availability is assessed in or for a context relating to surface dependent applications.

In some embodiments, provided nanoparticle compositions comprise or consist of nanoparticles that each comprise a core and one or more coating layers.

In some embodiments, nanoparticles within provided nanoparticle compositions comprise at least one dopant (e.g., directly or indirectly associated with the core and/or with or in one or more layers).

In some embodiments, provided methods comprise an underpotential deposition agent (e.g., alternative metals, e.g., $Ag^+$) (e.g., wherein the underpotential deposition agent induces formation of grooves). In some embodiments, a fusion of the prepared metal seeds forms grooves.

Nanoparticle compositions as described herein may be used in any appropriate application. Those of ordinary skill in the art, reading the present specification, will appreciate that certain provided compositions are particularly useful in certain contexts. To give but one example, in some embodiments, provided nanoparticle compositions comprising two or more subpopulations of distinct core shapes may be particularly appropriate for use with transmission electron microscopy ("TEM") and/or other imaging technologies that benefit from presence of a plurality of shapes simultaneously in the same sample.

Definitions

In order for the present disclosure to be more readily understood, certain terms are defined below. Additional definitions for, or clarifications of, the following terms and other terms may be set forth throughout the specification.

In this application, the use of "or" means "and/or" unless stated otherwise. As used in this application, the term "comprise" and variations of the term, such as "comprising" and "comprises," are used in situations where listed items, elements, or steps are included and others may also be included. As used in this application, the terms "about" and "approximately" are used as equivalents. Any numerals used in this application, whether or not preceded by "about" or "approximately" are meant unless otherwise indicated to cover any normal fluctuations (e.g., standard errors or deviations), as would be appreciated by one of ordinary skill in the relevant art. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, biocompatible materials are biodegradable, e.g., into biocompatible components.

Biodegradable: As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

Comparable: The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Condensation layer: The term "condensation layer" refers to a layer assembled from a plurality of precursor units. In some embodiments, such assembly involves a traditional condensation reaction (e.g., resulting in release of water); however, those of ordinary skill in the art reading the present specification will appreciate that the term "condensation layer" is not limited to layers formed by any particular chemistry. Any layer that satisfies the requirements and description herein is a "condensation layer".

Illuminating: The term "illuminating" as used herein refers to application of a light source such as, for example, a near-infrared (NIR), visible, or ultraviolet (UV) light source. In some embodiments, illuminating comprises applying laser light. In some embodiments, illuminating comprises applying light of a wavelength appropriate to excite one or more responsive agents; in some such embodiments, responsive agents are comprised in provided particles. For example, one or more dopant entities, layers, and/or substrates may be or comprise a light-responsive agent.

Magnetic Resonance Imaging: The term "magnetic resonance imaging (MRI)" as used herein refers to a medical imaging technique most commonly used in radiology to visualize the structure and function of the body. It provides detailed images of the body in any plane. MRI uses no ionizing radiation, but uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a subject lies in a scanner, the hydrogen nuclei (i.e., protons) found in abundance in an animal body in water molecules, align with the strong main magnetic field. A second electromagnetic field that oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different tissues of the body (e.g., fat versus muscle) realign at different speeds, the different structures of the body can be revealed. Contrast agents may be injected intravenously to enhance the appearance of blood vessels, tumors or inflammation. MRI is used to image every part of the body, but is particularly useful in neurological conditions, disorders of the muscles and joints, for evaluating tumors and showing abnormalities in the heart and blood vessels.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Reference: The term "reference" is often used herein to describe a standard or control agent or value against which an agent or value of interest is compared. In some embodiments, a reference agent is tested and/or a reference value is determined substantially simultaneously with the testing or determination of the agent or value of interest. In some embodiments, a reference agent or value is a historical reference, optionally embodied in a tangible medium. Typically, as would be understood by those skilled in the art, a reference agent or value is determined or characterized under conditions comparable to those utilized to determine or characterize the agent or value of interest.

Sample: The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Stable: The term "stable," when applied to compositions herein, means that the compositions maintain one or more aspects of their physical structure (e.g., size range and/or distribution of particles) over a period of time. In some embodiments, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time under specified conditions. In some embodiments, a stable provided composition is one for which a biologically relevant activity is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. For example, if a population of nanoparticles is subjected to prolonged storage, temperature changes, and/or pH changes, and a majority of the nanoparticles in the composition maintain a diameter within a stated range, the nanoparticle composition is stable. In some embodiments, a stable composition is stable at ambient conditions. In some embodiments, a stable composition is stable under biologic conditions (i.e. 37° C. in phosphate buffered saline).

Subject: As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from allergy, etc.

BRIEF DESCRIPTION OF THE DRAWING

The Drawing, which is comprised of at least the following Figures, is for illustration purposes only, not for limitation.

FIG. 3A shows HRTEM of representative gold nanorod synthesized by the CTAB-mediated approach as viewed under standard conditions (tilt angle=0 degrees, acquisition time=2.0 s).

FIG. 3B presents HRTEM of representative gold nanorod synthesized by the $H_2O_2$-mediated approach viewed under standard conditions.

FIG. 3C shows nanorod from FIG. 3A viewed at a eucentric tilt angle of 30 degrees and acquisition time of 10 s. The CTAB bilayer can be clearly visualized.

FIG. 3D shows nanorod from FIG. 3B viewed at a eucentric tilt angle of 20 degrees and an acquisition time of 5 seconds.

FIG. 3E presents magnified image from FIG. 3C for elucidation of rod surface. Pointers identify CTAB bilayer.

FIG. 3F is a magnified image of FIG. 3D for clarity.

FIG. 3G provides EDS analysis of nanorods synthesized by the CTAB-mediated synthesis. The high bromide counts indicate that the nanorod surface is extensively covered by CTAB. The carbon counts are removed with the background signal of the carbon-coated TEM grid.

FIG. 3H gives EDS analysis of the nanorods synthesized by the $H_2O_2$-mediated method. Only gold is detected, demonstrating that the formation does not rely on facet blocking chemicals, and that the nanoparticle composition produced is substantially free of such chemicals.

FIGS. 16A-16C illustrate preferential growth of (FIG. 16A) nanoplates, (FIG. 16B) nanorods, and (FIG. 16C) nanostars under one-dimensional, two-dimensional, and three-dimensional nucleation conditions.

FIG. 16D illustrates an electron diffraction pattern of representative nanoplate (inset) in the [111] orientation demonstrating forbidden 1/3{22-4} reflection characteristic of stacking faults parallel to the dominant {111} faces.

Under one-dimensional nucleation conditions, these stacking faults result in small $\lambda_{hkl}^{ss}$ values at the sides facets where they are exposed, explaining the preferential growth of nanoplates.

Figure 16A:
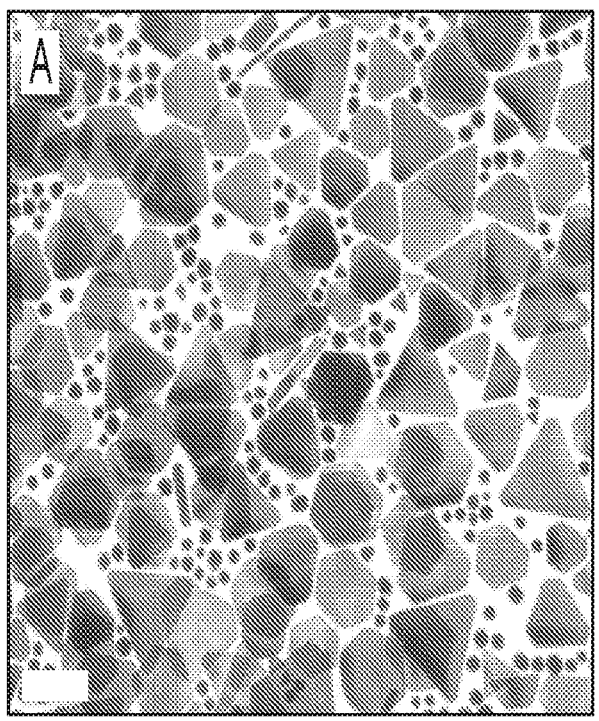
FIGS. 16A-16F illustrate synthetic control and mechanistic insights of anisotropic gold nanoparticle formation.
Figure 16B:
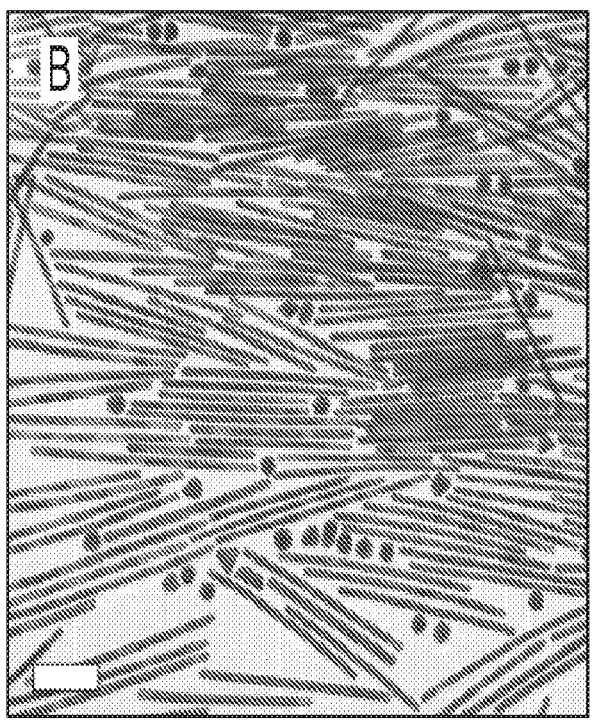
Figure 16C:
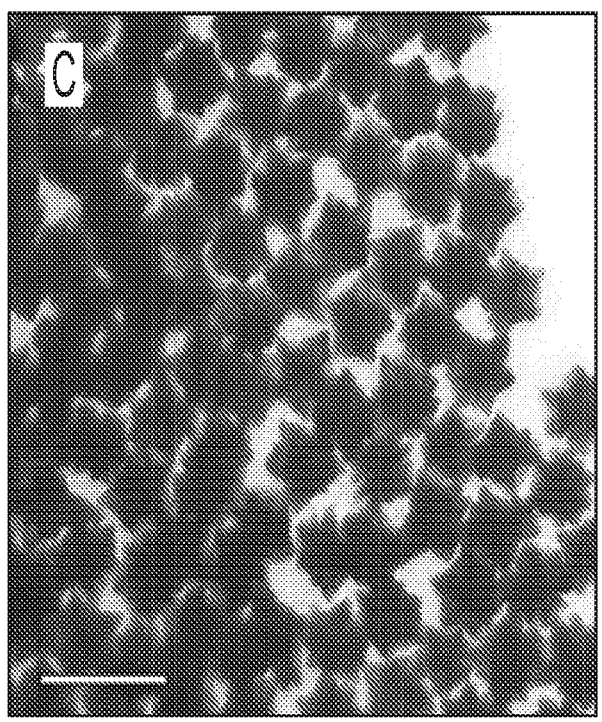
Figure 16D:
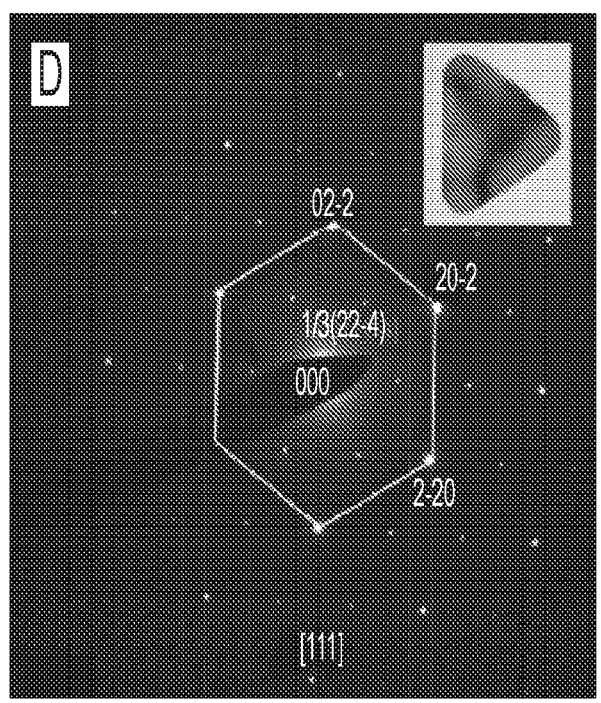
Figure 16E:
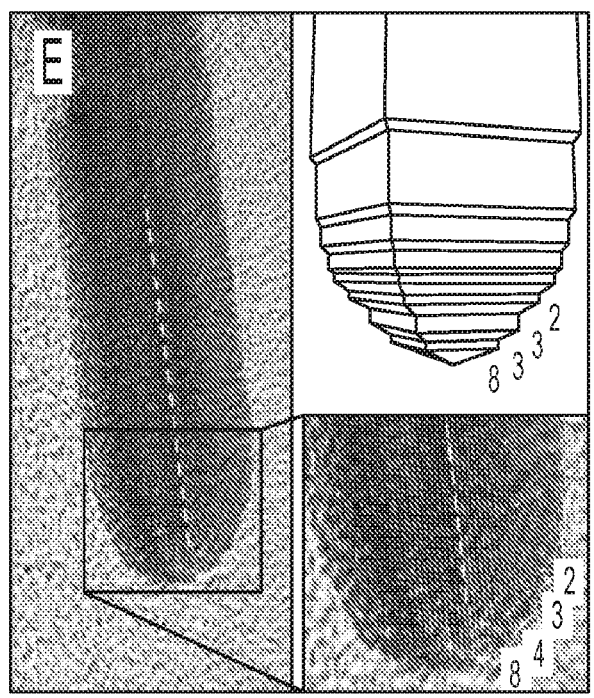

FIG. 16E shows a high-resolution transmission electron micrograph (HRTEM) of nanorod end facets reveals terraces with near-perfect steady-state spacing. The observed spacing in integer units of atomic diameters is 8, 4, 3, 2 and the theoretical steady state is 8, 3, 3, 2.

Figure 16F:
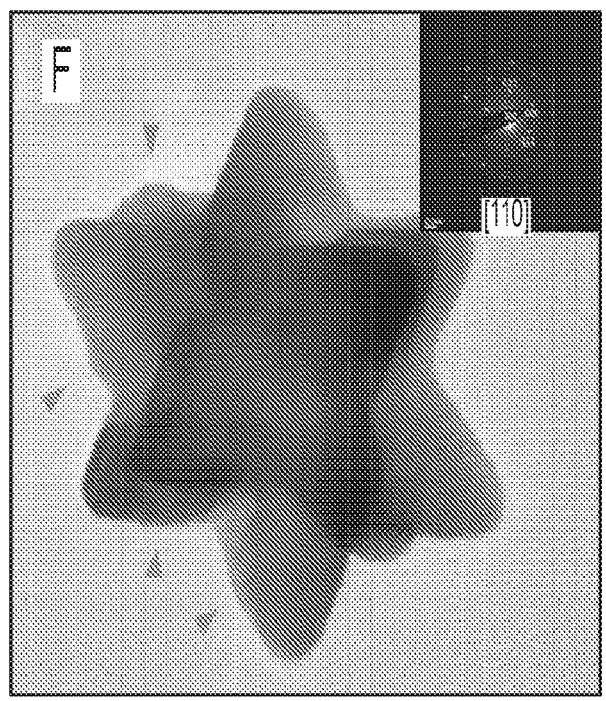

FIG. 16F shows a HRTEM of representative nanostar that demonstrates the existence of small dendritic side growths extending from the primary protrusions and varying in size. These small growths generate steps parallel to the surface of the protrusions. The electron diffraction pattern inset indicates that the protrusions primarily display {111} facets. The scale bars are 100 nm.

Figure 17A:
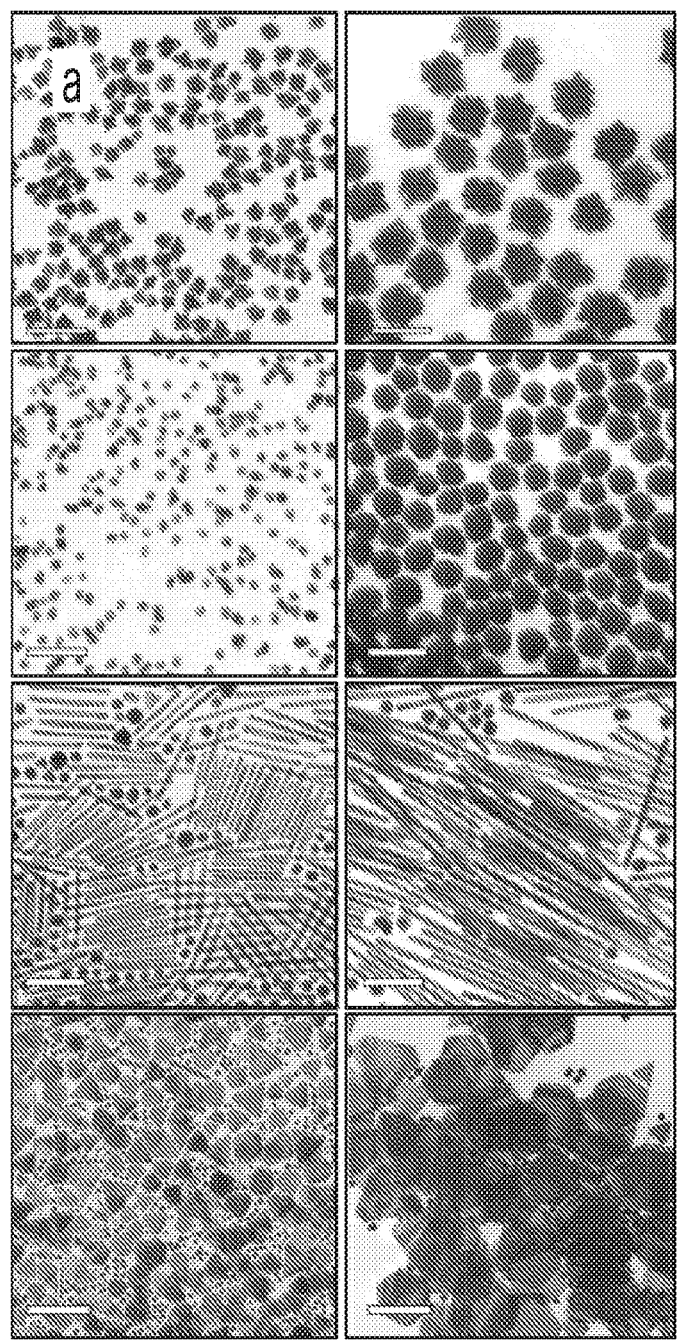
Figure 17B:
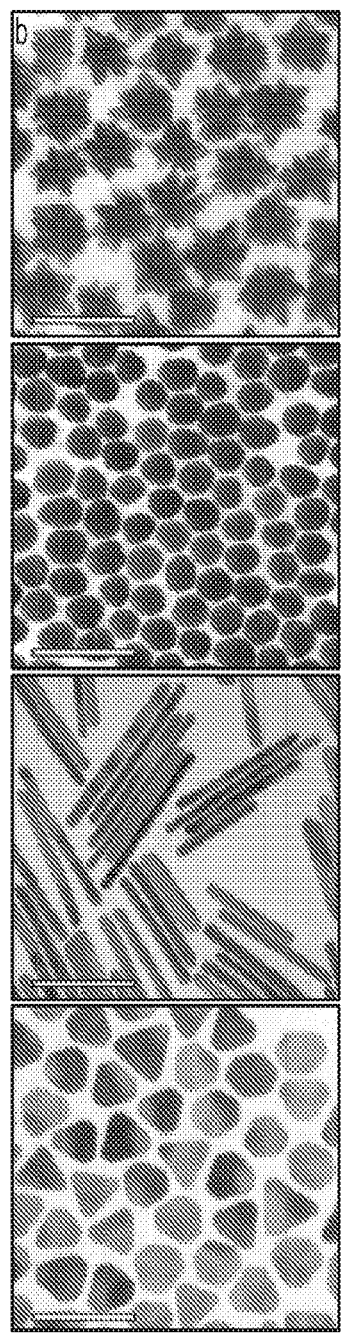

FIGS. 17A-17B show surfactant- and polymer-free shape control of gold nanoparticles as a function of reaction kinetics and seed structure.

FIG. 17A shows selective growth from the same batch of seeds by changing reaction kinetics.

FIG. 17B shows optimized protocol nanostars, nanospheres, nanorods, and nanoplates. Some embodiments described herein relate to controlling nanoparticle shape as a function of reduction rate (e.g., as shown in FIG. 17A). Some embodiments described herein relate to obtaining optimized results (e.g., optimal nanoparticle shapes).

Figure 18:
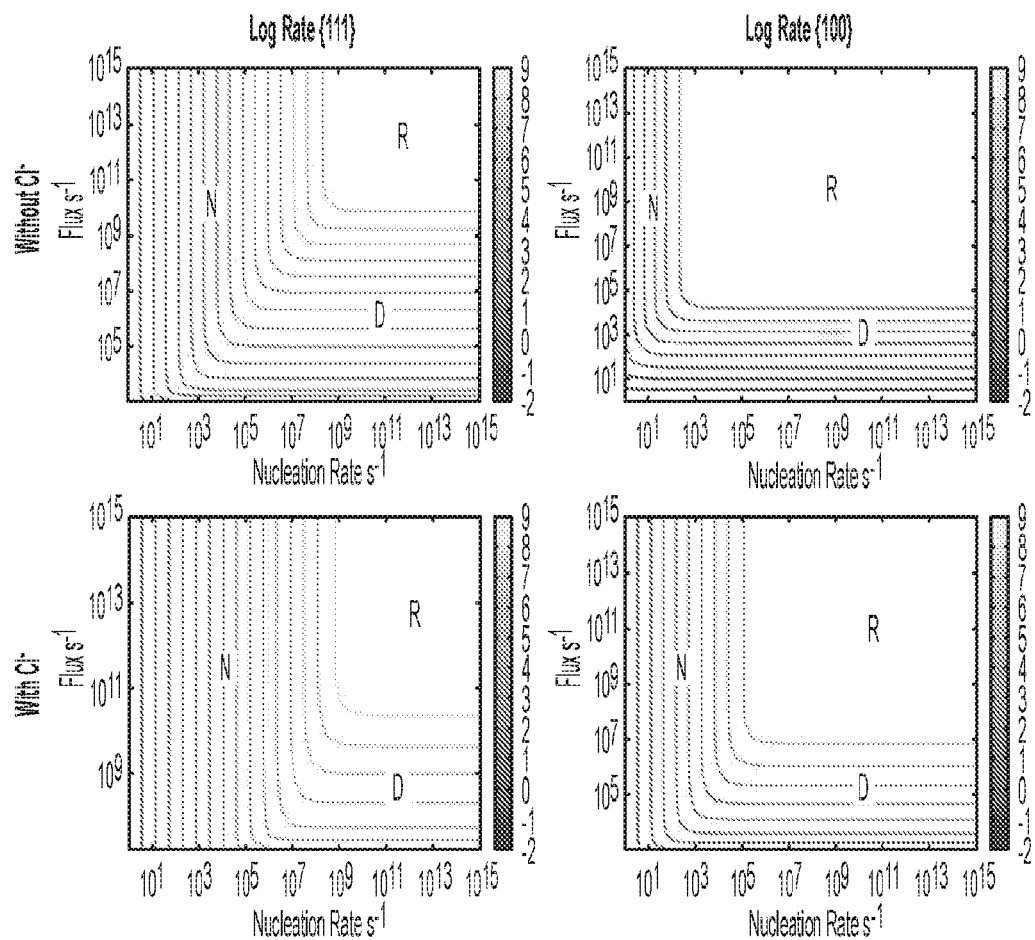

FIG. 18 illustrates Flux-Nucleation plots for {111} and {100} facets of gold nanocrystals. Three distinct regimes can be identified wherein the total facet growth rate is limited by either the nucleation rate (N), growth unit diffusion rate (D), or incorporation reaction rate (R). Decreased activation energies for various surface diffusion movements in presence of Cl$^-$ shift the location of the nucleation-limited, diffusion-limited, and reaction-limited regimes with respect to the case of reactions without Cl$^-$. In some embodiments, reactions that are carried out include Cl$^-$ from the gold precursor complex, as such, the plots at the bottom of FIG. 18 can be used for syntheses of gold nanocrystals. In some embodiments, crystal structure and reduction kinetics of metal precursors are dominant considerations (e.g., variables) in syntheses that are free from auxiliary agents.

Figure 19:
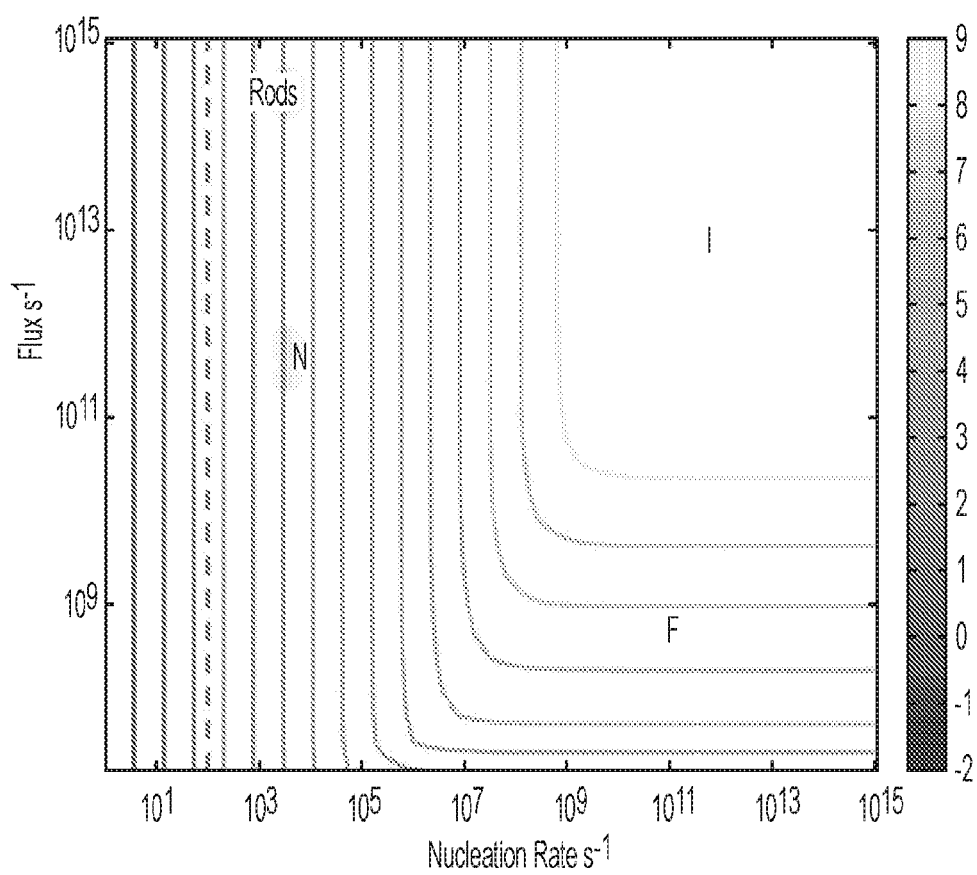

FIG. 19 illustrates experimental growth rate of gold nanorod {111} facets overlaid with a Flux-Nucleation plot. The contour shown in FIG. 19 is firmly within the monolayer nucleation-limited regime. From this information, synthesis of gold nanorods can be optimized by employing appropriate reaction conditions to favor monolayer nucleation at the {111} end facets over the {100} side facets. In some embodiments, crystal structure and reduction kinetics of metal precursors are dominant considerations (e.g., variables) in syntheses that are free from auxiliary agents. In some embodiments, crystal structure, including, in some embodiments crystal structure at nanoparticle surface, determines nucleation rate for a new monolayer (e.g., denoted by "N" in FIG. 18 and FIG. 19), and reduction kinetics determines a rate at which growth units diffuse to surface binding sites (e.g., denoted by "D" in FIGS. 18 and 19). In some embodiments, an additional consideration is a rate at which growth units react with binding sites to become incorporated into the crystal. In some embodiments, a rate at which growth units react with binding sites to become incorporated into the crystal becomes a dominant consideration under conditions of fast monolayer nucleation and growth unit diffusion (e.g., denoted by "R" in FIG. 18 and FIG. 19). In some embodiments, depending, for example, on physical parameters unique to a particular synthesis, including activation energies and/or vibrational frequencies of atoms moving on the crystal, the growth rate of a given facet can be governed by, for example, rate of monolayer nucleation, growth unit diffusion, growth unit incorporation, or any combination thereof. Some embodiments described herein relate to identifying particular ranges of reaction kinetics wherein the facet growth rate is determined almost exclusively by the rate of monolayer nucleation. Because monolayer nucleation rate is determined by surface structure of crystal seeds and flux of growth units to the nanoparticle, strategies to grow desired morphologies can be identified, for example, by choosing the appropriate seed structures and reaction kinetics. For example, in some embodiments, nanorods can be formed by choosing multiply twinned seeds and reduction kinetics that allow growth via monolayer birth and spread.

Figure 20:
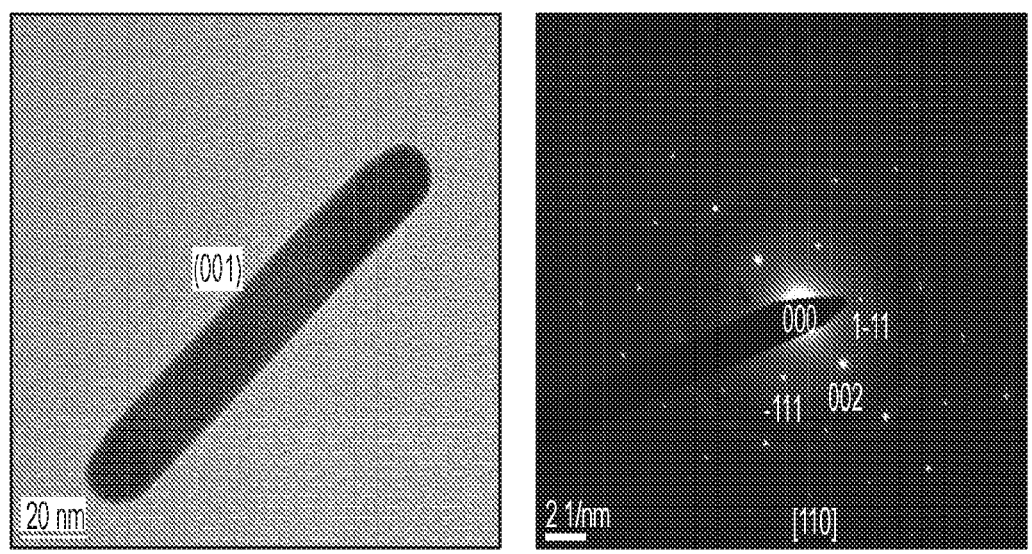

FIG. 20 shows a defect-free nanorod synthesized by a method that does not involve the use of surfactants and polymers (e.g., surfactant- and polymer-free method). In some embodiments, crystal growth processes can proceed by transient defect formation, such that the (nano)crystal surface has a particular structure during growth that induces the formation of a desired shape, but a different structure once growth completes (e.g., the defect disappears after growth). Formation of nanorods shown in FIG. 20 involves transient defect formation. For example, as shown in FIG. 20, single crystalline anisotropic particles can be generated by surfactant- and polymer-free synthesis. In some embodiments, transient defect formation is responsible for shape anisotropy that is observed, for example, in FIG. 20.

Figure 21:
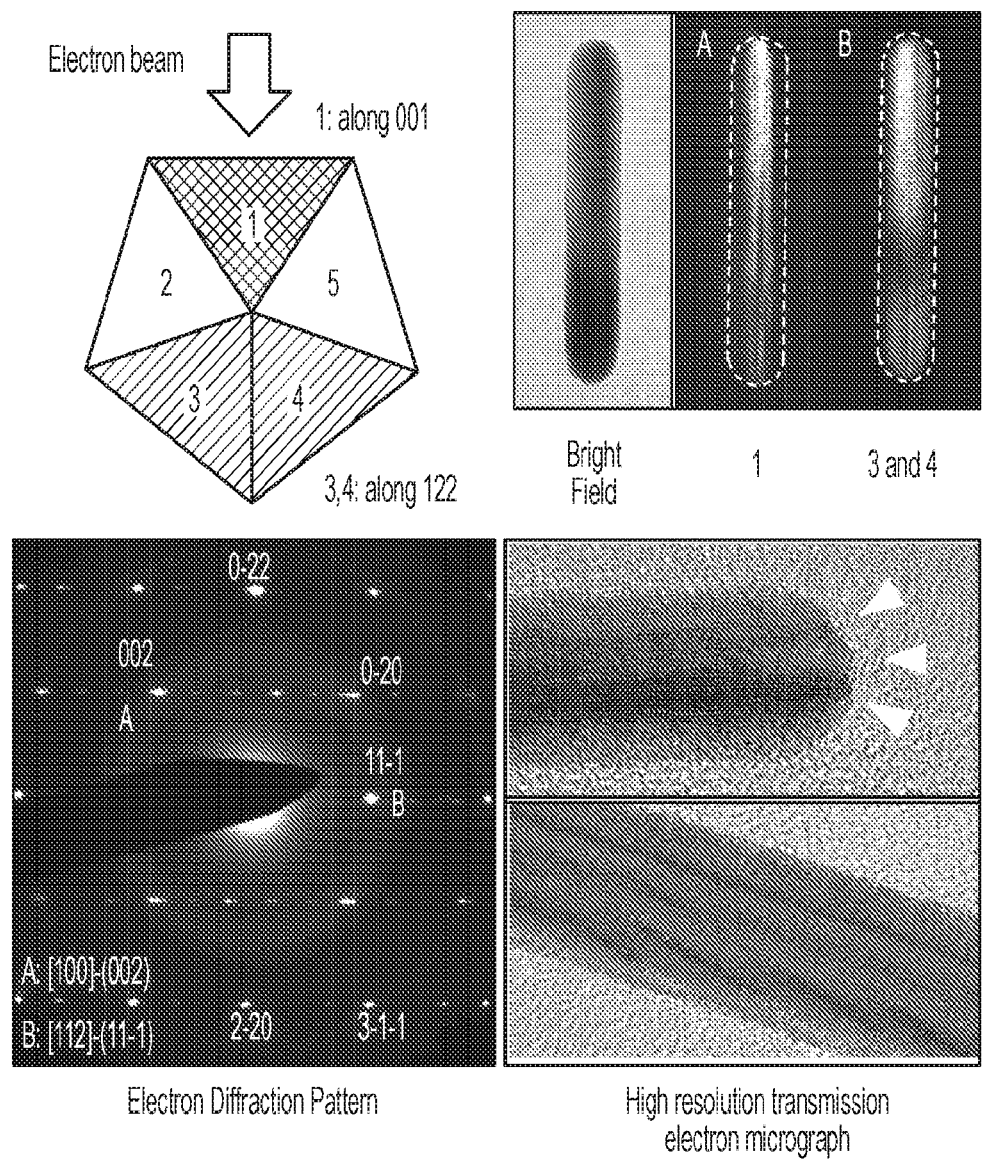

FIG. 21 shows structure of nanorods typically observed in the synthesis described in accordance with some embodiments described herein. Bright field images, dark field images, and electron diffraction reveal characteristic patterns of a five-fold twinned crystal structure, corresponding to the multiply-twinned seeds from which they were grown. The jagged surface of the end facets presents fast-growing re-entrant grooves, whereas the side facets are sufficiently smooth to be slow growing by comparison.

Figure 22:
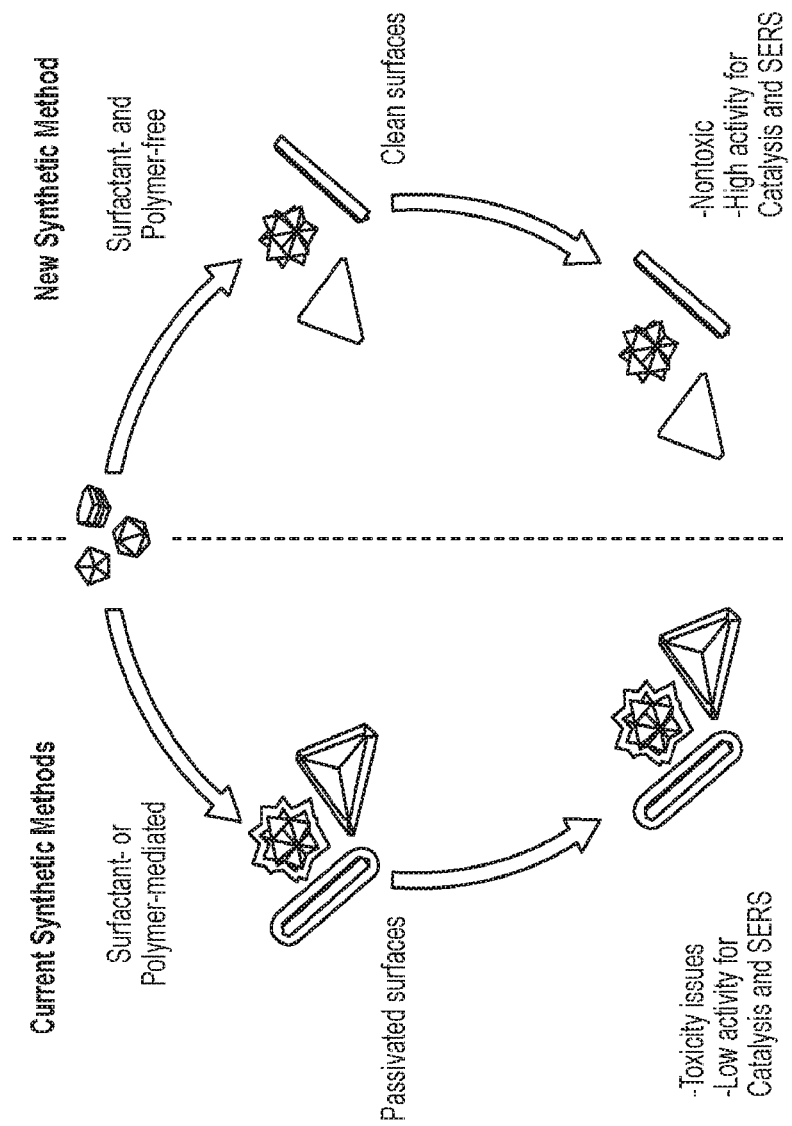

FIG. 22 shows a comparison of shape-controlled syntheses. Convention (or current) synthetic methods are described on the left, and the presented synthetic methods are described on the right.

Figure 23A:
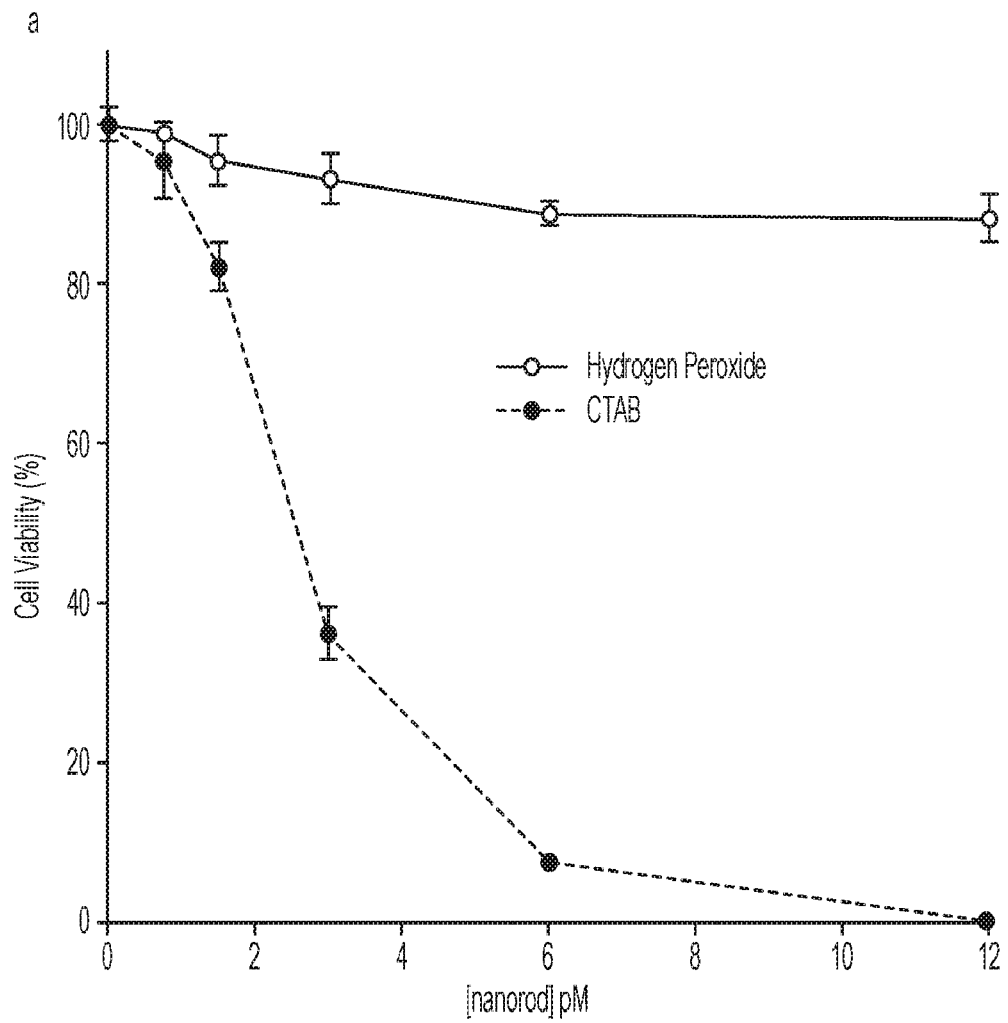
Figure 23B:
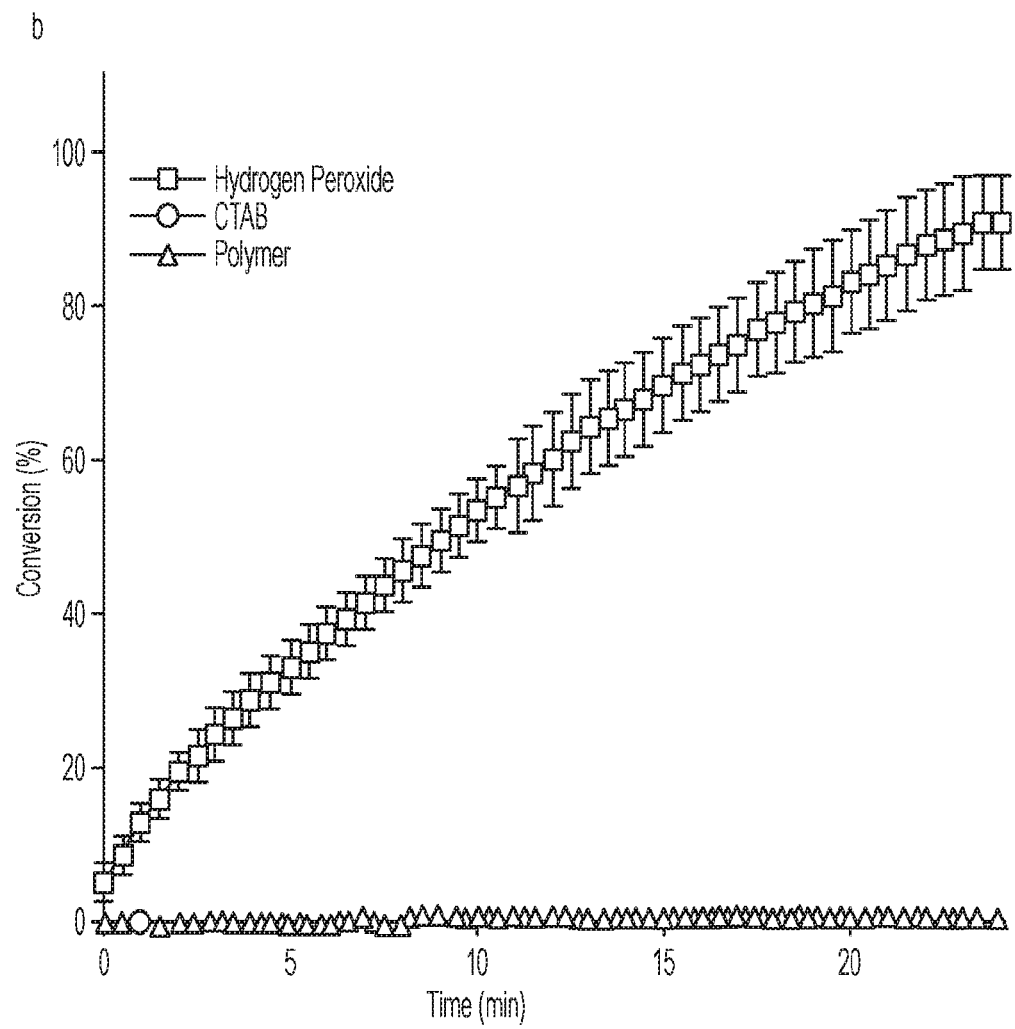
Figure 23C:
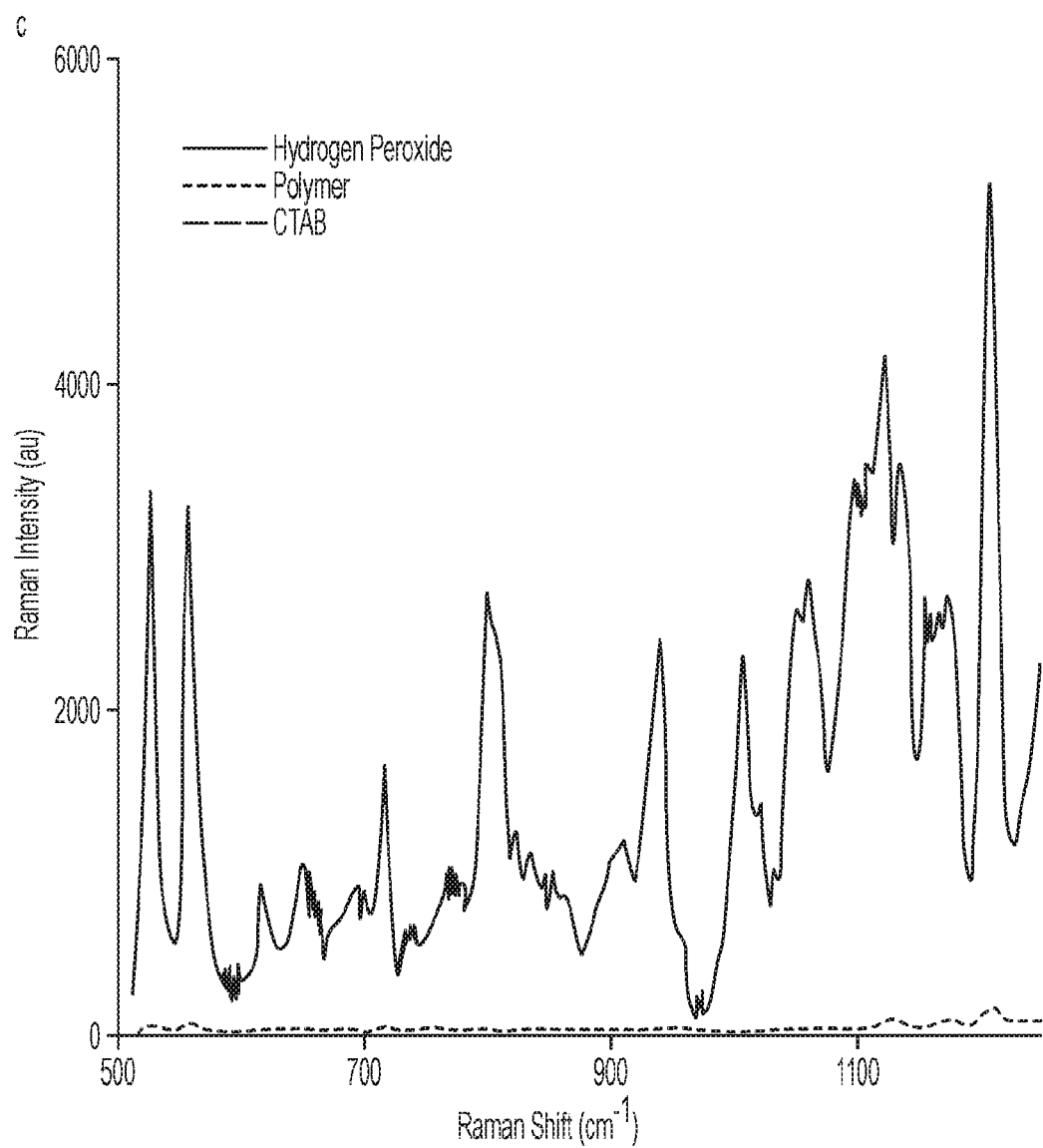

FIGS. 23A-23C show a comparison between gold nanoparticles synthesized by the present methods (hydrogen peroxide) and surfactant- and polymer-coated gold nanoparticles (CTAB and polymer). All nanoparticle mixtures were grown from the same seeds and comprised roughly about 25% rods, about 25% plates, and about 50% pseudospherical nanoparticles. Nanoparticle aggregation did not occur under the low dye concentrations employed in these experiments.

FIG. 23A compares cytotoxicity between gold nanoparticles synthesized by the present methods (hydrogen peroxide) and surfactant- and polymer-coated gold nanoparticles (CTAB and polymer).

FIG. 23B compares catalytic activity (oxidation of resazurin to resorufin) between gold nanoparticles synthesized by the present methods (hydrogen peroxide) and surfactant- and polymer-coated gold nanoparticles (CTAB and polymer).

FIG. 23C compares surface-enhanced Raman scattering (dye=IR-792) capabilities of gold nanoparticles synthesized by the methods described herein to conventionally-prepared nanoparticles (comparable dimensions) with surfactant (CTAB) and thiolated polyethylene glycol (polymer) coatings.

FIGS. 24A-24F illustrate results of a theoretical framework that is presented herein.

Figure 24A:
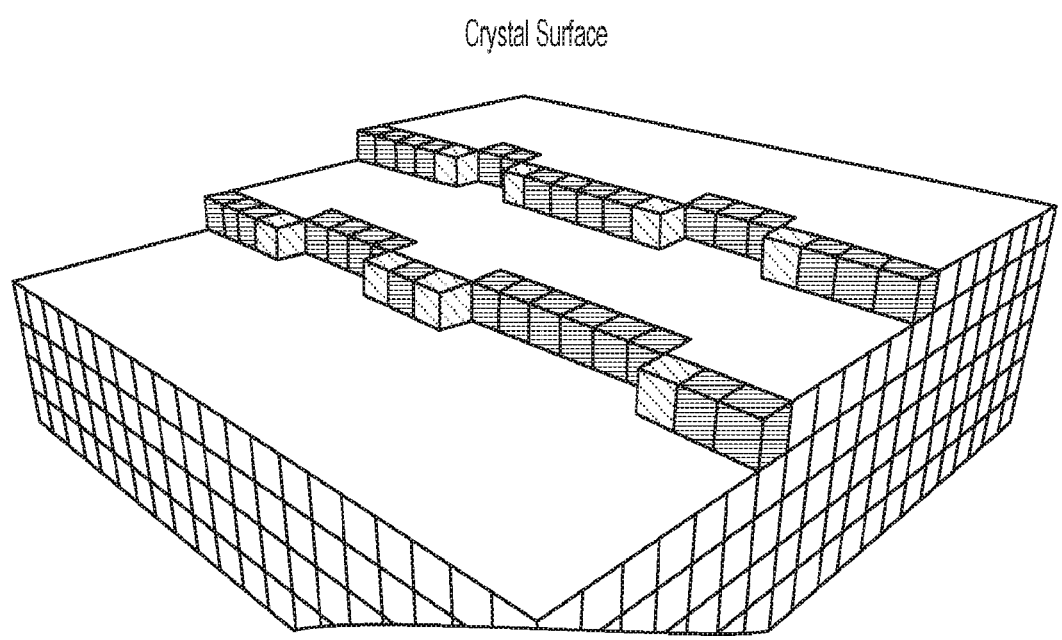

FIG. 24A shows a schematic of a crystal facet. In this schematic, the surface is populated by terrace (yellow), step (red), and kink (white) sites.

Figure 24B:
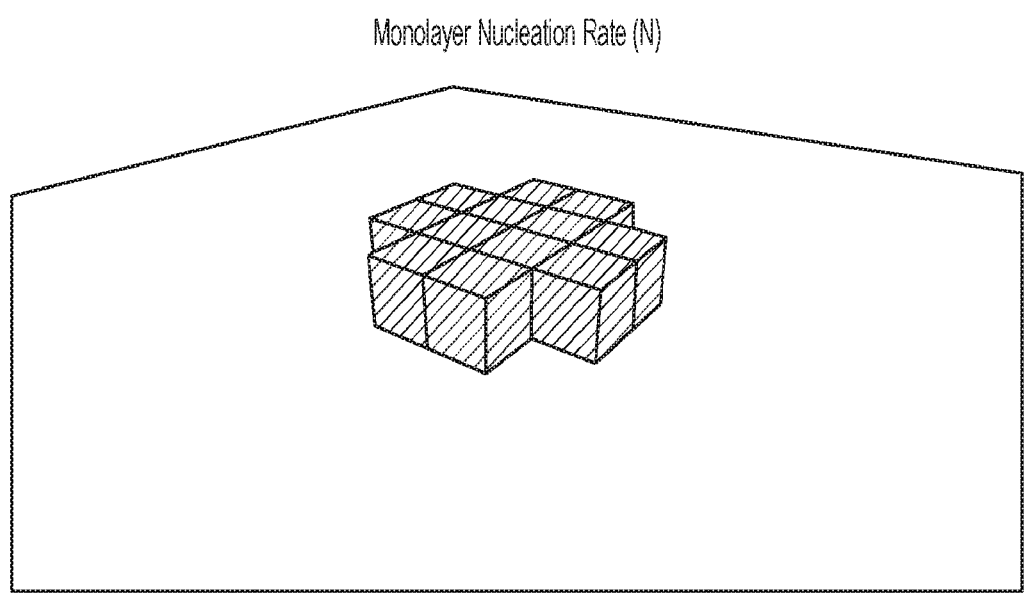
Figure 24C:
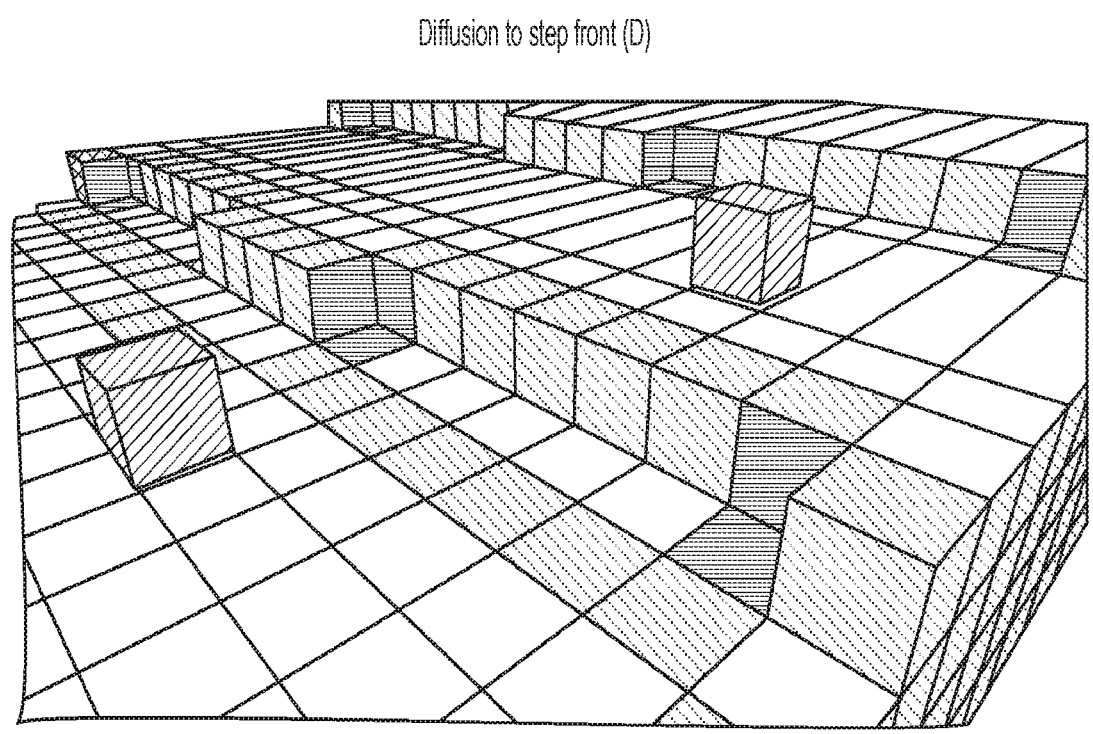
Figure 24D:
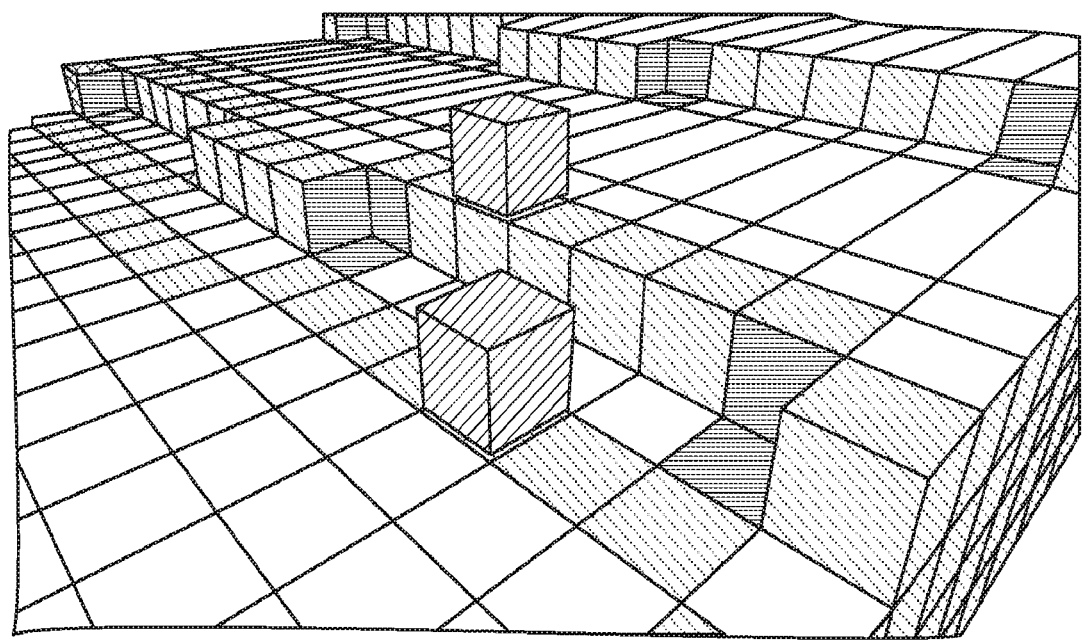

FIGS. 24B-24D show three primary processes influencing the growth rate of a crystal facet.

FIG. 24B shows that a monolayer nucleation rate (N) is the rate at which a critical nucleus (blue)—an island of growth units that will continue to grow rather than dissolve—forms on a facet (yellow).

FIG. 24C shows that a "diffusion" rate can refer to different processes in different theories. Herein, the rate of diffusion (D) is defined as the flux of growth units to the step front or the region of terrace sites that are one jump from step or kink sites (highlighted in light yellow). This definition separates growth unit diffusion from the incorporation reaction process.

FIG. 24D shows that an incorporation "reaction" rate (R) is defined in the presented treatment as the net rate at which growth units in the step front (highlighted in light yellow) diffuse into kink binding sites (red). The delivery of growth units to kink binding sites is divided into two regimes: diffusion of growth units to the step front, and incorporation reaction from the step front into the kink binding sites.

Figure 24E:
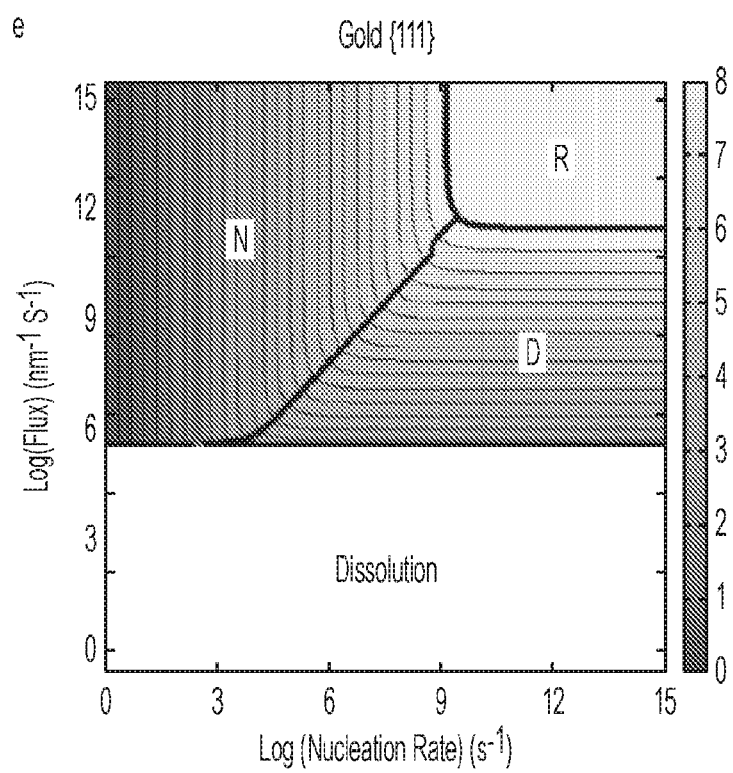
Figure 24F:
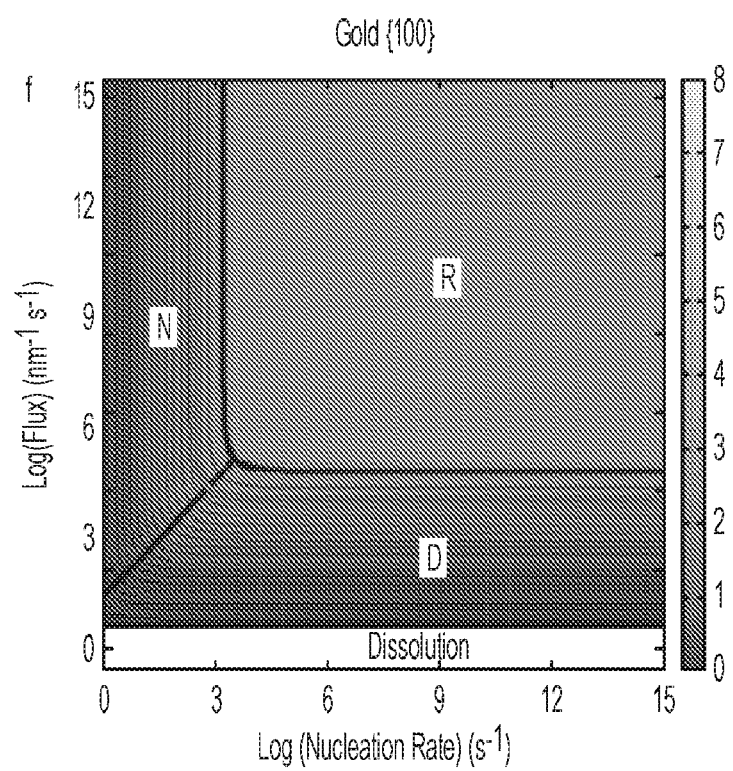

FIGS. 24E-24F shows that the presented theoretical framework produces contour plots of facet growth rates that highlight the rate-limiting growth process as a function of experimental conditions for (FIG. 24E) {111} and (FIG. 24F) {100} facets of gold nanoparticles. The red contour denotes the experimental growth rate at which secondary nucleation—the formation of new seeds—occurs. Polyhedra like rods and plates form below this rate.

Figure 25A:
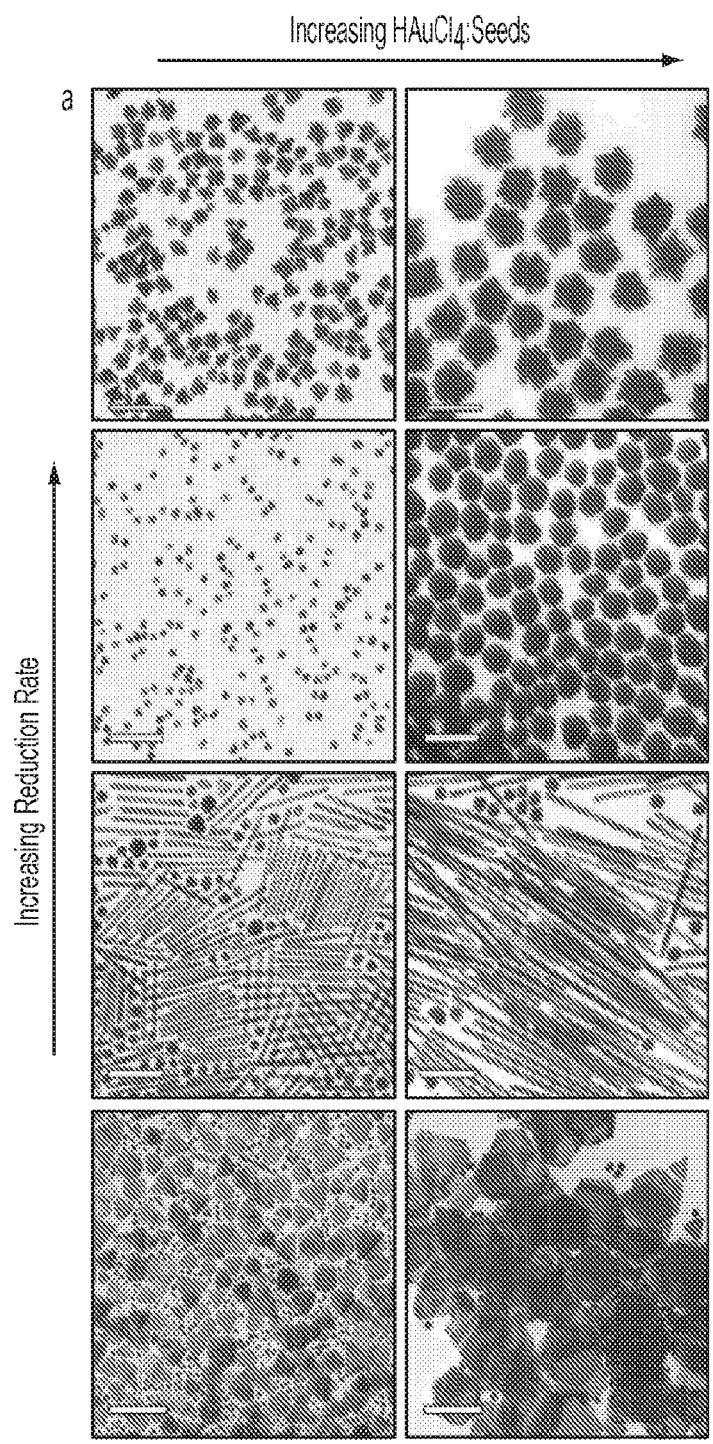
Figure 25B:
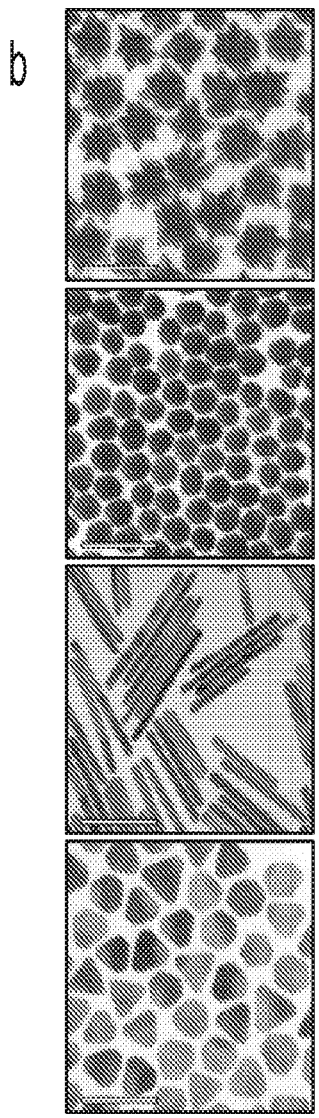
Figure 25C:
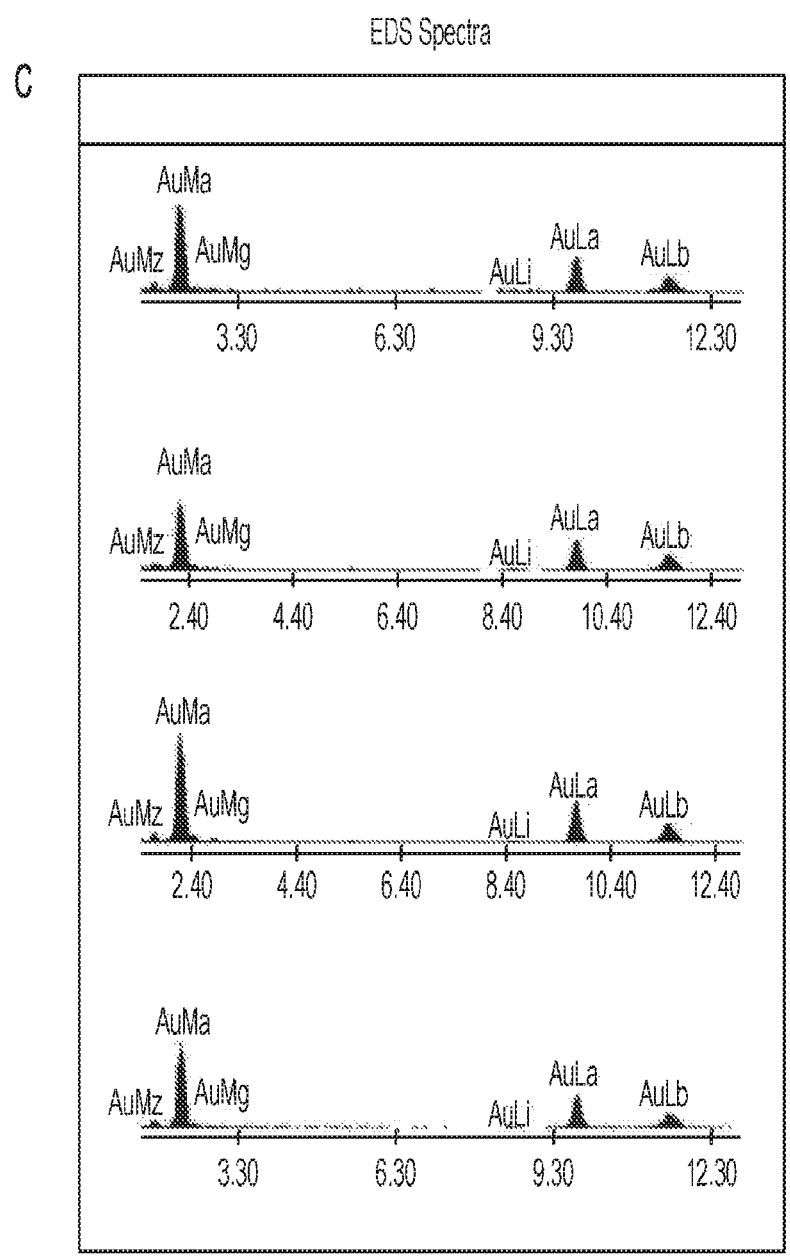

FIGS. 25A-25C further show that shape-controlled synthesis of gold nanoparticles can be performed without surfactants.

FIG. 25A shows synthesis of various morphologies from the same batch of 3.5 nm gold nanoparticle seeds. Nanostars form under the fastest rates of $HAuCl_4$ reduction, followed by nanospheres, nanorods, and nanoplates as the reduction rate decreases. The size of all shapes can be tuned by adjusting the $HAuCl_4$:Seeds ratio.

FIG. 25B shows that nanostars, nanospheres, nanorods, and nanoplates synthesized under optimized conditions. While nanostars and nanospheres form virtually quantitatively, the nanorods and nanoplates require post-synthetic separation. Scale bars for nanoplates in (FIG. 25A) are 500 nm; all other scale bars are 100 nm.

FIG. 25C show energy dispersive x-ray scattering (EDS) spectra of (top to bottom) nanostars, nanospheres, nanorods, and nanoplates.

Figure 26A:
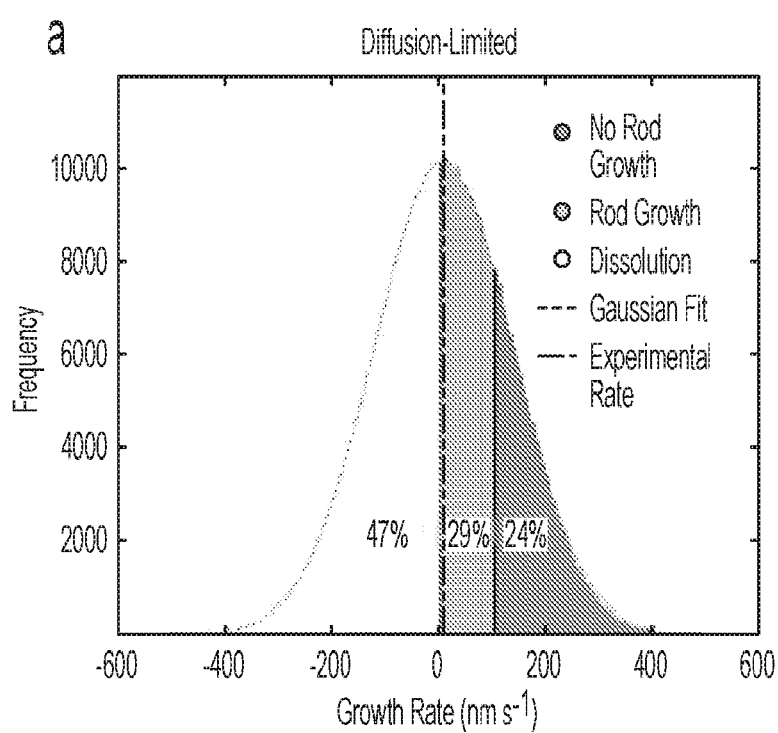
Figure 26B:
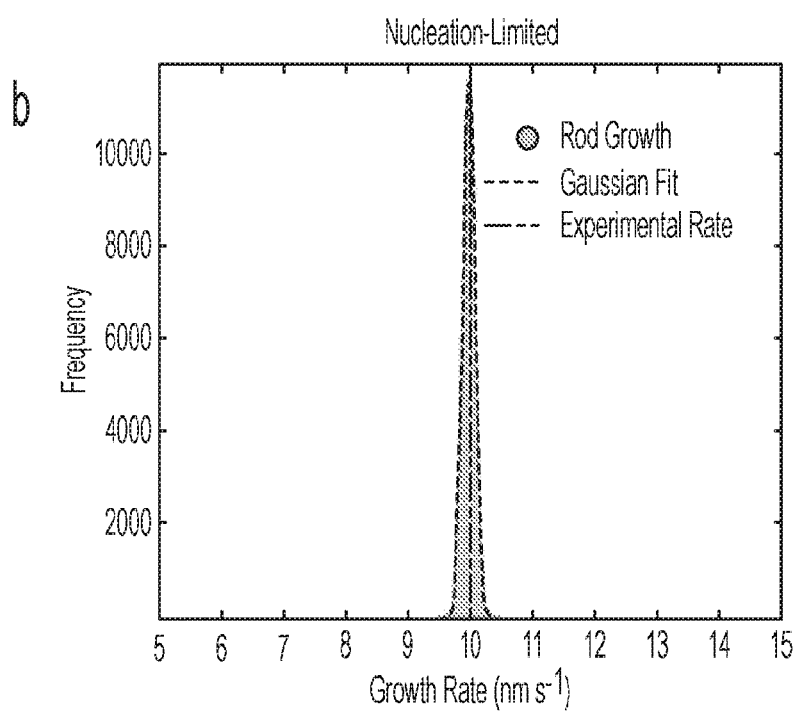
Figure 26C:
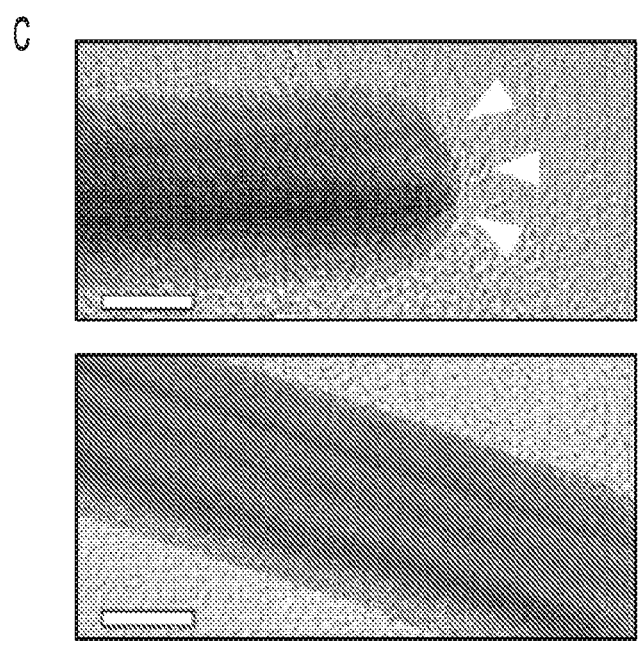

FIGS. 26A-26C show a growth mechanism analysis for gold nanorods.

FIG. 26A shows a simulated growth rate distribution of nanorods in the diffusion-limited regime. The diffusion-limited hypothesis yields a distribution of growth rates not observed experimentally, and incorrectly predicts that 47% of nanoparticles dissolve while 24% grow at a rate too fast to form nanorods.

FIG. 26B shows a simulated growth rate distribution of nanorods in nucleation-limited regime. The nucleation-limited hypothesis yields accurate predictions of distributions tightly centered about the experimentally observed growth rate.

FIG. 26C shows high-resolution transmission electron micrographs (HRTEM) of gold nanorods. The end facets exhibit re-entrant grooves, while the side facets are stepped, but relatively smooth by comparison. The grooves are known to catalyze monolayer nucleation, which, in some embodiments, explains the faster nucleation rate on the {111} facets.

Figure 26D:
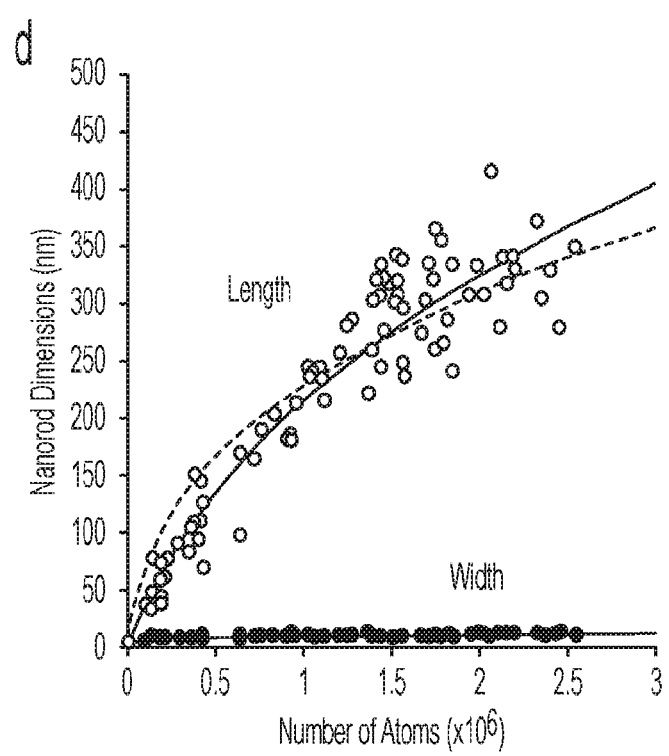

FIG. 26D shows an experimental length and width of nanoparticles fit to nucleation-limited growth. The curves are the best theoretical fits for anisotropic growth starting from a 4 nm seed (dashed line) and a 7.5 nm seed (solid line). The best fit to data occurs for a seed that begins growing into a rod once it reaches 7.5 nm in diameter.

Figure 27:
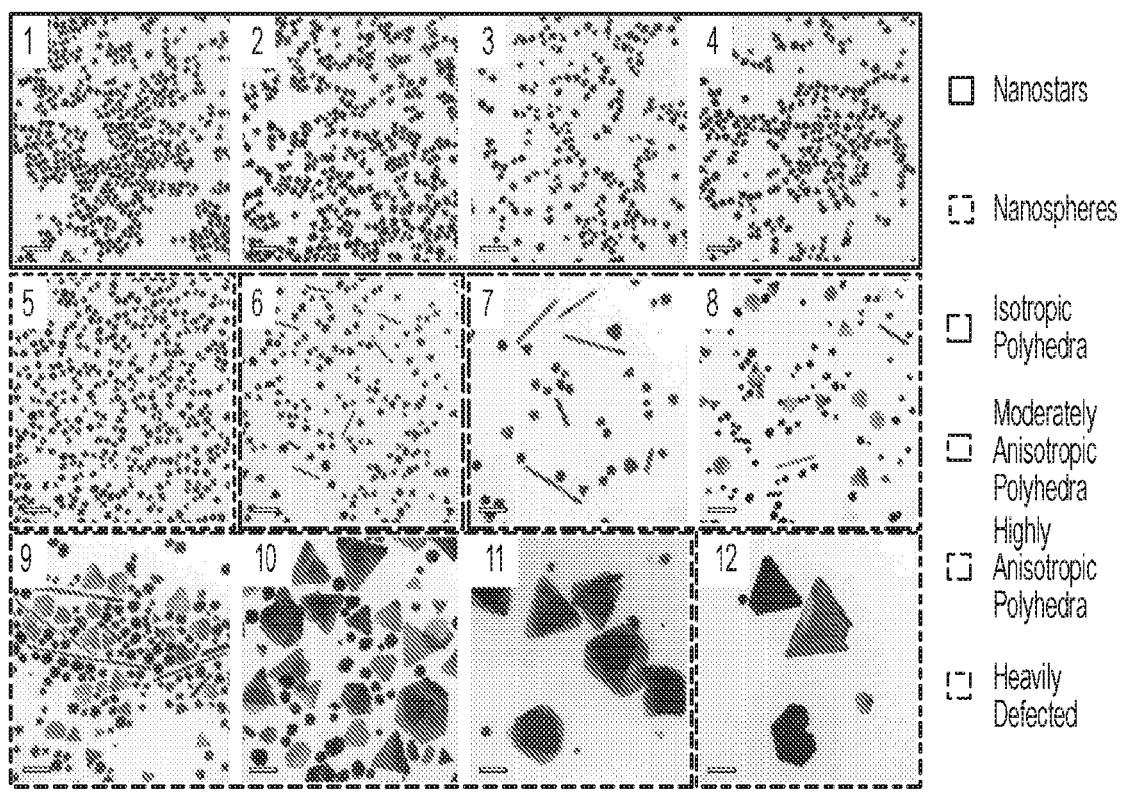

FIG. 27 shows changes in crystal growth as a function of growth rate. The twelve TEM images correspond to decreasing reduction rates of $HAuCl_4$. All reactions have the same concentration of seeds and $HAuCl_4$, such that the only synthetic variables are the amount of $H_2O_2$ and NaOH in solution. Panels 1-6 have 19.6 mM $H_2O_2$ and NaOH concentrations decreasing from 3.9 mM to 0.49 mM. Panels 7-12 have no NaOH, and $H_2O_2$ concentrations decreasing from $9.8 \times 10^{-1}$ M to $4.9 \times 10^{-8}$ M. The dominant type of products observed changes as labeled from nanostars in panel 1 to heavily defected nanoparticles in panel 12.

Figure 28:
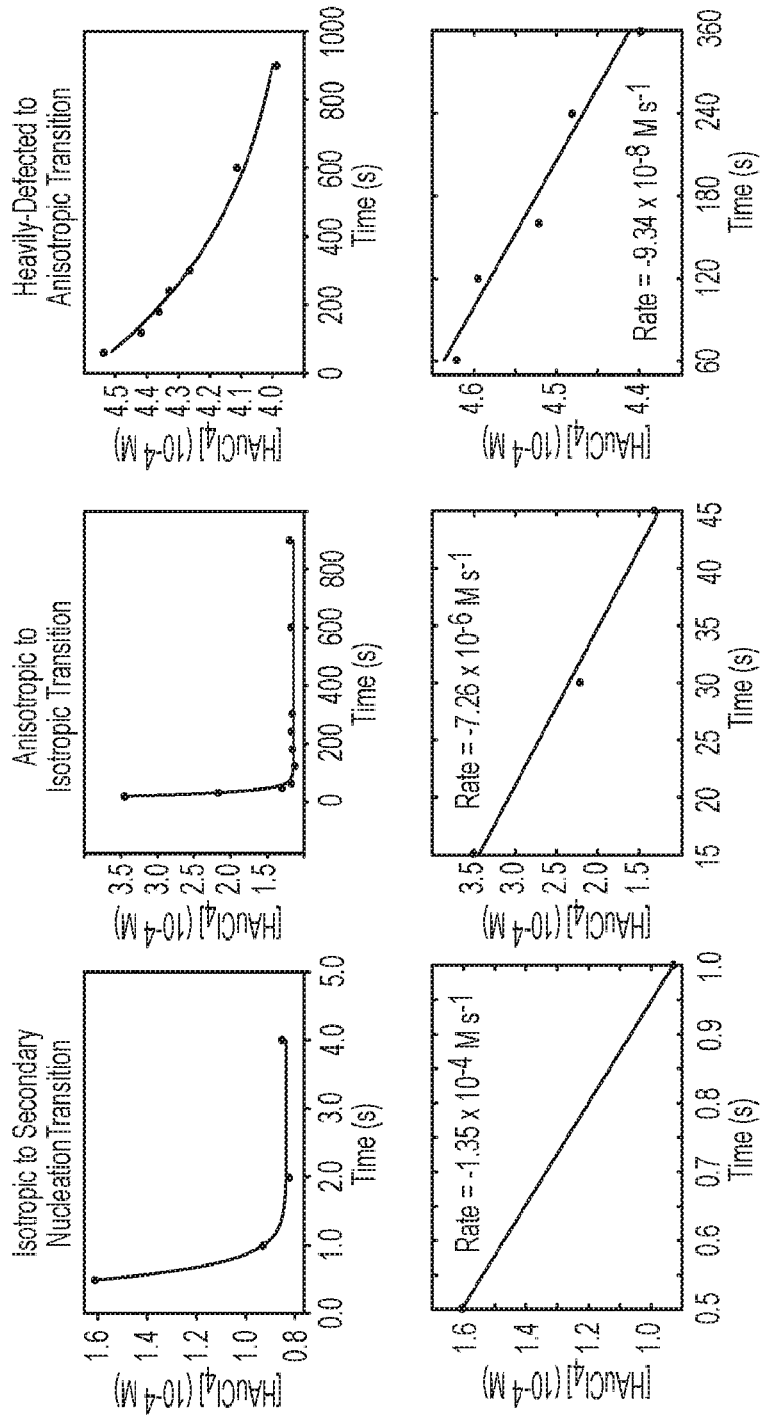

FIG. 28 shows kinetics of $HAuCl_4$ reduction. The absorbance of Au(III) was monitored by UV-visible spectroscopy at 300 nm. Representative syntheses were performed from which aliquots were removed at the measured time points and added to an equal volume of a 2% polyvinylpyrrolidone (PVP; 10 kDa) quenching solution. All measurements, including calibration curves, were performed on the same well plate. The rates refer to the disappearance of $HAuCl_4$ over time.

Figure 29:
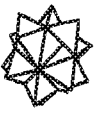
Figure 29:
Figure 29:
Figure 29:
Figure 29:
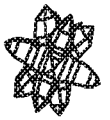
Figure 29:
Figure 29:
Figure 29:
Figure 29:
Figure 29:
Figure 29:
Figure 29:
Figure 29:
Figure 29:

FIG. 29 shows exemplary criteria for shape control in surfactant-free syntheses. Each product morphology forms from one or more corresponding seeds. All types of seeds (e.g. icosahedral, five-fold twinned, plate-like, etc.) can grow into spheres and stars if the reduction rate of $HAuCl_4^-$ is sufficiently fast. The polyhedral shapes (e.g. icosahedra, decahedra, rods, plates) can only be formed in high yield if the unique corresponding seed is present in high yield. Nanorod formation has the additional requirement that the seed possess re-entrant grooves (highlighted in red on five-fold seed) on the {111} facets. The reduction rates necessary to synthesize each shape are given in the last column.

FIGS. 30A-30F shows tunability of nanostars.

FIG. 30A shows that the $HAuCl_4$ reduction kinetics increase, protrusions begin to grow outward from the nanoparticle core. The aspect ratio of the protrusions increases until an optimum is reached, beyond which the aspect ratio decreases and the number of protrusions increases.

FIG. 30B shows a TEM image of characteristic nanostars formed under the minimal reaction rate sufficient to produce stable nanostars in high yield (1.0 mM/s).

FIG. 30C shows a TEM image of characteristic nanostars formed under the fastest reaction kinetics tested shows that the number of protrusions increases and their aspect ratio decreases relative to the nanostars formed under slower kinetics.

FIGS. 30D-30F show nanostars grown from different seed diameters. The average number of protrusions per particle increases while maintaining the same total diameter as the seed size is increased from (FIG. 30D) 5 nm, to (FIG. 30E) 15 nm, to (FIG. 30F) 33 nm. Scale bars are 50 nm in FIGS. 30B-30C, and 100 nm in FIGS. 30A-30F.

FIGS. 31A-31D show nanostar transformation and stabilization.

Figure 31A:
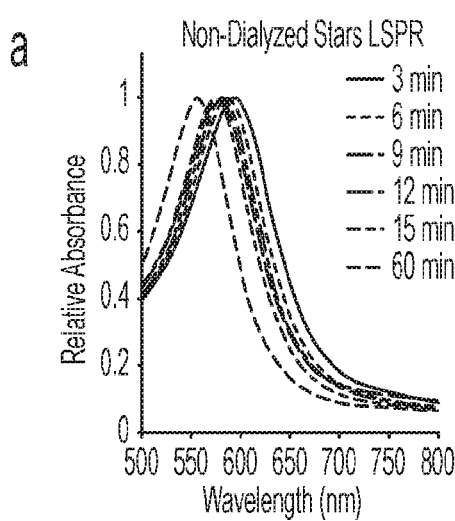

FIG. 31A shows absorbance spectra of as-synthesized gold nanostars that were not subjected to post-processing measured at the indicated time points.

Figure 31B:
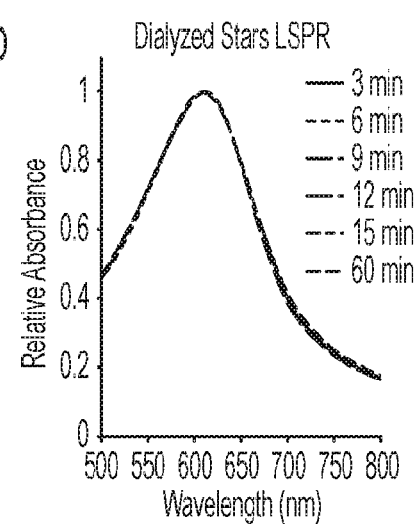

FIG. 31B shows absorbance spectra of as-synthesized gold nanostars that were immediately dialyzed to remove residual reagents measured at the indicated time points.

Figure 31C:
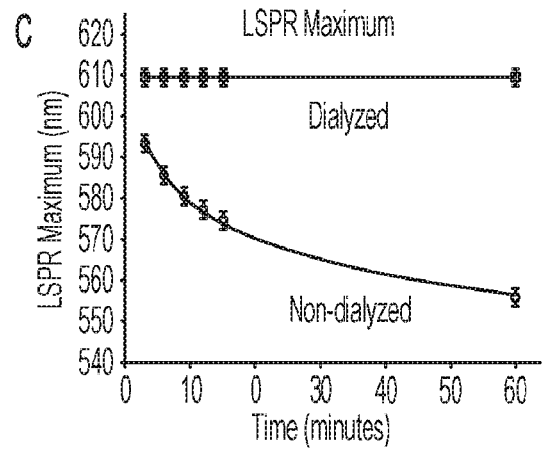

FIG. 31C shows localized surface plasmon resonance (LSPR) maximum plotted against time. No shift was observed for the dialyzed gold nanostars, while the absorbance maximum of non-dialyzed gold nanostars rapidly red-shifted over time approaching 540 nm (LSPR of spherical gold nanoparticles).

Figure 31D:
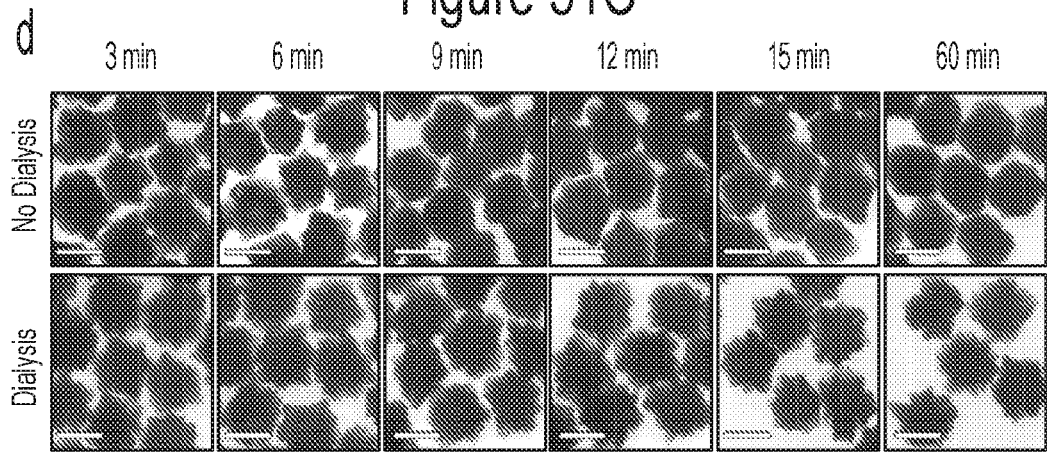

FIG. 31D shows TEM images that demonstrate spherical transformation of the non-dialyzed gold nanostars over time, and that the star-shape of the dialyzed gold nanostars was preserved. Scale bars are 50 nm.

FIGS. 32A-32F shows exemplary evidence for five-fold structure of gold nanorods produced by the $H_2O_2$-mediated synthesis.

Figure 32A:
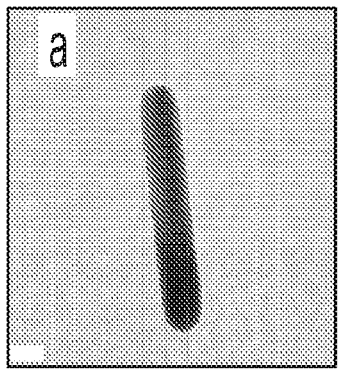

FIG. 32A shows a HRTEM of gold nanorod prepared by approaches described herein.

Figure 32B:
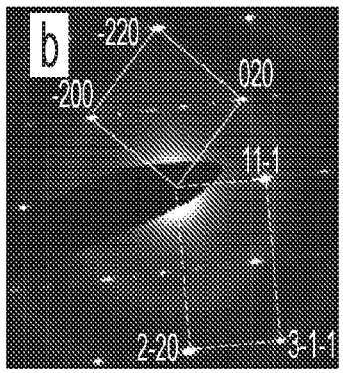

FIG. 32B shows an electron diffraction pattern of nanorod in (FIG. 32A) demonstrating a superposition of [100] and [112] contributions.

Figure 32C:
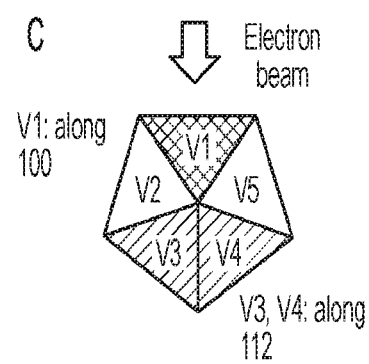

FIG. 32C shows that an electron beam is incident upon the nanorod as depicted in the schematic.

Figure 32D:
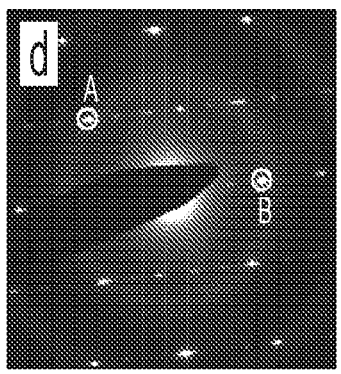

FIG. 32D shows a Selected Area Electron diffraction pattern of nanorod in (FIG. 32A). The point labeled A corresponds to the [100] orientation and the point labeled B corresponds to the [112] orientation.

Figure 32E:
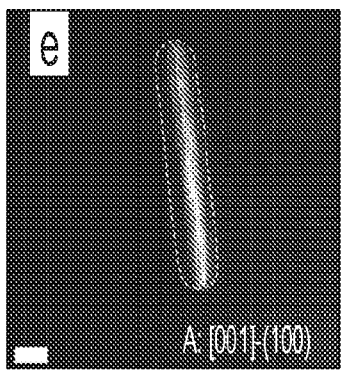

FIG. 32E shows a view along [100] produces strong contrast confined near the central axis of the rod, as expected from cross-section of the V1 tetrahedral subunit of the five-fold twinned structure. Dashed outline is included for clarity.

Figure 32F:
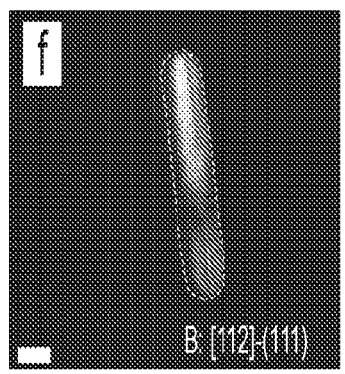

FIG. 32F show a view along [112] produces strong contrast throughout the nanorod, as expected from the combined V3 and V4 tetrahedral subunits. These results provide strong evidence of the five-fold twin nanorod structure. Scale bar in (FIG. 32A) is 10 nm.

Figure 33A:
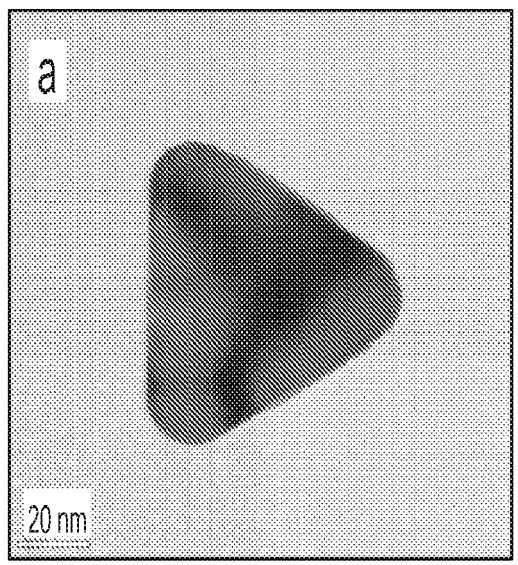
Figure 33B:
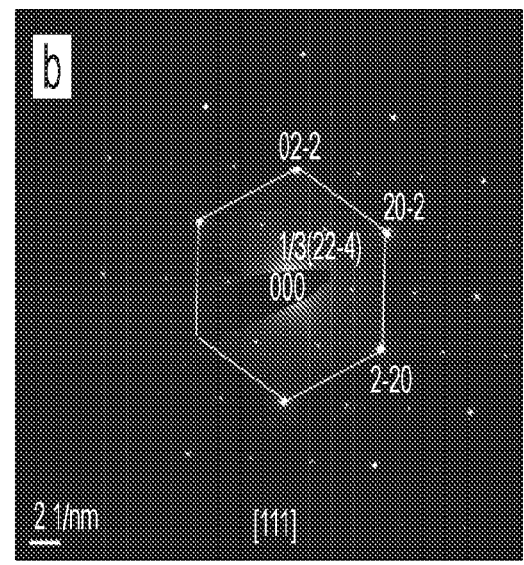

FIGS. 33A and 33B show electron diffraction of gold nanoplates. Electron diffraction analysis of the nanoplates reveals a forbidden 1/3{$22\bar{4}$} reflection, indicating the presence of twin planes parallel to the top and bottom {111} facets. The electron diffraction pattern in FIG. 33B corresponds to the nanoplate shown in FIG. 33A. Several plates were analyzed and all demonstrated the forbidden reflection.

FIGS. 34A-34E show growth unit incorporation at the step front.

Figure 34A:
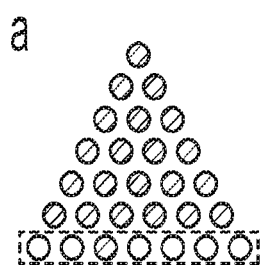

FIG. 34A shows 1D nucleation at the edge of a triangular partial monolayer. The filled and unfilled circles represent occupied and unoccupied sites, respectively.

Figure 34B:
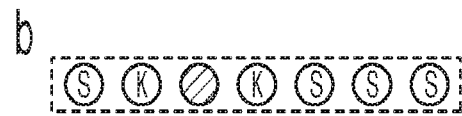

FIG. 34B shows an expanded view of the incomplete step in FIG. 34A. The sites labeled "k" are kink binding sites and those labeled "s" are non-kink step sites. The variables "m" and "n" are highlighted, which respectively denote the total number of sites in a step and the number of sites in the largest unfilled fragment.

Figure 34C:
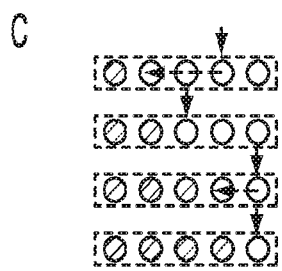

FIG. 34C shows an exemplary Mechanism 1—Step adsorption and diffusion to kink. Growth units jump into the step (blue arrows) at random locations and diffuse along the step (red arrows) until they bind at the kink site. The non-kink step sites are modeled as a continuous time Markov chain to determine the expected time of step diffusion to the kink binding site.

Figure 34D:
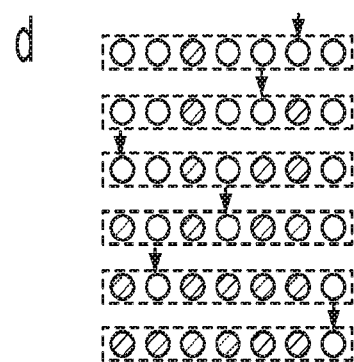

FIG. 34D shows an exemplary Mechanism 2—Direct step incorporation. In contrast to Mechanism 1, this Mechanism 2 does not involve step diffusion. Mechanism 2 operates when the rate of step diffusion is slower than the rate of additional growth unit arrivals into the step sites.

Figure 34E:
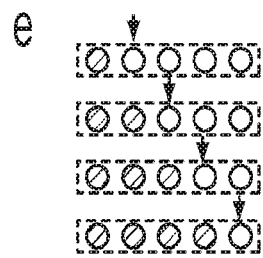

FIG. 34E shows an exemplary Mechanism 3—Direct kink incorporation. Similar to Mechanism 2, Mechanism 3 does not involve step diffusion. In contrast to mechanisms 1 and 2, growth by Mechanism 3 occurs exclusively by jumps from the terrace to kink binding sites. This mechanism operates when the rate of step diffusion is slower than the rate of additional growth unit arrivals and the activation energy for jumping into kink sites is significantly lower than for jumping into non-kink step sites.

DETAILED DESCRIPTION OF CERTAIN EMBODIMENTS

In general, the present invention provides technologies for preparing nanoparticle compositions. Embodiments of the present disclosure provide nanoparticle compositions, methods of preparing them, reagents for preparing them, methods of using them, etc. In particular, the present invention provides "green chemistry" technologies, characterized by their use of environmentally benign reagents. Furthermore, in some embodiments, the present invention provides systems of reagents characterized in that the same set of reagents can be used to prepare nanoparticle cores of a variety of different shapes through simple variation of reaction conditions; the present invention also provides a set of guiding principles for matching such reaction conditions to the shapes that they produce, so that appropriate conditions can be selected for any application of interest.

Alternatively or additionally, the present invention provides technologies for preparing nanoparticle compositions of differentially detectable nanoparticles—either due to differently shaped cores, differential presence or thickness of one or more coating layers, or both. Those of ordinary skill in the art, reading the present disclosure, will immediately appreciate a variety of valuable uses for such compositions, including in the simultaneous or sequential detection of a plurality of targets in a single sample, source, or site.

I. Nanoparticle Compositions

In general, nanoparticles according to the present invention comprise a metallic core, and optionally comprise one or more coating layers, surface-associated entities and/or one or more dopant entities. In some embodiments, nanoparticles as prepared and/or used herein do not include any coatings, surface-associated entities and/or dopants. Thus, in some embodiments, nanoparticles as prepared and/or utilized herein comprise or consist of anisotropic metal cores (e.g., anisotropic gold cores).

IA. Cores

Metallic nanoparticle cores prepared and/or utilized in accordance with the present invention are typically comprised of a metal selected from the group consisting of gold, palladium, platinum, silver, and/or other metals capable of presenting a face-centered cubic structure and platinum; in some embodiments, metallic nanoparticle cores are comprised of gold. In some embodiments, metallic nanoparticle cores consist of gold.

Those skilled in the art are well aware that the shape of a nanoparticle core can profoundly impact, or even determine, key properties of the nanoparticle including, for example, optical, physical, and/or chemical properties. In some embodiments of the present invention, metallic nanoparticles have a core shape selected from the group consisting of, cages, cones, cylinders, cubes cuboids, hexagons, icosahedra, octahedra, plates, prisms, pyramids, rings, rods, shells, spheres, stars, tetrahedra, etc. In some embodiments, relevant nanoparticle core shapes are discs, plates, rods, spheres, squares, or stars; in some embodiments, they are plates, rods, or stars.

IB. Layers

In some embodiments, nanoparticles provided by the present invention may include one or more layers coated on the core.

In some embodiments, a layer substantially covers at least one surface of the core (or of a preceding layer). In some such embodiments, a layer substantially encapsulates the core.

In some embodiments, adjacent layers are in direct physical contact with one another; in some embodiments, adjacent layers are separated from one another so that an inter-layer space is defined between them; in some embodiments, such an inter-layer space is empty; in some embodiments, such an inter-layer contains a liquid (or a combination of liquids), one or more dopant entities, etc.

Those of ordinary skill in the art will appreciate that a layer can have any of a variety of sizes or shapes (e.g., thicknesses). In some embodiments, a layer can be porous. In some embodiments, a layer is in a shape of a thin stripe or mat. In some embodiments, one or more layers substantially or partially cover the surface of the core, or of a preceding layer.

In some embodiments, layers are arranged as shells. As will be appreciated by those skilled in the art, at least two shells can be partially extended from at least one substrate (e.g., core), concentrically extended from at least one substrate, or extended asymmetrically from at least one substrate. In some embodiments, shells may have equal thicknesses; in some embodiments, shells may have different thicknesses.

A plurality of layers each can respectively contain or be comprised of one or more materials. Layers (e.g., shells) can be or comprise, but are not limited to, one and the same material (e.g., consisting of, but not limited to, compounds/materials from the group of metal/semi-metal/non-metal, -oxides, -sulfides, -carbides, -nitrides, polymers (which optionally may be biodegradable), (poly)peptides, nucleic acids (e.g., DNA), and any combination thereof); layers can consist of at least two different materials; different layers can consist of the same or different materials in any combination.

In some embodiments, a layer is synthesized by reacting precursors, and the resulting layer is a condensation layer. Nanoparticles described herein, in some embodiments, comprise at least a condensation layer and at least another layer, which can be another condensation layer or any other layers.

According to various embodiments of the present disclosure, a layer can be or comprise metal (e.g., gold, silver, and the like), semi-metal or non-metal, and metal/semi-metal/non-metal oxides including silica ($SiO_2$), titania ($TiO_2$), alumina ($Al_2O_3$), zirconia ($ZrO_2$), germania ($GeO_2$), tantalum pentoxide ($Ta_2O_5$), $NbO_2$, etc., and non-oxides including metal/semi-metal/non-metal borides, carbides, sulfide and nitrides, such as titanium and its combinations (Ti, $TiB_2$, TiC, TiN, etc.).

Additionally or alternatively, materials of a layer can be selected from polymers, including PEG and PLGA/PEG, polymeric chelators (e.g., poly DOTA, dendrimer backbone, poly DTPA, or dendrimer alone), carbon nanotubes (which may be multiwalled in some embodiments), graphene, silicone, peptides, nucleic acids, and any combination thereof.

In some embodiments, a layer is or includes silica. For example, a silica layer can be synthesized from a silica precursor including, but not limited to, alkylalkoxysilane; ethylpolysilicate; tetraethylorthosilicate (TEOS); tetramethylorthosilicate (TMOS); partially hydrolyzed TEOS; partially hydrolyzed TMOS or a combination thereof.

In some embodiments, a layer is or includes one or more polymers, particularly polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1, 3-dioxan-2-one)); polyanhydrides (e.g., poly(sebacic anhydride)); polyethers (e.g., polyethylene glycol); polyurethanes; polymethacrylates; polyacrylates; polycyanoacrylates; copolymers of PEG, poly(ethylene oxide) (PEO), and any combination thereof.

In some embodiments, a layer is or includes at least one degradable material. Such a degradable material can be hydrolytically degradable, biodegradable, thermally degradable, enzymatically degradable, and/or photolytically degradable polyelectrolytes. In some embodiments, degradation may enable release of one or more dopant entities (e.g., agent for delivery) associated with a nanoparticle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In general, any layer within a nanoparticle described herein can have a thickness (e.g., an average thickness) independent of that of any other layer. In some embodiments, a layer may have a thickness within a specified range. In some embodiments, some or all layers have the same thickness or have thicknesses within the same range. In some embodiments, layers on a given nanoparticle may alternate thicknesses (e.g., layers of one thickness may alternate with layers of a different thickness).

In some embodiments, a layer has an average thickness that is about or less than a thickness selected from the group consisting of 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, a layer has an average thickness within a range between a lower limit and an upper limit, wherein the lower limit is selected from the group consisting of 0.1 nm, 0.5 nm, 1 nm, 5 nm, 10 nm, 15 nm, 20 nm, 30 nm, 40 nm, 50 nm, 60 nm, 70 nm, 80 nm, 90 nm, 100 nm, 200 nm, 300 nm, 400 nm, 500 nm, 800 nm and 1 µm, the upper limit is selected from the group consisting of 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, and 0.5 nm, and the upper limit is greater than the lower limit. In some embodiments, a layer has a thickness within a range of between about 0.1 nm and about 5 µm, about 0.5 nm and about 200 nm, about 5 nm and about 50 nm or about 10 nm and about 30 nm.

In some embodiments, a layer can have or be modified to have one or more functional groups. Such functional groups (within or on a layer's surface) can be used for association with any agents (e.g., detectable entities, targeting entities, or PEG). Such associated agents can be dopant entities, if associated (e.g., doped) within layers. For example, targeting entities and/or PEG can be associated within one or more layers comprising degradable polymers. When the degradable polymers degrade, the dopant entities can be exposed.

In some embodiments, part or all of the surface of an outer-most layer can be modified, for example to add and/or modify functional groups present on the outer-most layer. To give but a few examples, reagents such as, but not limited to, mercaptosilanols or aminosilanols can be used to introduce sulfhydryl or amine groups, respectively, to silica, tantalia, etc.; catechol-amines can be used to introduce cationic amine-functionality to titania, etc. Alternatively or additionally, hydrogen peroxide can be utilized to oxidize sulfhydryl-groups (including introduced sulfhydryl groups) to generate anionic sulfonate-functionality can further chemically alter the introduced groups.

Those of ordinary skill in the art will appreciate that, in some embodiments, such strategies may modify surface charge of nanoparticles. Alternatively or additionally, such strategies may introduce functional groups that, for example, allow conjugation of linkers (e.g., (cleavable or (bio-)degradable) polymers such as, but not limited to, polyethylene glycol, polypropylene glycol, PLGA, etc.), targeting/homing agents (e.g., such as, but not limited to, small molecules (e.g., folates, dyes, etc.), (poly)peptides (e.g., RGD, epidermal growth factor, chlorotoxin, etc.), antibodies, proteins, etc.), contrast/imaging agents (e.g., fluorescent dyes, (chelated) radioisotopes (SPECT, PET), MR-active agents, CT-agents), therapeutic agents (e.g., small molecule drugs, therapeutic (poly)peptides, therapeutic antibodies, (chelated) radioisotopes, etc.), or combinations thereof, to nanoparticle surfaces.

IC. Surface-Associated Entities

In some embodiments, nanoparticles may have one or more surface-associated entities such as stabilizing entities, targeting entities, etc. In some embodiments, such surface-associated entities are or are comprised in a layer as discussed herein. In some embodiments, such entities are associated with or attached to a core; in some embodiments, such entities are associated with or attached to a layer.

In fact, in some embodiments, the present invention identifies the source of a problem with existing nanoparticle systems that utilize or include surface-associated entities in that limitations are often present in range of entities that can be caused to associate with a nanoparticle surface (e.g., a nanoparticle core surface) after preparation because many preparation technologies leave surfaces associated with agents or moieties that participate in and/or are required for the synthesis. These synthesis-related agents or moieties must be displaced in order to associate the surface with any other entity. Thus, the range of entities that can be caused to associate with nanoparticle surfaces, in many instances, is limited to those with sufficient affinity and other characteristics to displace the synthesis-related agents or moieties.

For example, in some embodiments it may be desirable to associate one or more of 1) targeting agents or moieties; 2) therapeutic agents or moieties; 3) detectable agents or moieties; 4) immune-modifying (e.g., immune avoiding, immune suppressing, immune stimulating, or immune activating) agents or moieties; 5) stabilizing agents or moieties with nanoparticle surfaces (see, for instance, gold particles provided by CytImmune Sciences Inc. which are said to have 1) tumor-targeting molecules, 2) immune-avoiding molecules; and 3) therapeutic molecules associated with their surface. In certain embodiments, any or all such agents may be associated with surfaces of provided nanoparticles, and indeed the range of particular compounds that may be utilized with provided nanoparticles is significantly greater than the particular ones described by CytImmune Sciences Inc. or others). In some embodiments, surface associated agents included in nanoparticle compositions or otherwise utilized in accordance with the present invention are non-immunogenic as utilized; in some such embodiments, such agents are non-immunogenic in that they do not induce in a subject (e.g., a human subject) to whom they are administered a harmful immune reaction.

ID. Dopant Entities

In accordance with many embodiments of the present disclosure, dopant entities can be associated with nanoparticles, for example through association with nanoparticle core surfaces, one or more layers or one and/or more inter-layer spaces. In some embodiments, dopant entities are attached directly or indirectly to a nanoparticle core, or to one or more layers. In some embodiments, dopant entities are distributed within one or more layers; in some embodiments, dopant entities are discretely localized within one or more layers.

In general, any entity of interest can be utilized as a dopant entity in accordance with the present invention. In some embodiments, a dopant entity is or comprises a detectable entity such as, for example, an entity selected from the group consisting of computed tomography (CT) agents, fluorochromes (e.g., near infrared (metal-enhanced) fluorescence agents, 2-photon fluorescence agents, etc. such as Alexa 647, Alexa 488 and the like), (laser) pumping materials (e.g., consisting of, but not limited to, materials from the group of the rare-earth metal- and/or transition metal-based compounds), luminescent compounds, MRI agents (e.g., consisting of, but not limited to, rare-earth metals and/or transition metals such as gadolinium, manganese, iron(-oxides)), photoacoustic-active dyes, positron emission tomography (PET) tracers (e.g., $^{18}$F, $^{64}$Cu, $^{11}$C, $^{13}$N, $^{15}$O, and the like), radio nuclides (e.g., alpha-emitting radionuclides (e.g., At-211, Bi-212, Bi-213, Ra-223, and Ac-225), beta-emitting radionuclides (e.g., Cu-67, Y-90, Ag-111, I-131, Pm-149, Sm-153, Ho-166, Lu-177, Re-186, and Re-188), SE(R)RS-active agents, upconverting materials (e.g., consisting of materials from the group of the rare-earth metals and/or transition metals), single photon emission tomography (SPECT) tracers (e.g., $^{99}$Tc, $^{67}$Ga, $^{192}$Ir and the like), "slow light"-inducing materials (e.g., praseodymium-based compounds), ultrasound (US) agents, X-Rays agents, and any combination thereof.

SE(R)RS-Active Agents

In some embodiments, a dopant entity is or comprises a dye, for example, a resonance dye. A dopant entity can be or comprise an agent useful in Raman spectroscopy (e.g., SE(R)RS-active agents). Exemplary dopant entities include, but are not limited to, those agents described in the art such as in U.S. Pat. Nos. 5,306,403, 6,002,471, and 6,174,677, the contents of each of which is incorporated herein by reference in its entirety.

In some particular embodiments, a dopant entity is SE(R)RS- and/or photoacoustic active agent(s). In some particular embodiments, a high density of a SE(R)RS-active agent located close to a substrate contributes to unprecedented Raman sensitivity achieved by a particle described herein. SE(R)RS-active agents generally benefit from signal intensity enhancement in the proximity of a metal surface. In accordance with the present disclosure, a skilled artisan in the art would be capable to choose a particular SE(R)RS-active agent, to achieve chemical enhancement and/or electromagnetic enhancement, considering factors such as substrate materials, substrate configurations, layer material, etc. Such a SE(R)RS-active agent can have a charge transfer effect, from a metal to the molecule, or from the molecule to the metal.

A SE(R)RS-active agent refers to a molecule that is capable of generating a SERS or SE(R)RS spectrum when appropriately illuminated. Non-limiting examples of SE(R)RS-active agents include phthalocyanines such as methyl, nitrosyl, sulphonyl and amino phthalocyanines, naphthalocyanines, chalcogen-based dyes, azomethines, cyanines, squaraines, and xanthines such as the methyl, nitro, sulphano and amino derivatives. Each of these may be substituted in any conventional manner, giving rise to a large number of useful labels. It is noted that the choice of a SE(R)RS-active agent can be influenced by factors such as the resonance frequency of the molecule, the resonance frequency of other molecules present in a sample, etc.

Typically, detecting a SE(R)RS signal involves using incident light from a laser. The exact frequency chosen will depend on the SE(R)RS-active agent, and metal surface. Frequencies in visible or near-infrared spectrum tend, on the whole, to give rise to better surface enhancement effects for noble metal surfaces such as silver and gold. However, it is possible to envisage situations in which other frequencies, for instance in the ultraviolet range might be used. The selection and, if necessary, tuning of an appropriate light source, with an appropriate frequency and power, will be well within the capabilities of one of ordinary skill in the art, particularly with reference to the available SE(R)RS literature.

The Raman enhancement generally is proportional to the density of a SE(R)RS-active agent associated (e.g., adsorbed) on a metal surface. A surprisingly high density of a SE(R)RS-active agent adsorbed on a substrate surface in accordance with the present disclosure may contribute to the superior sensitivity of particles disclosed herein.

Fluorescent Agents

In some embodiments, a dopant entity is or comprises a fluorescent dye/agent (e.g., near infrared (NIR) fluorescent dye). For example, fluorescent dyes/agents including, but not limited to, polymethines, cyanines, (na)phthalocyanines, porphorines, merocyanines, (pe)rylene (bisimides), squaraines, anthocyanins, phycocyanins, bodipys, rotaxanes, rhodamines, certain organometallic complexes, and any combination thereof can be used in accordance with the present invention.

MRI Agents

In some embodiments, a dopant entity is or comprises an MRI agent. In some embodiments, the amount or number of MRI agents associated with a layer can be about 1 to 10,000,000 MRI agents or about 5000 to 500,000 MRI agents. For additional information regarding the identity and quantity of MRI agent, see U.S. Patent Application Publication No. 2012/0179029, which is incorporated herein by reference in its entirety.

In some embodiments, MRI agent can include Gd(-salts), iron oxide, paramagnetic chemical exchange saturation transfer (CEST) agents, $^{19}$F active materials, manganese, melanin, or a substance that shortens or elongates T1 or T2 and a combination thereof. In certain embodiments, a Gd MRI agent can be a compound such as DOTA-Gd, DTPA-Gd, Gd within a polymeric chelator, and Gd immobilized by negative charges on a layer. In certain embodiments, an iron oxide MRI agent can be a compound such as a small paramagnetic iron oxide (SPIO) or an ultrasmall SPIO with or without a dextran or other stabilizing layer. In certain embodiments, a paramagnetic CEST MRI agent can be a compound such as lanthanide complexes.

In some embodiments, MRI agents can be linked to a layer via a linkage such as a maleimide linkage, NHS ester, click chemistry, or another covalent or non-covalent approach or a combination thereof. In some embodiments, MRI agents can also be loaded without addition of any exogenous agent, i.e., only layer(s) and MRI agent(s).

Alternatively or additionally, particles described herein can be prepared with dopant entities that are agents intended for administration or delivery. In some embodiments, such an agent remains associated with the particle after administration of the particle; in some embodiments, such an agent is released or otherwise dissociated from the particle after administration.

Alternatively or additionally, in some embodiments, a doping entity may be or comprise one or more therapeutic agents (e.g., such as a small molecule-, chelate-, peptide-, protein-, antibody, RNA, DNA, aptamer-based compounds/material (right), or any combination thereof). For example, dopant entities may be or comprise any therapeutic agents (e.g., antibiotics, NSAIDs, angiogenesis inhibitors, neuroprotective agents), cytotoxic agents, diagnostic agents (e.g., contrast agents; radionuclides; and fluorescent, luminescent, and magnetic moieties), targeting agents, prophylactic agents (e.g., vaccines), and/or nutraceutical agents (e.g., vitamins, minerals, etc.), or other substances (e.g., salt) that may be suitable for introduction to biological tissues, including pharmaceutical excipients and substances for cosmetics, and the like.

Certain representative therapeutic agents are selected from the group consisting of amino acids, vaccines, antiviral agents, nucleic acids (e.g., siRNA, RNAi, and microRNA agents), gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, vitamins and/or any combination thereof. In some embodiments, an agent may be selected from suitable proteins, peptides and fragments thereof, which can be naturally occurring, synthesized or recombinantly produced.

In some embodiments, a therapeutic agent is or comprises a biologic. Examples of biologics including, but are not limited to, monoclonal antibodies, single chain antibodies, aptamers, enzymes, growth factors, hormones, fusion proteins, cytokines, therapeutic enzymes, recombinant vaccines, blood factors, and anticoagulants. Exemplary biologics suitable for use in accordance with the present disclosure are discussed in S. Aggarwal, *Nature Biotechnology*, 28:11, 2010, the contents of which are incorporated by reference herein in their entirety.

In some embodiments, a therapeutic agent is a small molecule and/or organic compound with pharmaceutical activity. In some embodiments, a therapeutic agent is a clinically-used drug. In some embodiments, a therapeutic agent is or comprises an anti-cancer agent, antibiotic, antiviral agent, anesthetic, anticoagulant, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc., or any combination thereof.

Exemplary anticancer agents included, but are not limited to, a cytokine, a chemokine, a growth factor, a photosensitizing agent, a toxin, an anti-cancer antibiotic, a chemotherapeutic compound, a radionuclide, an angiogenesis inhibitor, a signaling modulator, an anti-metabolite, an anti-cancer vaccine, an anti-cancer oligopeptide, a mitosis inhibitor protein, an antimitotic oligopeptide, an anti-cancer antibody, an anti-cancer agent, antibiotic, an immunotherapeutic agent, hyperthermia or hyperthermia therapy, a bacterium, radiation therapy, and any combination of such agents. In some examples, an anticancer agent is cisplatin, carboplatin, gemcitabine, irinotecan, an anti-EGFR antibody, an anti-VEGF antibody, and any combinations thereof.

A therapeutic agent used in accordance with the present application can be or comprise an agent useful in combating inflammation and/or infection. A therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof. Other anti-microbial agents such as copper may also be used in accordance with the present invention. For example, anti-viral agents, anti-protazoal agents, anti-parasitic agents, etc. may be of use. Additionally or alternatively, a therapeutic agent may be an anti-inflammatory agent.

A therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may a therapeutic gene as known in the art. In some embodiments, a therapeutic agent is a non-viral vector. Typical non-viral gene delivery vectors comprise DNA (e.g., plasmid DNA produced in bacteria) or RNA. In certain embodiments, a non-viral vector is used in accordance with the present invention with the aid of a delivery vehicle. In some embodiments, delivery vehicles may be based around lipids (e.g., liposomes) which fuse with cell membranes releasing a nucleic acid into the cytoplasm of the cell. Alternatively or alternatively, peptides or polymers may be used to form complexes (e.g., in form of particles) with a nucleic acid which may condense as well as protect the therapeutic activity as it attempts to reach a target destination.

Still further alternatively or additionally, in some embodiments, a dopant entity is or comprises a targeting agent. An agent can be a targeting agent (e.g., a chemical or biological agent) having an affinity for a target, for example, in a living host, where the agent is associated with a nanoparticle (e.g., within a layer of the particle or on the surface of a layer). In some embodiments, a nanoparticle can be used to image, detect, study, monitor, evaluate, and/or screen a disease, condition, or related biological event corresponding to the target.

In some embodiments, a targeting agent can function to cause a nanoparticle to interact with a target entity (e.g., molecule(s)). In some embodiments, a targeting agent can have an affinity for a cell, a tissue, a protein, DNA, RNA, an antibody, an antigen, and the like, that may be associated with a condition, disease, or related biological event, of interest. In some embodiments, a targeting agent can function to target specific DNA, RNA, and/or proteins of interest. In some embodiments, a targeting agent can be selected from the group consisting of polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, and any combinations thereof, for example that may have an affinity for a condition, disease, or related biological event or other chemical, biochemical, and/or biological events of the condition, disease, or biological event. In some embodiments, a targeting agent can include: sequence-specific DNA oligonucleotides, locked nucleic acids (LNA), and peptide nucleic acids (PNA), antibodies, small molecule protein receptors, and/or any combination thereof.

IE. Nanoparticles

Nanoparticles have a size (as determined by their longest dimension) that typically does not exceed about 10 μm. In some embodiments, nanoparticles are characterized by having at least one dimension that is about or less than a length selected from 10 μm, 5 μm, 1 μm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, nanoparticles are characterized by having a longest dimension that is about or less than a length selected from 10 μm, 5 μm, 1 μm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm.

In some embodiments, nanoparticles have a size within a range bounded by a lower limit that is about or more than a length selected from 1 nm, 2 nm, 5 nm, 10 nm, 20 nm, 30 nm, 40 nm, 50 nm, 60 nm, 70 nm, 80 nm, 90 nm, 100 nm, 110 nm, 120 nm, 150 nm, 180 nm, 200 nm, 300 nm, 400 nm, 500 nm, 800 nm, 1 μm, or 5 μm, and an upper limit that is about or less than a length selected from 10 μm, 5 μm, 1 μm, 800 nm, 500 nm, 400 nm, 300 nm, 200 nm, 180 nm, 150 nm, 120 nm, 110 nm, 90 nm, 80 nm, 70 nm, 60 nm, 50 nm, 40 nm, 30 nm, 20 nm, 10 nm, 5 nm, and 2 nm, the upper limit being larger than the lower limit.

In some embodiments, a nanoparticle has a shape that is the same as the shape of its core; in some embodiments, a nanoparticle has a shape different from that of its core (e.g., if it has a coating that comprises one or more layers whose thickness varies).

It will be appreciated by those skilled in the art that particular sizes and/or shapes of nanoparticles may be especially desirable or useful in particular contexts. For example, nanoparticles for in vivo applications typically have a size within a range from about 0.5 nm to about 200 nm; nanoparticles for in vitro applications often have a size within a range from about 10 nm to about 1000 nm.

In some embodiments, nanoparticle sizes and surface charges are tuned to be provided to sites of interest for particular applications. In many embodiments, a site of interest is or comprises a tumor. In some embodiments, nanoparticles are designed and constructed to enter tumors via their leaky vasculature. In some embodiments, nanoparticles are designed and constructed to enter and/or be retained in tumors via phagocytosis by tumor (associated) cells (known as "enhanced permeability and retention (EPR)" effect). In certain embodiments, nanoparticles do not wash out of a tumor, but are retained stably within the tumor (e.g., retention time at least 7 days).

IF. Nanoparticle Compositions Prepared by Provided Methodologies

As described herein, the present invention provides technologies that permit preparation of nanoparticle cores of particular geometries (e.g., anisotropic nanoparticle cores) using environmentally benign reagents. In many embodiments, provided technologies utilize only such environmentally benign reagents.

Further as described herein, the present invention provides technologies that permit preparation of nanoparticle cores of particular geometries (e.g., anisotropic nanoparticle cores) using etching technologies. By contrast, many available technologies for preparing shaped nanoparticle cores rely on surface blocking, and specifically utilize or require surface blocking agents such as surfactants, polymers, and underpotential deposition species (e.g., silver on gold), and/or nitrogen-, sulfur-, or phosphorus-containing species; many such surface blocking agents are toxic or at least not environmentally benign.

Still further as described herein, the present invention provides technologies that permit removal of undesired components (e.g., unreacted reagents) from nanoparticle compositions. In some embodiments, such removal is by dialysis and/or by washing. In some embodiments, no removal is required (e.g., because such components are never added to or included in nanoparticle core preparation reactions In some embodiments, the present invention provides nanoparticle compositions comprised of shaped nanoparticle cores and substantially free of toxic reagents. For example, in some embodiments, the present invention provides shaped nanoparticle cores in a composition comprised solely of environmentally benign components. In some embodiments, the present invention provides nanoparticle compositions comprised of shaped nanoparticle cores and substantially free of complex natural extracts and/or of toxic agents such as silver (Ag), dimethylformamide, ethylene glycol, cetyltrimethylammonium bromide (CTAB), and/or stabilizing polymers such as polyvinylpyrrolidone (PVP) (8-13). In many embodiments, provided nanoparticle compositions are substantially free of surfactants, polymers, and/or underpotential deposition species. In many embodiments, provided nanoparticle compositions are substantially free of CTAB. In some embodiments, provided nanoparticle compositions consist of nanoparticles (e.g., nanoparticle cores) and water. In some embodiments, provided nanoparticle compositions consist of nanoparticles and a solvent/suspension medium. In some embodiments, the solvent/suspension medium is a green solvent/medium in that it is substantially free of toxic components and/or contains only environmentally benign components IG. Differentially Detectable Nanoparticle Compositions As described herein, the present invention provides nanoparticle compositions comprising differentially detectable nanoparticle subsets. In some such embodiments, the differential detectability of different nanoparticle subsets arises from differently shaped cores, differential presence or thickness of one or more coating layers present on the cores, or both. Alternatively or additionally, in some such embodiments, differential detectability arises from presence or amount of one or more layers or doping agents.

II. Preparation of Nanoparticle Compositions

The present invention particularly provides novel technologies for preparation of nanoparticles with particularly-shaped (e.g., anisotropic) cores.

In general, the present invention provides technologies for seed-mediated synthesis of anisotropic metallic nanoparticle cores. In many embodiments, such synthesis is performed in the absence of any toxic chemical. Without wishing to be bound by any particular theory, the present invention proposes that such synthesis is achieved by precisely controlling the balance between growth and oxidative etching in hydrogen peroxide-mediated reduction reactions.

In some embodiments, the morphology of prepared anisotropic metallic nanoparticle cores is stabilized from transformation to more thermodynamically stable geometries by removal of residual reactants. In some embodiments, such removal is accomplished using one or more methodologies selected from the group consisting of washings, dialysis, and combinations thereof. In some embodiments, pure water dispersions are generated.

The present invention encompasses the recognition that synthesis reaction kinetics can be governed by reduction potential and by ratio of components in the synthesis reaction.

Some embodiments of the present invention involve combining metal seeds with a metal ion (e.g., in the form of a metal ion/counter ion pair, such as a metal chloride) in the presence of peroxide so that etching occurs on surfaces of the seeds and growth occurs through addition of the metal ion to the seeds. Depending on how fast growth is permitted to occur, differently shaped cores are prepared. As discussed in the Examples, the present invention provides guidelines for selecting component ratios and/or reaction rates in order to achieve preparation of any of a variety of anisotropic core shapes.

Different materials have different solubilities in a given solvent. Sugar, for example, is very soluble in water, which is why 93 g of sugar can be packed into a 24 oz. bottle of MOUNTAIN DEW®. In this case, the water molecules (i.e., the solvent) can form strong bonds with the sugar molecules, so a number of water molecules will form a shell around each sugar molecule. Because the sugar molecules have big water shells surrounding them, they no longer bond with other sugar molecules in solution. By definition, this process is described as the sugar molecules being dissolved by the water molecules.

If instead of sugar, a drop of oil were added into a bottle of water, the oil would just float around maintaining its droplet form. This is because the water-oil bonds are very weak and oil-oil bonds are very strong, so the water molecules are unable to form shells around the oil molecules. It is the formation of these shells that is responsible for dissolving a substance. Since the water shells never form around the oil molecules, the oil drop remains intact.

In order to understand nanoparticle synthesis, you need to think about the abovementioned phenomena in reverse. If you start with molecules that are very soluble in a solvent, like sugar in water, then perform a chemical reaction that makes them insoluble in the solvent (like oil molecules in water), the molecules (e.g., the sugar molecules that were previously soluble in water) will start to come together and bind with each other. If the reaction conditions are optimized, the molecules will keep binding with each other until the cluster of molecules reaches a size between 1 and 100 nanometers in diameter. These clusters are called nanoparticles.

For metal nanoparticle synthesis, metal salts are typically turned into metal atoms that cluster together into particles. The metal salts are very soluble in water, but the metal atoms are not. The most common chemical reaction that turns metal salts into metal atoms is called a reduction-oxidation or redox reaction. In this reaction, a reducing agent gives electrons to the positively-charged metal ion in the metal salt and turns it into a metal atom in a process called reduction. The opposite process, where a molecule takes electrons away from the metal atom to make it into a positively-charged metal ion is called oxidation. Reduction of metal salts creates metal atoms that cluster into metal nanoparticles. Oxidation of metal nanoparticles creates metal ions that dissolve into metal salts. These two processes have to be in perfect balance for a nanoparticle to remain stable. If there is too much reduction, the nanoparticle will continue to grow. If there is too much oxidation, the metal nanoparticle will dissolve.

Some molecules can perform both reduction and oxidation, which makes their chemistry quite complicated. A prototypical example is hydrogen peroxide, but it is not the only molecule with this ability. More commonly, many different chemical species will be present in a synthesis, some of which perform reduction and some of which perform oxidation. Most metal nanoparticle syntheses are set up this way. One way to control the size of a metal nanoparticle is to determine how to control/manipulate the degree of reduction and oxidation reactions, so that they balance out at a predetermined nanoparticle size.

Figure 15:
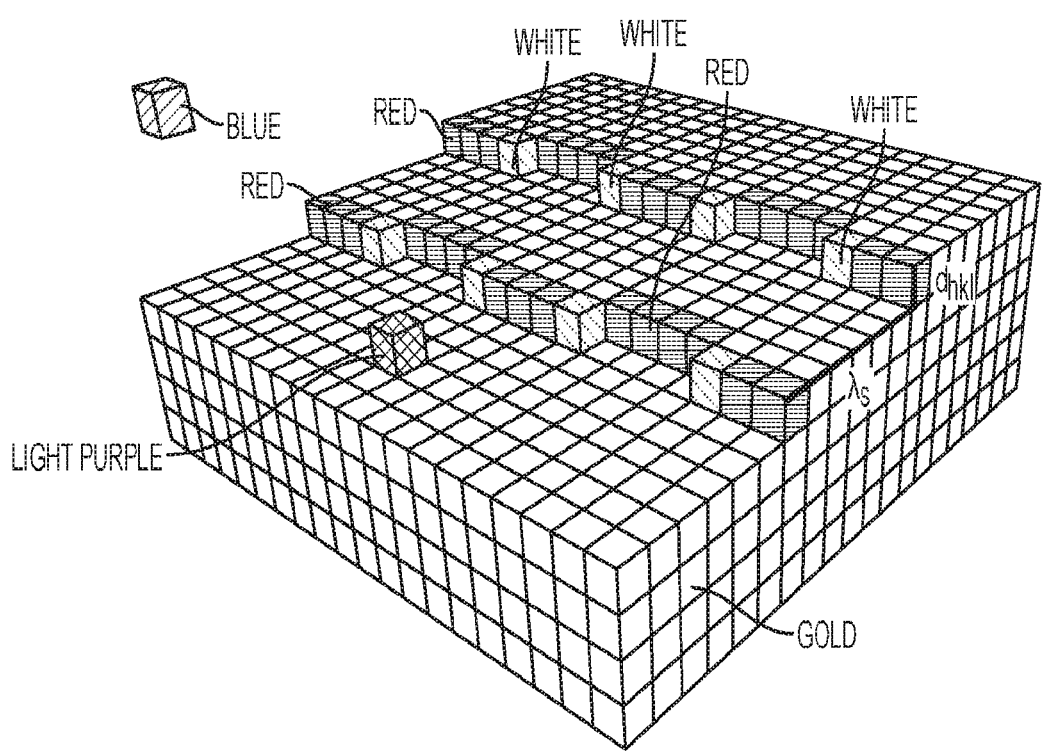
FIG. 15 illustrates a structure of a crystal facet. The facets of metal nanoparticles, and crystals in general, are composed of several distinct sites. The environment of an atom on a facet, particularly the number of nearest-neighbor bonds it possesses, determines its free energy and it is therefore important to define and distinguish between the different types of surface sites. Classically, the different sites have been described as terraces (gold), edges (red), kinks (white), and adatoms (light purple). Atoms in solution that are not bound to the nanoparticle surface are defined to be solvated (blue).

Controlling the shape of nanoparticles is a very complicated process. In order to understand how to do this, it is important to understand what the surface of a metal nanoparticle looks like (FIG. 15). Rather than perfectly smooth crystal faces, nanoparticles have terraced surfaces punctuated by edges and kinks. The nanoparticle grows by continuously adding atoms to these surface sites via either one-, two-, or three-dimensional surface nucleation. The concentration of metal atoms near the nanoparticle surface at any given time is the determining factor for whether 1-D, 2-D, or 3-D surface nucleation is dominant. This is fundamentally a reflection of the reaction kinetics, with slow kinetics producing low concentrations of metal atoms near the nanoparticle surface and yielding 1-D surface nucleation, and faster kinetics resulting in higher concentrations of metal atoms leading to 2- or 3-D surface nucleation.

Among the many things that can vary along the nanoparticle surface, the average terrace length, formally called the step separation, $\lambda_s$, is particularly important in determining the shape that a nanoparticle will ultimately possess. This is because the growth rate of a given facet is inversely proportional to $\lambda_s$. That means the parts of the nanoparticle surface that are densely terraced, or "jagged," grow faster than smoother parts of the surface. Fundamentally, it is the ability to control the surface of the growing nanoparticle—which parts are smooth and which parts are jagged—that determines an ability to control the nanoparticle's shape.

In order for highly anisotropic growth to occur, a surface configuration typically needs to be obtained that has a steady-state step distribution with the proper symmetry of fast- and slow-growing faces. In other words, as the nanoparticle grows, the jagged parts need to remain jagged and the smooth parts need to remain smooth in order for anisotropic growth to continue. Alternatively, in some embodiments, a surface configuration that presents re-entrant groups can achieve an analogous effect. For 1-D growth, faces with perpetual step defects like staking faults present on the surface act as jagged, fast-growing faces under slow reaction kinetics. For this reason, nanoparticles that have staking faults will grow fastest from the sides, where the stacking faults reach the surface. The resulting shape is a nanoplate (shown, for example, FIGS. 16A and 16D). In the case of 2-D surface nucleation, faces that have terraces stacked in such a way that the surface area of each terrace is equal will maintain that same jagged configuration during growth. When these formations occur at opposite ends of a nanoparticle, nanorod growth occurs (shown, for example, in FIGS. 16B and 16E). Finally, in the 3-D surface nucleation regime, protrusions will extend outward from the nanoparticle core as long as there is a sufficiently high concentration of metal atoms near the evolving surface. This is how nanostars grow (shown, for example, in FIGS. 16C and 16F).

A clear understanding of metal nanoparticle growth is critical to the ability to control the shape and size of metal nanoparticles. Some embodiments discussed herein relate to balancing reduction (production of metal atoms) and oxidation (transformation of metal atoms into metal ions) reactions in such a way that ideal/desired surface structures necessary for inducing anisotropic growth are achieved. As discussed above, hydrogen peroxide can serve multiple roles simultaneously, which makes it a convenient choice for simplifying reaction conditions, other agents (e.g., other reducing agents, e.g., mild reducing agents) may also be used for enabling finely-controlled anisotropic growth.

In some embodiments, the process of growing anisotropic nanoparticles having desired shapes and sizes is started with metal seeds. In some embodiments, starting with seeds is not a priori necessary; in other words, in some embodiments, the growth process starts with metal atoms, and then seeds having a desired structure are grown. In some embodiments, starting the anisotropic nanoparticle growth process with seeds allows for precise control of the initial population of crystals that have a particular symmetry of jagged and smooth surfaces. In some embodiments, for example, if more rods (as opposed to other shapes) are desired, a batch of seeds that contain a large proportion of seeds with jagged surfaces on opposite ends may be produced. In some embodiments, for example, if more plates are desired, a batch containing a large number of seeds with stacking faults could be produced.

The explanations presented above can be represented mathematically in a formula that is useful for understanding shape-controlled nanoparticle growth.

Anisotropic metal nanoparticles demonstrate exceptional physical and chemical properties that can be finely tuned by controlling their shape and size. The fields of chemical and biological sensing, catalysis, and nanoparticle-based biomedical imaging and therapy have been revolutionized by the advent of shape-controlled metal nanoparticle syntheses and the basic research into their properties that followed. Because of this great research and industrial interest, the design rules that govern shape and size of metal nanoparticles grown from solutions have received considerable attention, but the field remains divided as to which parameters are fundamentally dictating morphology.

The unparalleled success of these methods for producing precisely controlled morphologies has led to a widely held belief that auxiliary reagents are a priori required to induce anisotropic growth. In particular, the most commonly cited theory explaining anisotropic growth holds that adsorption of chemicals onto specific facets substantially slows the growth rate of those facets such that they dominate the growth form, as discussed, for example, in C. J. Murphy et al., *J Phys Chem B* 109, 13857 (Jul. 28, 2005). In this sense, nanorod formation is thought to require preferential binding of auxiliary reagents to the side facets of a seed crystal such that growth is promoted outward from the ends. While this is the most popular explanation for anisotropic growth it has been criticized as unrealistic due to the fact that a variety of shapes dominated by different facets form in the same synthesis, and many dissimilar reaction conditions can produce identical morphologies, as discussed, for example, in C. Lofton, W. Sigmund, *Adv Funct Mater* 15, 1197 (July, 2005).

There is currently no unified theory for metal nanoparticle growth capable of explaining the expansive collection of experimental findings in the literature. This is of concern to experimentalists, rather than theoreticians alone, because the current approach of inducing anisotropy by means of surfactants or polymers produces nanoparticles with surfaces that are largely passivated by the auxiliary reagents, which is generally undesirable. These adsorbates inhibit surface-dependent applications like catalysis and sensing, and the surfactant most commonly used—cetyl trimethylammonium bromide (CTAB)—is highly cytotoxic and necessitates post-synthetic ligand displacement. This process simply exchanges one passivating layer for another, however, and is not expected to significantly improve nanoparticle performance in surface-dependent applications. Alternative strategies for metal nanoparticle growth capable of yielding shape-controlled growth without passivating the functional surface are needed.

In order to understand and control the factors governing the shape and size of metal nanoparticles, an expression for the relative growth rates of the facets is determined. According to modern crystal growth theory, an accurate theoretical construct should reflect nanoparticle growth as a complex interplay between kinetic and thermodynamic effects that results in the formation and propagation of surface steps. The rate, $R_{hkl}$, at which a facet with Miller indices hkl grows is given by the expression:

$$R_{hkl} = v_{hkl}^{step} d_{hkl} \lambda_{hkl}^{-1} \qquad \text{Eq. 1}$$

where $v_{hkl}^{step}$ is the velocity at which a step propagates along the facet, $d_{hkl}$ is the height of a monolayer, and $\lambda_{hkl}$ is the distance between steps (FIG. 15). Because steps either form at self-propagating defect sites like stacking faults and screw dislocations, or require nucleation of adatom islands, $\lambda_{hkl}$ is strongly dependent upon defect symmetry and supersaturation, as given by the gradient of the chemical potential ($\Delta\mu = k_B T \ln [C(t)/C_0]$). The supersaturation determines whether addition of atoms to the growing crystal occurs via one-, two-, or three-dimensional surface nucleation (FIG. 17A).

The difficulty in applying Equation 1 above to understand metal nanoparticle growth is the inability to formulate an intuitive expression for $v_{step}$ in terms of experimentally relevant parameters. Such an expression is developed as shown below, yielding a new equation for the relative growth rates of metal nanoparticle facets that elucidates for the first time the role of several important parameters on inducing anisotropy:

$$R_{hkl}^{rel} \propto \rho_{kink} d_{hkl} \lambda_s^{-1} \{[M^0]^{eff} - [\Gamma + \Theta]\} \qquad \text{Eq. 2}$$

$$\Gamma = \frac{D_S}{I_K}\left(\frac{C_0}{C(t)}\right) e^{\frac{\left[\frac{\partial(\sigma A)}{\rho_V \partial V}\right]_{hkl}}{k_B T}}$$

$$\Theta = \frac{D_{Ox}}{I_K} e^{\frac{\Delta G_I - \Delta G_{Ox}}{k_B T}} [X^-]_{hkl}^{eff} [Ox]_{hkl}^{eff}$$

where $\rho_{kink}$ is the density of kinks along a step; $[M^0]_{hkl}^{eff}$, $[X^-]_{hkl}^{eff}$, and $[Ox]_{hkl}^{eff}$ are, respectively, the effective concentrations of metal atoms, complexing ligands (e.g., halides), and oxidants at the step site; $D_S$, $I_K$, and $D_{Ox}$ are constants; $C_0$ is the solubility of the metal atom in the given solvent; $C(t)$ is the concentration of metal atoms in solution; $\sigma$ is the specific surface free energy; $\rho_V$ is the density of atoms per unit volume; $\Delta G_I$ and $\Delta G_{Ox}$ are the activation energy barriers for incorporating a metal atom into a kink site and removing a ligated metal cation from a kink site, respectively; $k_B$ is Boltzmann's constant, and T is the absolute temperature. $[\partial(\sigma A)/\rho_V \partial V]_{hkl}$ is the change in surface energy per atom added in the [hkl]-direction (see Supporting Information) and can be analytically determined for polyhedral nanoparticles by deriving expressions for the partial derivatives of surface area, A, and volume, V, with respect to growth in the direction of a particular facet. For design considerations, however, it is clear that F depends exponentially upon the change in anisotropy (i.e., change in surface-area-to-volume ratio) resulting from growth in a given direction, and $\Theta$ depends on the concentrations of complexing ligands and oxidants.

Derivation of General Theory of Metal Nanocrystal Growth—Development of Equation 2

Definitions $R_{hkl}$=Growth rate in [hkl]-direction
$d_{hkl}$=lattice spacing in [hkl]-direction (height of monolayer)
$v_{step}$=velocity of step propagation
$\lambda_s$=distance separating steps
$I_K$=Arrhenius prefactor for rate of metal atom incorporation into kink sites
$D_S$=Arrhenius prefactor for rate of metal atom removal from kink sites by solvation
$D_{Ox}$=Arrhenius prefactor for rate of metal cation removal from kink sites
$\Delta G_I$=activation energy of metal atom incorporation into kink sites
$\Delta G_S$=activation energy of metal atom removal from kink sites by solvation
$\Delta G_{Ox}$=Activation energy of metal cation removal from kink sites
$[M^0]^{eff}$ effective concentration of metal atoms at steps
$[X^-]^{eff}$=effective concentration of complexing ligands at steps
$[OX]^{eff}$=effective concentration of oxidants at steps
$\mu_i$=chemical potential of species i in solution
$\mu_{cbb(l)}$=chemical potential of solute in solution
$\mu_{cbb(s)}$=chemical potential of solute in crystal
$n_i$=moles of species i in solution
$n_{cbb(l)}$=moles of metal atoms in solution
$n_{cbb(s)}$=moles of metal atoms in crystal
V=Volume
$\sigma$=specific surface free energy
A=Surface Area
$\Delta_\mu$=gradient of chemical potential
$\rho_v$=volume density of metal atoms in crystal
C(t)=concentration of metal atoms in solution at time t
$C_0$=solubility of metal atom
$\rho_{kink}$=kink density (number of kinks per edge)
$k_B$=Boltzmann's constant
T=temperature (K)

From classical crystal growth theory it is known that $$R_{hkl} = \frac{d_{hkl} v_{step}}{\lambda_s} \qquad \text{Eq. 3}$$

The velocity of step propagation is proportional to the net rate at which atoms are incorporated into kink sites $$R_{hkl} \propto \frac{d_{hkl}}{\lambda_s}\left(\frac{\text{kinks filled}}{s}\right) \qquad \text{Eq. 4}$$

For metal nanoparticles, the net rate at which atoms become incorporated into kinks is given by the rate of atoms binding into kink sites minus the rate of atoms leaving kink sites via solvation minus the rate of oxidized metal cations leaving the kink sites.

$$\left(\frac{\text{kinks filled}}{s}\right) = I_K e^{-\frac{\Delta G_I}{k_B T}}[\text{kinks}][M^0]^{\text{eff}} - \\ D_S e^{-\frac{\Delta G_S}{k_B T}}[\text{kinks}] - D_{Ox}e^{-\frac{\Delta G_{Ox}}{k_B T}}[\text{kinks}][X^-]^{\text{eff}}[Ox]^{\text{eff}} \qquad \text{Eq. 5}$$

An alternative form of this expression leads to an interesting substitution $$\left(\frac{\text{kinks filled}}{s}\right) = [\text{kinks}] \qquad \text{Eq. 6}$$

$$\left(I_K e^{-\frac{\Delta G_I}{k_B T}}[M^0]^{\text{eff}} - D_S e^{-\frac{\Delta G_S}{k_B T}} - D_{Ox}e^{-\frac{\Delta G_{Ox}}{k_B T}}[X^-]^{\text{eff}}[Ox]^{\text{eff}}\right)$$

$$\left(\frac{\text{kinks filled}}{s}\right) = [\text{kinks}]\left(I_K e^{-\frac{\Delta G_I}{k_B T}}[M^0]^{\text{eff}} - \\ D_S e^{-\frac{\Delta G_S + \Delta G_I - \Delta G_I}{k_B T}} - D_{Ox}e^{-\frac{\Delta G_{Ox}}{k_B T}}[X^-]^{\text{eff}}[Ox]^{\text{eff}}\right) \qquad \text{Eq. 7}$$

$$\left(\frac{\text{kinks filled}}{s}\right) = [\text{kinks}] \qquad \text{Eq. 8}$$

$$\left(I_K e^{-\frac{\Delta G_I}{k_B T}}[M^0]^{\text{eff}} - D_S e^{\frac{\Delta G_I}{k_B T}} - D_{Ox}e^{-\frac{\Delta G_{Ox}}{k_B T}}[X^-]^{\text{eff}}[Ox]^{\text{eff}}\right)$$

In this expression, $$e^{-\frac{\Delta G_I - \Delta G_S}{k_B T}},$$

can be represented in a more intuitive form. In order to see this, the below equations begin with the equation for the change in Gibbs free energy in a closed system under constant temperature and pressure:

$$dG = \sum_i \mu_i dn_i + \mu_{cbb(l)} dn_{cbb(l)} + \mu_{cbb(s)} dn_{cbb(s)} + d(\sigma A) \qquad \text{Eq. 9}$$

$$dG = \sum_i \mu_i dn_i - dn_{cbb(s)}(\mu_{cbb(l)} - \mu_{cbb(s)}) + d(\sigma A) \qquad \text{Eq. 10}$$

$$\frac{dG}{dn_{cbb(s)}} = \sum_i \mu_i\left(\frac{dn_i}{dn_{cbb(s)}}\right) - (\mu_{cbb(l)} - \mu_{cbb(s)}) + \frac{d(\sigma A)}{dn_{cbb(s)}} \qquad \text{Eq. 11}$$

$$\frac{dG}{\rho_V dV} = \sum_i \mu_i\left(\frac{dn_i}{\rho_V dV}\right) + \frac{d(\sigma A)}{\rho_V dV} - \Delta\mu \qquad \text{Eq. 12}$$

Assuming $n_i$ does not depend strongly on nanocrystal volume, $$\left(\frac{dn_i}{dV}\right) \approx 0 \qquad \text{Eq. 13}$$

And it follows that $$\frac{dG}{\rho_V dV} = \frac{d(\sigma A)}{\rho_V dV} - \Delta\mu \qquad \text{Eq. 14}$$

Therefore, the specific free energy change for crystal growth in the [hkl]-direction is $$\left(\frac{\partial G}{\rho_V dV}\right)_{hkl} = \left[\frac{\partial(\sigma A)}{\rho_V \partial V}\right]_{hkl} - \Delta\mu \qquad \text{Eq. 15}$$

Alternatively, the specific free energy change for growth in the [hkl]-direction can be expressed as $\Delta G_I - \Delta G_S$. Therefore, $$\Delta G_I - \Delta G_S = \left[\frac{\partial(\sigma A)}{\rho_V \partial V}\right]_{hkl} - \Delta\mu \qquad \text{Eq. 16}$$

$$\frac{\Delta G_I - \Delta G_S}{k_B T} = \frac{\left(\left[\frac{\partial(\sigma A)}{\rho_V \partial V}\right]_{hkl} - \Delta\mu\right)}{k_B T} \qquad \text{Eq. 17}$$

From the definition of the chemical potential gradient, $$\Delta\mu = k_B T \ln\left(\frac{C(t)}{C_0}\right) \qquad \text{Eq. 18}$$

Making the above substitution and simplifying by the properties of exponents yields:

$$e^{\frac{\Delta G_I - \Delta G_S}{k_B T}} = e^{\frac{\left[\frac{\partial(\sigma A)}{\rho_V \partial V}\right]_{hkl}}{k_B T}}\left(\frac{C_0}{C(t)}\right) \qquad \text{Eq. 19}$$

Making the substitution into the expression for the kink growth rate yields:

$$\left(\frac{\text{kinks filled}}{s}\right) = [\text{kinks}] \qquad \text{Eq. 20}$$

$$\left\{I_K e^{-\frac{\Delta G_I}{k_B T}}\left[[M^0]^{\text{eff}} - \left(\frac{D_S}{I_K}\right)e^{\frac{\left[\frac{\partial(\sigma A)}{\rho_V \partial V}\right]_{hkl}}{k_B T}}\left(\frac{C_0}{C(t)}\right)\right] - \\ D_{Ox}e^{-\frac{\Delta G_{Ox}}{k_B T}}[X^-]^{\text{eff}}[Ox]^{\text{eff}}\right\}$$

Factoring out $$I_K e^{-\frac{\Delta G_I}{k_B T}}$$

from the oxidation term leads to a more condensed form $$\left(\frac{\text{kinks filled}}{s}\right) = [\text{kinks}] \quad \text{Eq. 21}$$

$$\left\{I_K e^{-\frac{\Delta G_I}{k_B T}}\left[[M^0]^{e\!f\!f} - \left(\frac{D_S}{I_K}\right)e^{\frac{\left[\frac{\partial(\sigma A)}{\rho_V \partial V}\right]_{hkl}}{k_B T}}\left(\frac{C_0}{C(t)}\right)\right] - D_{Ox}e^{-\frac{\Delta G_{Ox}+\Delta G_I-\Delta G_I}{k_B T}}[X^-]^{e\!f\!f}[Ox]^{e\!f\!f}\right\}$$

$$\left(\frac{\text{kinks filled}}{s}\right) = [\text{kinks}] \quad \text{Eq. 22}$$

$$\left\{I_K e^{-\frac{\Delta G_I}{k_B T}}\left[[M^0]^{e\!f\!f} - \left(\frac{D_S}{I_K}\right)e^{\frac{\left[\frac{\partial(\sigma A)}{\rho_V \partial V}\right]_{hkl}}{k_B T}}\left(\frac{C_0}{C(t)}\right)\right] - D_{Ox}e^{-\frac{(\Delta G_{Ox}-\Delta G_I)}{k_B T}}e^{-\frac{\Delta G_I}{k_B T}}[X^-]^{e\!f\!f}[Ox]^{e\!f\!f}\right\}$$

$$\left(\frac{\text{kinks filled}}{s}\right) = [\text{kinks}] \quad \text{Eq. 23}$$

$$\left\{I_K e^{-\frac{\Delta G_I}{k_B T}}\left[[M^0]^{e\!f\!f} - \left(\frac{D_S}{I_K}\right)e^{\frac{\left[\frac{\partial(\sigma A)}{\rho_V \partial V}\right]_{hkl}}{k_B T}}\left(\frac{C_0}{C(t)}\right) - \left(\frac{D_{Ox}}{I_K}\right)e^{\frac{\Delta G_I-\Delta G_{Ox}}{k_B T}}[X^-]^{e\!f\!f}[Ox]^{e\!f\!f}\right]\right\}$$

$$\left(\frac{\text{kinks filled}}{s}\right) = [\text{kinks}] \quad \text{Eq. 24}$$

$$\left\{I_K e^{-\frac{\Delta G_I}{k_B T}}\left[[M^0]^{e\!f\!f} - \left(\frac{1}{I_K}\right)\left(D_S e^{\frac{\left[\frac{\partial(\sigma A)}{\rho_V \partial V}\right]_{hkl}}{k_B T}}\left(\frac{C_0}{C(t)}\right) + D_{Ox}e^{\frac{\Delta G_I-\Delta G_{Ox}}{k_B T}}[X^-]^{e\!f\!f}[Ox]^{e\!f\!f}\right)\right]\right\}$$

The concentration of kinks along a step is defined as the kink density, thus [kinks] may be rewritten in its more common form ($\rho_{kink}$)

$$\left(\frac{\text{kinks filled}}{s}\right) = \rho_{kink} I_K e^{-\frac{\Delta G_I}{k_B T}}\left[[M^0]^{e\!f\!f} - \left(\frac{1}{I_K}\right)\right. \quad \text{Eq. 25}$$
$$\left.\left(D_S\left(\frac{C_0}{C(t)}\right)e^{\frac{\left[\frac{\partial(\sigma A)}{\rho_V \partial V}\right]_{hkl}}{k_B T}} + D_{Ox}e^{\frac{\Delta G_I-\Delta G_{Ox}}{k_B T}}[X^-]^{e\!f\!f}[Ox]^{e\!f\!f}\right)\right]$$

The activation energy for incorporating atoms into kinks is roughly equal to the energy of removing the solvation shell, which is largely independent of facet index, especially for the common low-energy facets. Thus, $$I_K e^{-\frac{\Delta G_I}{k_B T}}$$

is approximately constant over all facets and cancels out in the relative rate expression $$\left(\frac{\text{kinks filled}}{s}\right) \propto \rho_{kink}\left[[M^0]^{e\!f\!f} - \right. \quad \text{Eq. 26}$$

-continued $$\left.\left(\frac{1}{I_K}\right)\left(D_S\left(\frac{C_0}{C(t)}\right)e^{\frac{\left[\frac{\partial(\sigma A)}{\rho_V \partial V}\right]_{hkl}}{k_B T}} + D_{Ox}e^{\frac{\Delta G_I-\Delta G_{Ox}}{k_B T}}[X^-]^{e\!f\!f}[Ox]^{e\!f\!f}\right)\right]$$

Substituting this expression into $$R_{hkl} \propto \frac{d_{hkl}}{\lambda_s}\left(\frac{\text{kinks filled}}{s}\right)$$

yields $$R_{hkl}^{rel} \propto \frac{\rho_{kink} d_{hkl}}{\lambda_s}\left[[M^0]^{e\!f\!f} - \right. \quad \text{Eq. 27}$$
$$\left.\left(\frac{1}{I_K}\right)\left(D_S\left(\frac{C_0}{C(t)}\right)e^{\frac{\left[\frac{\partial(\sigma A)}{\rho_V \partial V}\right]_{hkl}}{k_B T}} + D_{Ox}e^{\frac{\Delta G_I-\Delta G_{Ox}}{k_B T}}[X^-]_{hkl}^{e\!f\!f}[Ox]_{hkl}^{e\!f\!f}\right)\right]$$

This equation 27 may be separated into its fundamental terms in order to make it more intuitive—expressed as Equation 2 above.

III. Reagents for Preparing Nanoparticle Cores

As described herein, the present invention provides sets of reagents for use in preparing compositions comprising nanoparticle cores of distinct geometries (e.g., anisotropic nanoparticle cores as described herein). In some embodiments, such compositions comprise or consist of metal seeds together with environmentally benign reagents.

Some embodiments described herein relate to preparation of metal seeds with a pre-defined structure (e.g., one or both of internal crystalline structure and surface structure). In some embodiments, pre-defined structure may be controlled by appropriate selection of redox potential and reaction conditions. In some embodiments, structures include, but are not limited to, single crystalline, single twinned, and multiply-twinned seeds, as well as seeds containing stacking faults, screw dislocations, re-entrant grooves, cross-twinning, or any combination thereof, such that facets present appropriate structural features for promoting or inhibiting growth under various conditions (e.g., as discussed herein).

In some embodiments, appropriate structural features for classification as "fast-growing" surfaces include screw dislocations, re-entrant grooves, cross twins, grain boundaries, stacking faults, and any other feature(s) that catalyzes and/or stabilizes the nucleation of monolayers. Facets substantially free of these features can be defined as "slow-growing". Thus, in some embodiments, rational engineering of seeds with desired symmetries of fast-growing and slow-growing facets is a critical first step for shape control. In some embodiments, rational engineering of seeds with desired symmetries of fast-growing and slow-growing facets is the critical first step for shape control.

As described herein, once a groove is introduced, the shape that forms can be controlled. Various mechanisms can introduce grooves. For example, grooves can be introduced via oxidation (e.g., growth under fast conditions) or a fusion of two or more seeds.

In some embodiments, utilized metal seeds are less than 5 nm in size (e.g., in their longest diameter or length). In some embodiments, utilized metal seeds are of a desired crystallinity. For example, in some embodiments, utilized metal seeds are or comprise single crystals (e.g., to generate nanoparticles of a shape selected from basic platonic shapes, cubes, decahedra, octahedra, spheres, tetrahedra, etc.). In some embodiments, utilized metal seeds are or comprise singly twinned crystals (e.g., to generate nanoparticles of a shape selected from beams, plates, etc.). In some embodiments, utilized metal seeds are or comprise multiply twinned crystals (e.g., to generate nanoparticles of a shape selected from plates, rods, etc.).

In some embodiments, provided reagent sets include metal seeds, an etching agent, and a source of metal ions. In some embodiments, the etching agent is or comprises hydrogen peroxide ($H_2O_2$). In some embodiments, the etching agent is or comprises hydroxylamine. However, in some embodiments, hydroxylamine is not used, as the present invention recognizes the source of a problem in many methodologies that utilize hydroxylamine in that it can have toxic effects. In some embodiments, metal ions are provided from a metal hydroxide or a metal salt. In some such embodiments, the counterion in the metal salt is a halide (e.g., Cl, Br, etc.). In some embodiments, a metal salt can both act as an etching agent and provide metal ions. In some embodiments, a metal halide (e.g., a metal chloride, metal bromide, etc.) is used. In some particular embodiments, the metal is gold, the etching agent is or comprises peroxide, and/or the counter ion is provided in the form of a metal halide (e.g., $HAuCl_4$). In some embodiments, a metal precursor complex different than $HAuCl_4$ may be used.

In some embodiments, provided reagent sets include a reducing agent (e.g., to counteract, delay, slow down, or terminate activity of an etching agent).

In some embodiments, a metal salt can both act as an etching agent and provide a source of metal ions. In some such embodiments, no other reducing agent is utilized.

In some embodiments, provided reagent sets include pH adjusting agents (e.g., a base, such as sodium hydroxide, and/or an acid, such as hydrogen chloride) appropriate to adjust pH of a nanoparticle growth reaction to conditions as described herein or otherwise understood by those skilled in the art, in light of the present disclosure, to be useful or desirable for the production of anisotropic metal nanoparticles.

In some embodiments, a provided reagent set may be provided and/or utilized together with certain equipment such as, for example, a pH monitor, a temperature monitor and/or a heat or cooling source.

For example, in some particular embodiments, nanoparticle assembly reactions are performed at a mild temperature (e.g., at or below room temperature); appropriate equipment may be provided and/or utilized. In some such embodiments, the temperature is within a range between a lower value and an upper value, inclusive, wherein the lower value is selected from the group consisting of 1° C., 2° C., 3° C., 4° C., 5° C., 6° C., 7° C., 8° C., 9° C., and 10° C., and the upper value is selected from the group consisting of 15° C., 16° C., 17° C., 18° C., 19° C., 20° C., 21° C., 22° C., 23° C., 24, ° C., 25° C., 26° C., 27° C., 28° C., 29° C., 30° C.). In some embodiments, the temperature is within the range of about 0° C. to about 38° C., and/or within a range of about 2° C. to about 28° C. In some particular embodiments, reactions are performed at or around 25° C. or at or around 4° C.

In some particular embodiments, nanoparticle assembly reactions are performed at an elevated temperature (e.g., at or above, and particularly above, room temperature); appropriate equipment may be provided and/or utilized. In some such embodiments, the temperature is within a range between a lower value and an upper value, inclusive, wherein the lower value is selected from the group consisting of 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 79° C., 71° C., 72° C., 73° C., 74° C., 75° C., and the upper value is selected from the group consisting of 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C. In some embodiments, the temperature is within the range of about 60° C. to about 105° C. and/or within a range of about 65° C. to about 100° C. In some particular embodiments, the reactions are performed at or around 70° C. or at or around 100° C.

In some embodiments, elevated temperatures are utilized when a metal ion is an etching agent (e.g., as a sole etching agent, in the absence of other etching agents). In some embodiments, mild conditions are utilized when hydrogen peroxide is utilized as an etching agent.

In some embodiments, provided reagent sets consist of metal seeds, an etching agent, and a reducing agent. In some embodiments, provided reagent sets consist of metal seeds, metal ions and counter ions (e.g., provided as a metal hydroxide or a metal salt such as a metal halide), and hydrogen peroxide. In some embodiments, provided reagent sets consist of metal seeds, metal ions and counter ions (e.g., provided as a metal hydroxide or a metal salt such as a metal halide, hydrogen peroxide, and sodium hydroxide. In some particular such embodiments, the metal is gold (e.g., the provided seeds are gold seeds) and/or the metal salt is a gold hydroxide or a gold salt such as a gold halide (e.g., $HAuCl_4$). In some embodiments, a metal precursor complex different than $HAuCl_4$ may be used.

In some embodiments, reagent sets are provided in the form of kits, for example with certain individual components separately housed in individual containers, optionally within a single housing or package.

IV. Uses and Applications

Those of ordinary skill in the art, reading the present disclosure, will immediately appreciate that provided methodologies and compositions are useful in a wide range of contexts, including both medical and non-medical applications. As noted above, for example, nanoparticle systems (e.g., gold nanoparticles) have tremendous potential and are useful in a wide variety of contexts, including in electronics (e.g., as transistors or conductors, useful among other things in printable inks and/or electronic chips, for example, to connect components such as resistors, conductors, and/or other elements), to generate heat (e.g., when excited by radiation, for use in photodynamic and/or hyperthermia therapy), to deliver payloads (e.g., therapeutic, diagnostic, and/or imaging payloads), in sensor technologies (e.g., colorimetric sensors, for example that identify foods suitable for consumption), for imaging indications (e.g., utilizing transmission electron microscopy, surface enhanced Raman spectroscopy and/or light scattering technologies), and catalysis (e.g., to catalyze selective oxidation reactions and/or to reduce production of nitrogen oxides or other toxic or environmentally harmful compounds). Nanoparticle systems are of particular interest for use in imaging tumor resection boundaries and/or for detecting biomarkers (e.g., in the diagnosis of heart diseases, cancer, infection, etc.). Nanoparticle systems are also often employed in lateral flow assays such as home pregnancy tests. Certain nanoparticle systems are also being developed for fuel cell and/or alternative energy applications. Provided nanoparticle compositions are particularly useful in catalysis and/or imaging (e.g., geometrically-tagged imaging) applications.

Nanoparticle preparation technologies and compositions provided herein are particularly useful, for instance, in biomedical research methodologies (such as, but not limited to, cell tracking, cell sorting, western blotting), solar cells, quantum computing-based applications/methods, anti-counterfeit applications/methods, barcoding, optics, (nano)photonics.

Another particular use for provided compositions and methodologies is in clinical imaging, for example during surgery (e.g., to define tumor resection boundaries).

In some embodiments, uses of provided nanoparticles comprise administering nanoparticles (e.g., nanoparticle compositions) to a single sample, source, or site (e.g., subject) of interest.

EXEMPLIFICATION

Example 1: Green Synthesis of Anisotropic Gold Nanoparticles

Anisotropic gold nanoparticles are known to have unique properties that are highly dependent on nanoparticle morphology. Given their value and usefulness in a variety of applications, significant investment has been made in the development of methods that produce anisotropic morphologies and permit precise control over their size and shape. However, the present invention recognizes the source of a problem with many such technologies, in that they typically require toxic auxiliary reagents, such as cetyltrimethylammonium bromide ("CTAB"), that are used to promote shape-directed growth by blocking specific crystal facets on the nanoparticle surface. The present invention appreciates that such auxiliary reagents can compromise the nanoparticle surface and impede biomedical applications. Furthermore, most such agents are not benign environmentally. The present invention therefore recognizes a need for the development of new and more environmentally friendly technologies for preparation of anisotropic gold nanoparticles.

The present Example describes one such new technology. Specifically, here, it is reported that a seed-mediated synthesis of anisotropic gold nanoparticles (e.g., rods, stars, plates) in the absence of any toxic chemical, by precisely controlling the balance between growth and oxidative etching in hydrogen peroxide-mediated reduction of gold chloride ($HAuCl_4$). Although the present Example relates to seed-mediated synthesis, those of ordinary skill in the art will appreciate that the gold seeds may be prepared in situ by known methods. In some embodiments, the morphology of prepared anisotropic gold nanoparticles is stabilized from transformation to more thermodynamically stable geometries by removal of residual reactants; in some such embodiments pure water dispersions are generated.

Gold nanoparticles (GNP) exhibit unique chemical and physical properties widely applicable to diverse fields such as catalysis (1), sensing (2), surface-enhanced Raman spectroscopy (SERS) (3), photonics (4) and biomedical imaging and therapeutics (5, 6). The specific properties of GNP are strongly dictated by size, shape and local dielectric environment (7). A variety of methods is available that can produce discrete anisotropic nanoparticles; however, such methods typically rely on poorly defined natural extracts, toxic chemicals such as silver (Ag), dimethylformamide, ethylene glycol, cetyltrimethylammonium bromide (CTAB), and/or stabilizing polymers such as polyvinylpyrrolidone (PVP) (8-13). These stabilizing and shape-directing reagents block the GNP surface, thereby limiting the binding of functional molecules. Use of toxic components necessitates post-synthetic removal (14). Very often, such removal generates copious waste relative to the amount of materials made.

Prior to the present invention, the understanding by which these syntheses were considered to contribute to shape-directed anisotropic GNP formation involves a complex interplay between thermodynamic and kinetic processes (15). The specific morphology formed was thought to depend on the rate of reaction, the presence of various structural defects in the growing nanoparticle, and the degree of surface blocking—a process wherein chemical species in solution (e.g., $CTA^+$, Ag, PVP, etc.) preferentially bind to certain crystal facets, inhibiting gold deposition and/or decreasing surface energy at those sites, thereby driving growth in the direction of the less encumbered facets (16). Additional effects have been proposed for specific synthesis routes, such as micelle-gold complexes causing directed growth via coulombic interactions with growing particles (17). In addition to these commonly accepted mechanisms, oxidative etching has been implicated in directing the shape of GNP (11, 18).

Figure 1:
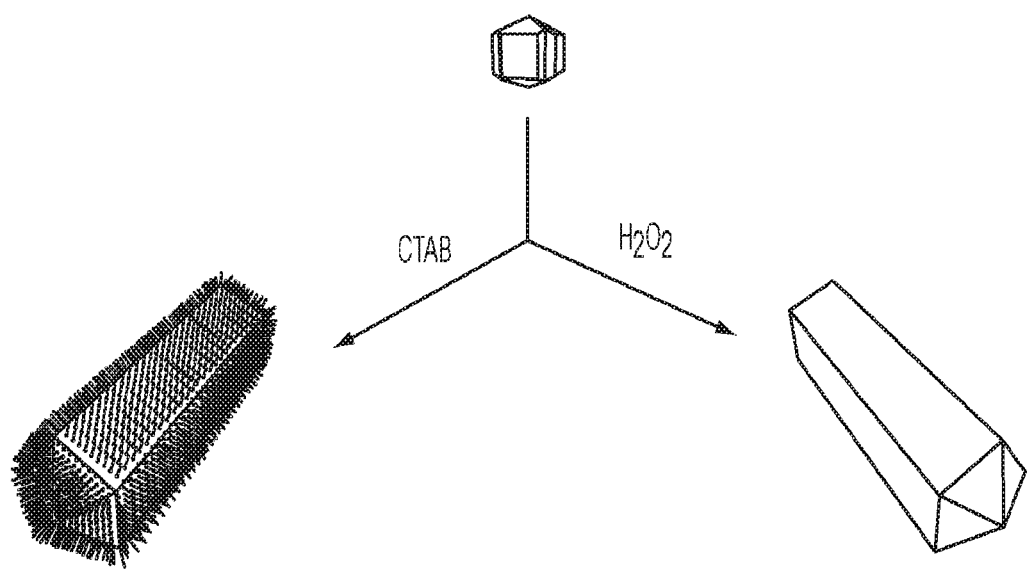
FIG. 1 illustrates a comparison of seed-mediated anisotropic nanoparticle synthesis methods. Conventional synthetic methods for anisotropic nanoparticle formation use surface-blocking groups to drive growth in the direction of the least encumbered facets. This leaves the surface largely blocked by species such as surfactants (e.g., CTAB) or polymers that diminish the effectiveness of the GNP for various applications. In contrast, the reaction of $H_2O_2$ with $HAuCl_4$ generates anisotropic nanoparticles with unblocked surfaces that are optimal for surface-dependent applications.

The present Example provides a straightforward, green, shape-directed synthesis of GNP with an approach that does not rely upon surface-blocking reagents (FIG. 1). The only reactants utilized in this synthesis consisted of hydrogen peroxide ($H_2O_2$), $HAuCl_4$, and nanoparticle seeds (specifically, 3 nm GNP seeds in this Example—although the nanoparticle seeds may also be generated in situ), with sodium hydroxide to raise pH when necessary. $H_2O_2$ was selected based on the recognition that it provides distinct advantages over typical organic reducing agents in that, for example, it also has excellent oxidative properties suitable for etching GNP (19), reduces $HAuCl_4$ with kinetics that are widely tunable by pH (20), and decomposes into $H_2O$ and $O_2$ making it environmentally benign. By varying the $H_2O_2$ concentration and the pH of reaction solutions, the influence of reaction kinetics and oxidative etching in the seed-mediated synthesis of anisotropic GNP was investigated.

Plates.

Figure 2A:
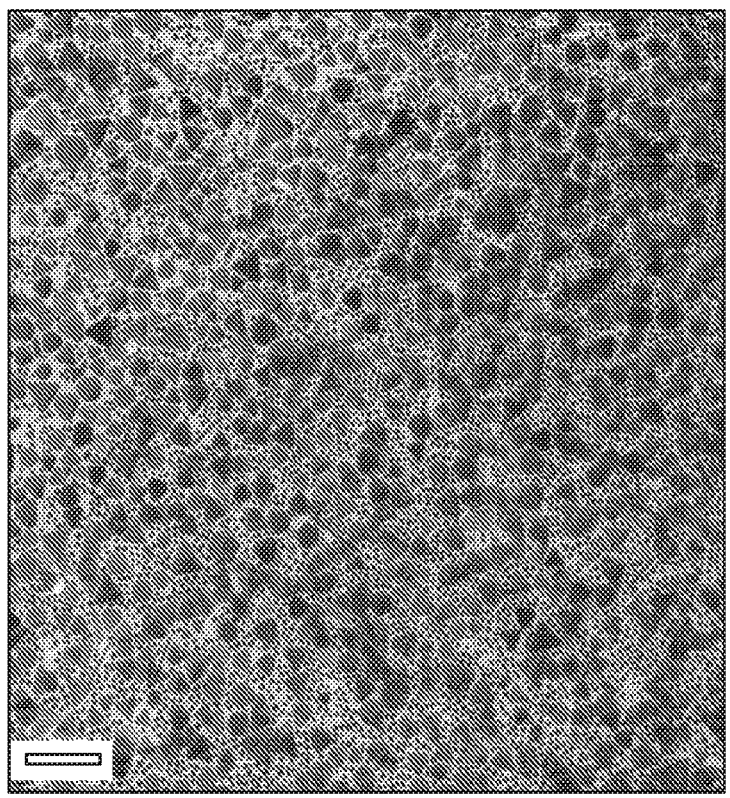
FIG. 2A shows nanoplates synthesized according to the protocol given in the Example 1. The reaction was allowed to proceed until completion and then polyvinylpyrrolidone was added so that the particles would be sufficiently well separated to determine the morphological yield. Pseudo-icosahedral particles and nanoplates constitute the vast majority of particles formed. The yield of plates was between 30-40% as synthesized. The scale bar is 500 nm.
Figure 2B:
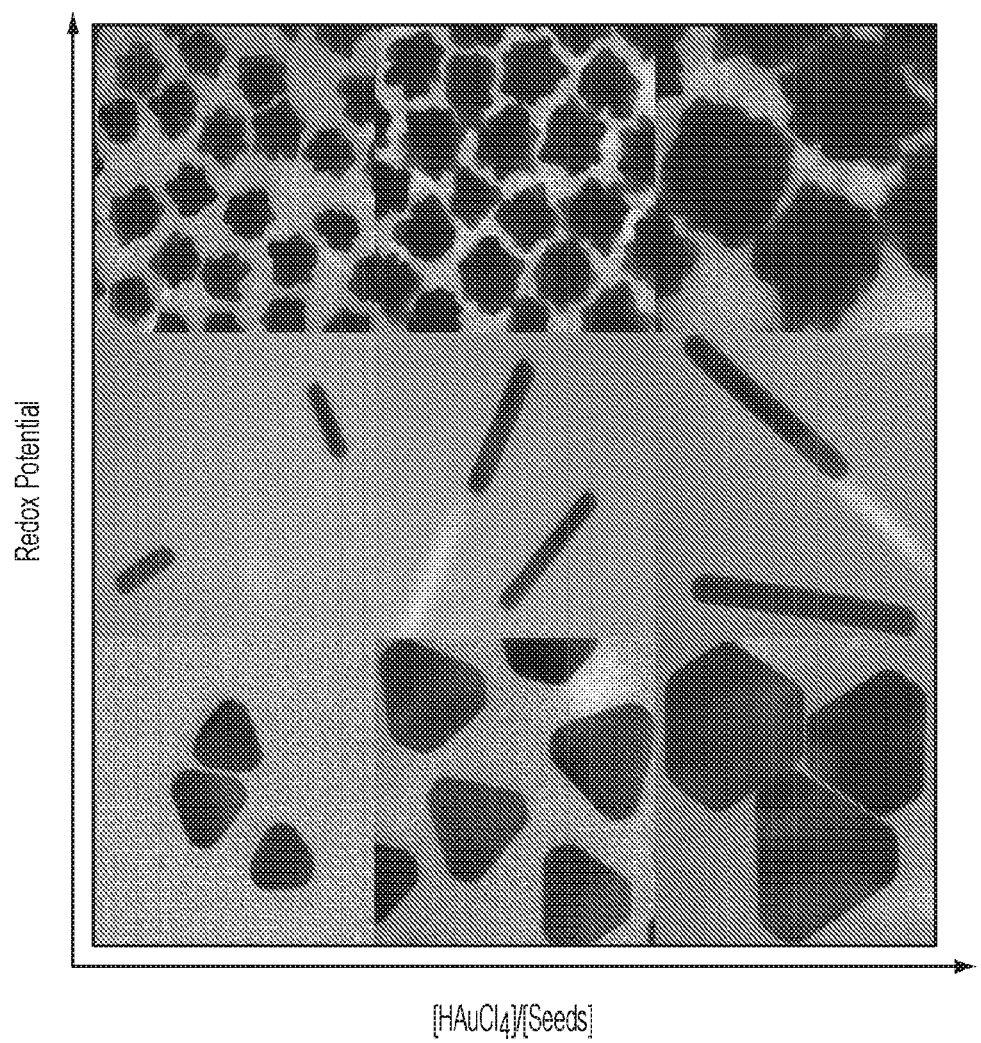
FIG. 2B shows anisotropic nanoparticle cores synthesized under various reaction conditions. Under the most oxidative conditions, the dominant morphology formed was nanoplates. Raising the ratio of $H_2O_2$ to $HAuCl_4$ increased the reduction kinetics slightly and resulted in the formation of nanorods as the dominant product. Introducing a base, such as NaOH, increased the reduction potential of $H_2O_2$ and resulted in fast reaction kinetics. Under these conditions, stars were formed. The ratio of $HAuCl_4$ to seeds controls the dimensions of the morphology formed. Increasing the ratio of $HAuCl_4$ to seeds increases the edge length of plates, the aspect ratio of rods and the size of stars.

$H_2O_2$ was titrated to a fixed [$HAuCl_4$]/[seeds] ratio until a purple-red color appeared after 30 min. These "slow" reaction kinetics corresponded to strong etching conditions because the nanoparticle seeds experienced prolonged exposure to oxidative species, such as $HAuCl_4$, $O_2$, and $H_2O_2$ that are known to etch GNP (11, 18, 19). Transmission electron microscopy (TEM) revealed the major product of this reaction to be gold nanoplates (FIG. 2A). The concentration of $H_2O_2$ could be increased until the purple-red color appeared after 30 s while maintaining the nanoplates as the dominant morphology. Adjusting the [$HAuCl_4$]/[seed] ratio at a given $H_2O_2$ concentration enabled facile tuning of the nanoplate edge length from less than 20 nm to over 1 μm, with longer edge lengths corresponding to larger [$HAuCl_4$]/[seed] ratios (FIG. 2B).

Rods.

Figure 2C:
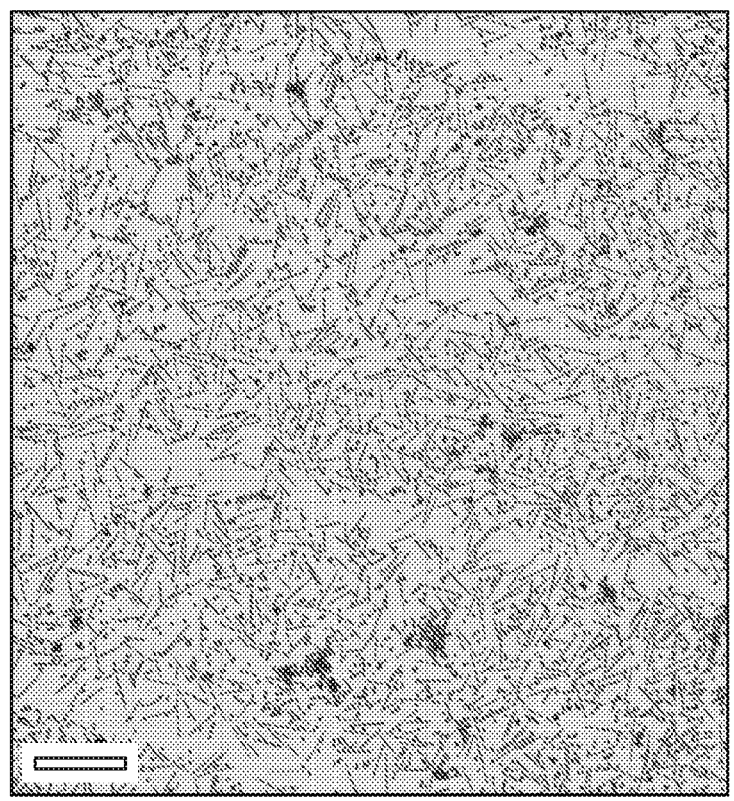
FIG. 2C shows nanorods synthesized according to the protocol given in Example 1. The reaction was allowed to proceed until completion and then polyvinylpyrrolidone was added so that the particles would be sufficiently well separated to determine the morphological yield. Pseudo-icosahedral particles and nanorods constitute the vast majority of particles formed. The yield of nanorods was between 30-50% as synthesized. The scale bar is 500 nm.

Increasing the [$H_2O_2$]/[$HAuCl_4$] ratio and reversing the order of addition (i.e., adding $HAuCl_4$ to $H_2O_2$ and seeds) yielded nanorods as the predominant shape (FIG. 2C). Typically, rods formed in about 30 seconds, coinciding with the appearance of a deep burgundy color. The aspect ratio of the nanorods could be finely tuned by controlling the [$HAuCl_4$]/[seeds] ratio (FIG. 2B). Aspect ratios greater than 20 were easily achieved without the need for multiple seeding steps. This is particularly important as it demonstrates that nanorods with widely tunable aspect ratios can be formed in high yields without the addition of micelles or strong surface-blocking agents. The nanorods were stable for weeks at room temperature and could be purified by centrifugation or fractionation techniques (12).

Stars.

Figure 2D:
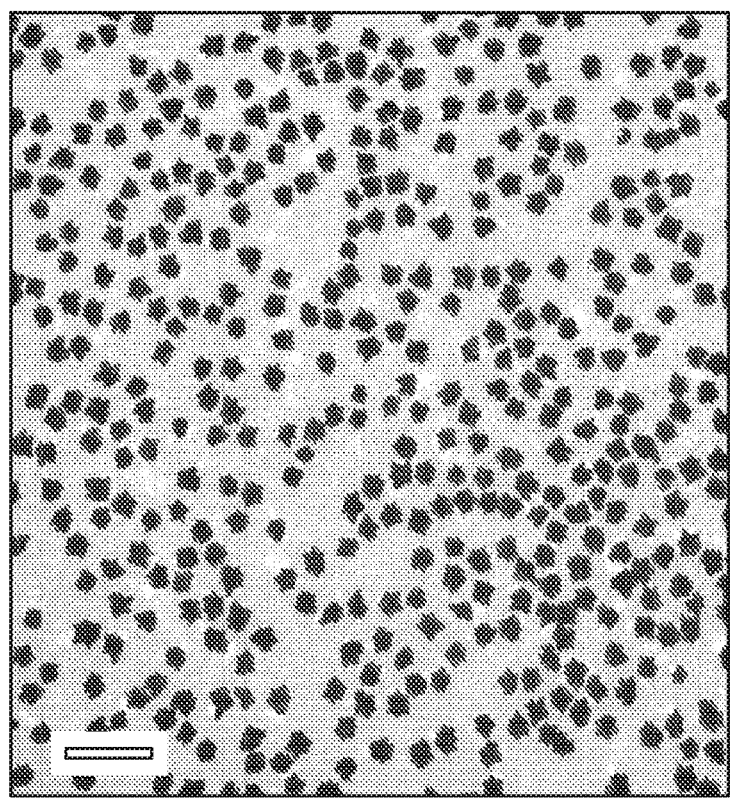
FIG. 2D shows nanostars synthesized according to the protocol given in the Example 1, and specifically with a concentration of 1.8 mM NaOH, 0.03% hydrogen peroxide, 346 μM $HAuCl_4$, and a final dilution of 1:73 of the starting seed concentration. The monodispersity is excellent for a benchtop, aqueous synthesis in the presence of oxygen. The reaction was allowed to proceed until completion and then polyvinylpyrrolidone was added so that the particles would be sufficiently well separated to determine the morphological yield. All observed particles were nanostars. The scale bar is 100 nm.

In order to probe reaction kinetics that cannot be obtained by further increasing the [$H_2O_2$]/[$HAuCl_4$] ratio, NaOH was introduced to increase the reduction potential of $H_2O_2$. The addition of 1.8 mM NaOH to a mixture of $HAuCl_4$, $H_2O_2$ and seeds initiates a reaction that can be followed by a color change from pale yellow to blue-green within less than 1 second. TEM revealed the reaction product to be narrowly dispersed gold nanostars with a mean diameter that could be tuned by the [$HAuCl_4$]/[seed] ratio (FIG. 2B). Furthermore, the aspect ratio of the protrusions could be controlled by the concentration of NaOH (FIG. 2D). In contrast to rods and plates, the nanostars exhibited a rapid transformation to pseudo-spherical morphologies that could be visually monitored by the accompanying color changes from blue-green to blue, then purple, and finally red. It has been demonstrated that removal of Cl$^-$ ions can stabilize similar nanostars from transformation for up to two weeks (21). In some embodiments discussed herein, dialyzing the nanostars immediately after synthesis afforded morphological stabilization for at least 3 months at room temperature as discussed below. As confirmed by experimental observation, nanostars produced according to methods discussed herein retained their morphology for several months without addition of stabilizing agents. In some embodiments, dialyzing the nanostars immediately after synthesis to remove the chloride ions, oxidants, Au salts, and other remaining species afforded morphological stabilization for at least six months at room temperature. In addition, in some embodiments, it was confirmed that purging the reaction solution with nitrogen to remove $O_2$ gas also inhibits transformation of the nanostar shapes.

The present Example surprisingly demonstrates that surface-blocking additives are not necessary for controlling the shape and size of GNP. Without wishing to be bound by any particular theory, it is noted that formation of nanoplates and nanostars in the present synthesis can be explained by mechanisms that identify seed structure and kinetics of $HAuCl_4$ reduction as the determining factors of GNP morphology (21, 22). However, formation mechanisms for nanorods independent of facet blocking have not previously been credibly established; they require an as yet unknown process to induce one-dimensional growth from a multiply-twinned seed (22). In some embodiments, the size of all anisotropic morphologies could be tuned simply by altering the [$HAuCl_4$]/[Seed] ratio.

Figure 3A:
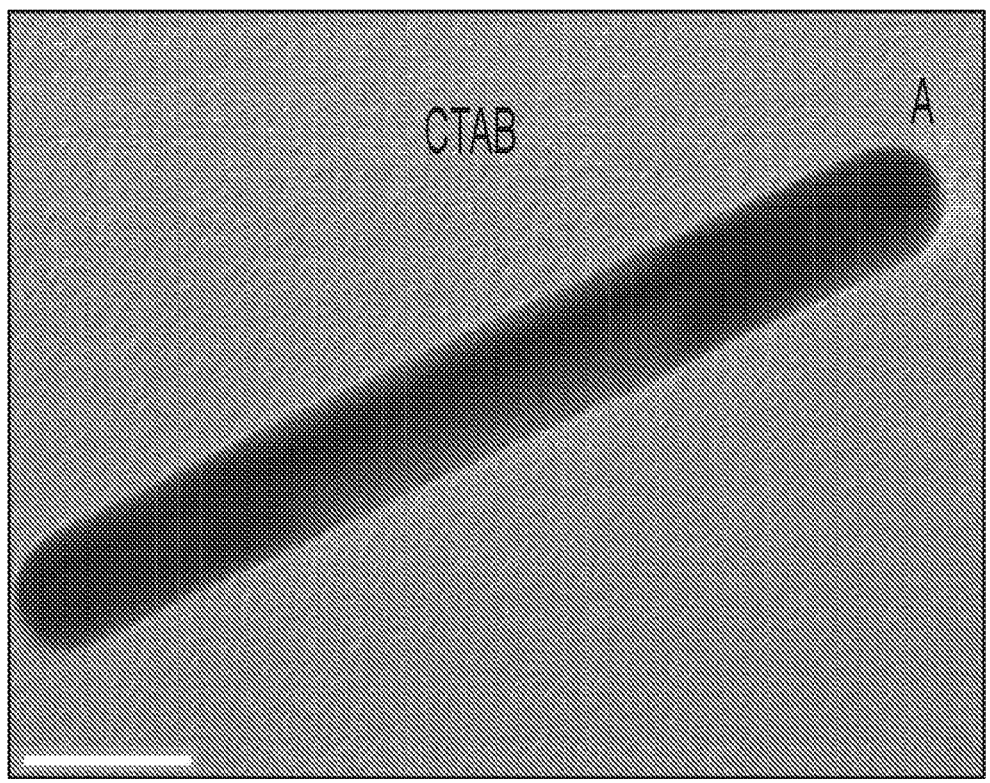
FIGS. 3A-3H present high-resolution transmission electron micrographs (HRTEM) and Energy Dispersive X-ray Spectroscopy (EDS) of gold nanorods; all scale bars are 20 nm.
Figure 3B:
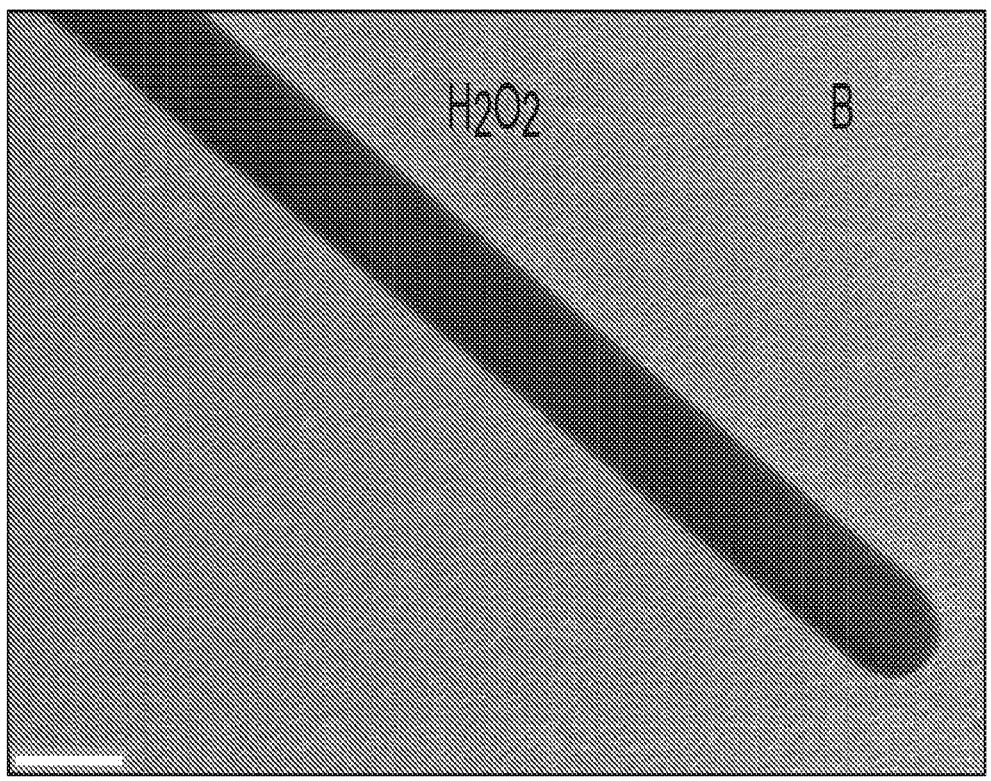
Figure 3C:
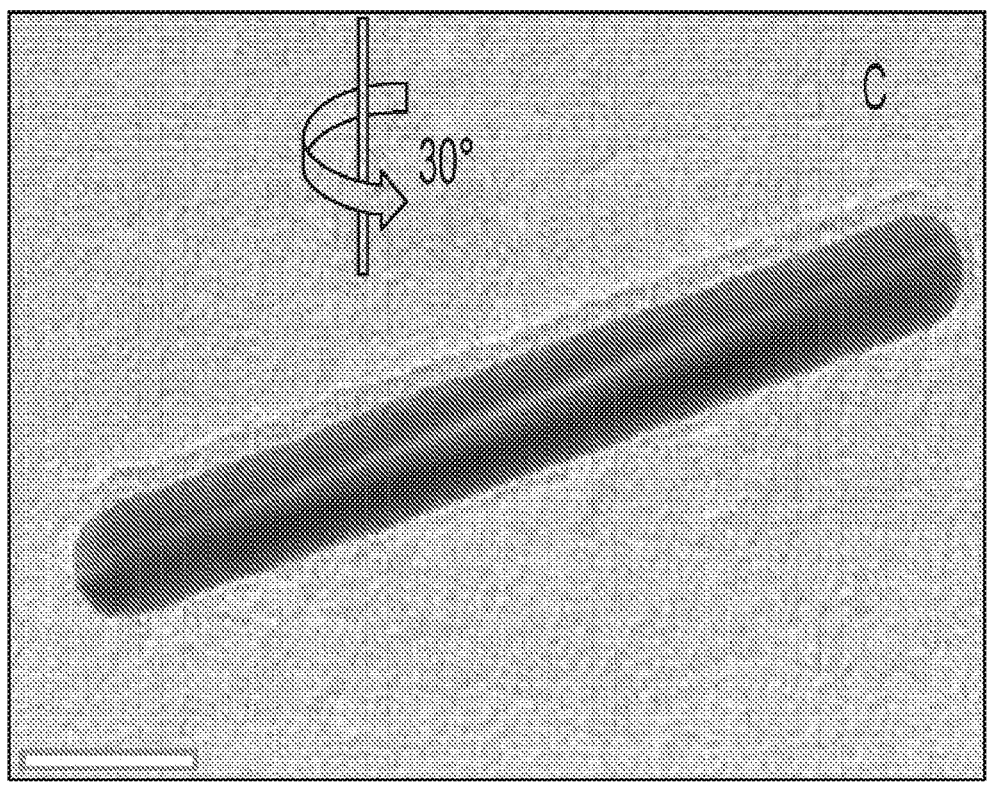
Figure 3D:
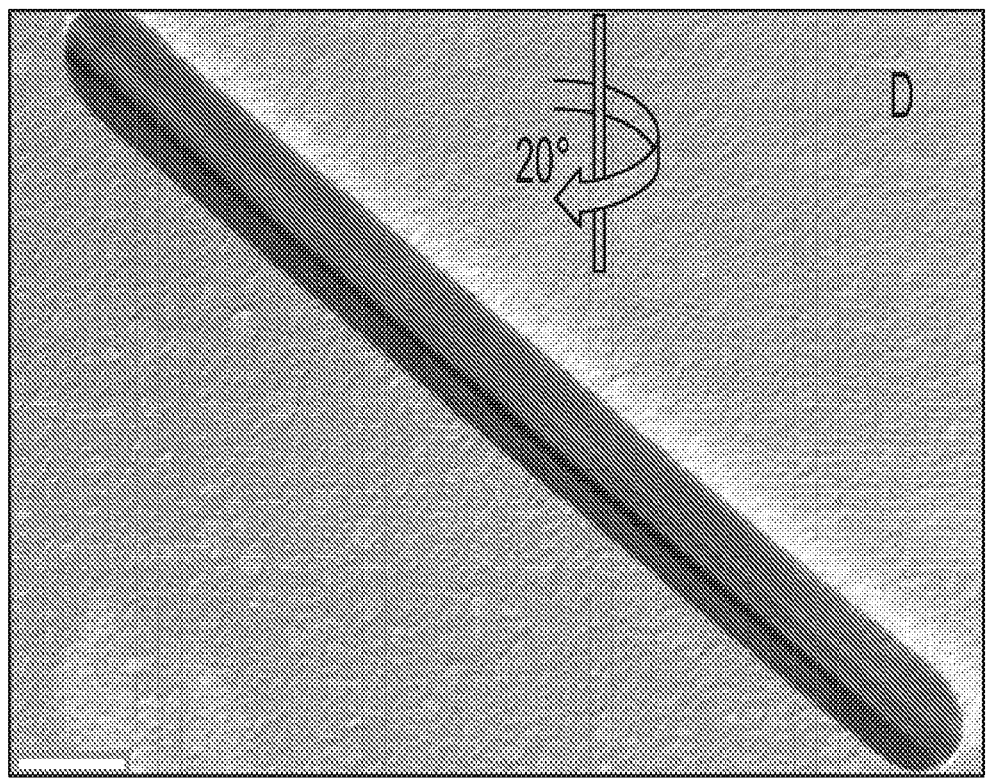
Figure 3E:
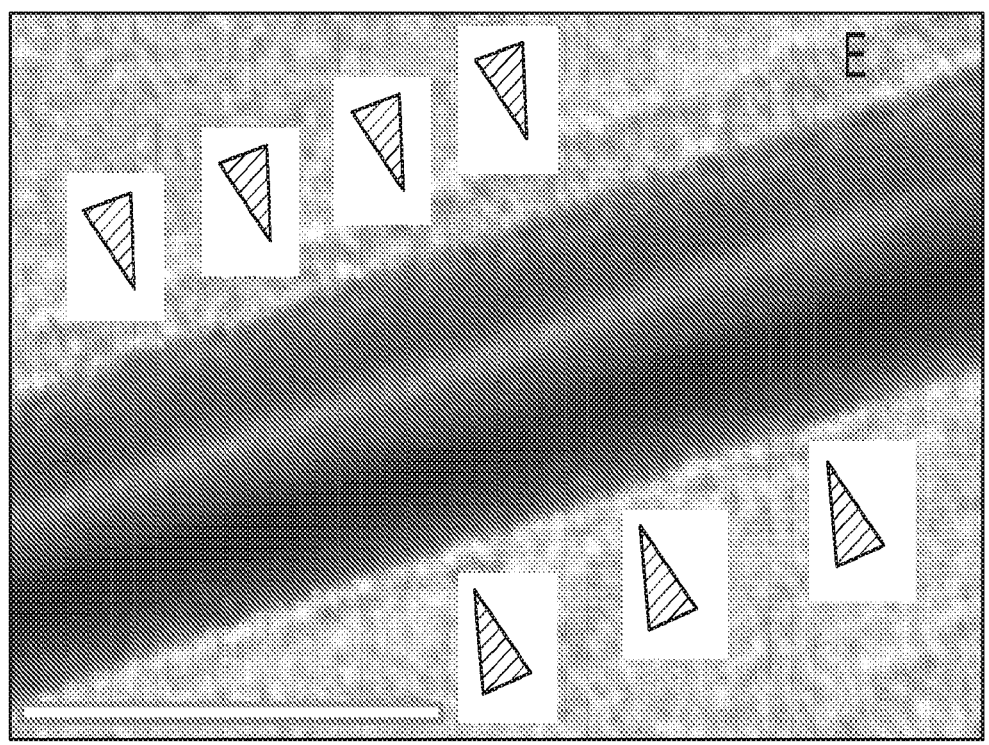
Figure 3F:
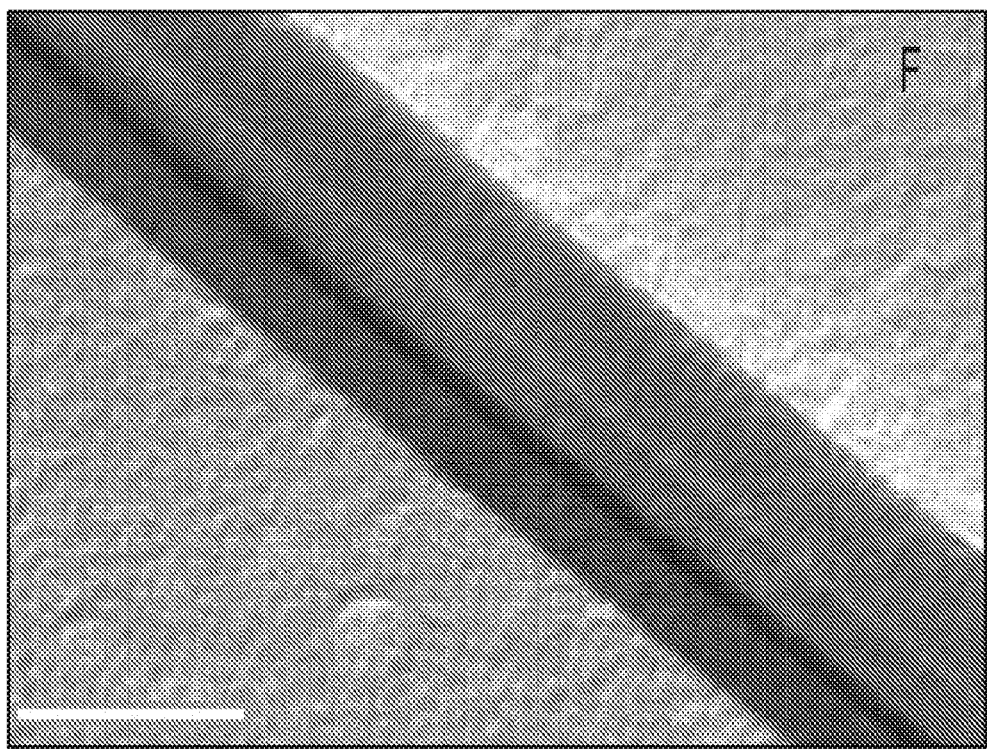
Figure 3G:
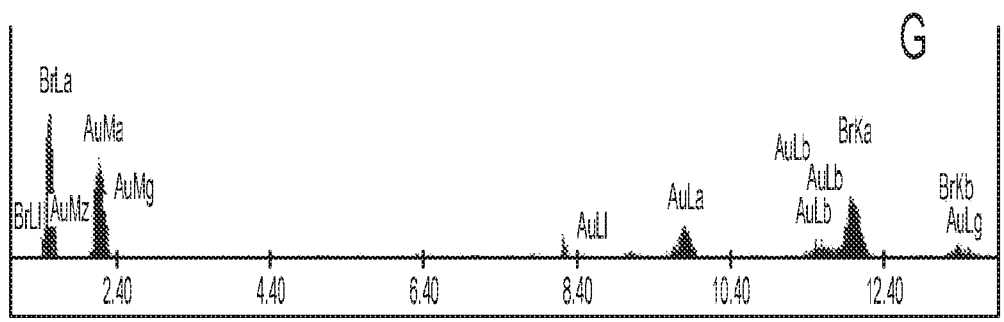
Figure 3H:
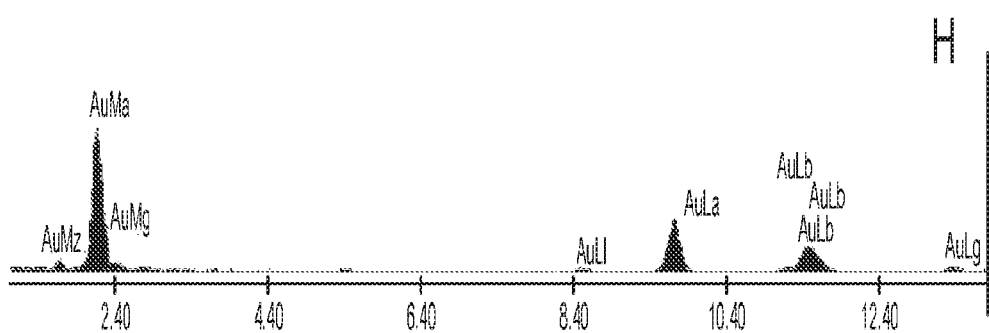

The surface of nanorods generated by the present method was analyzed for evidence of processes that influenced anisotropic growth. Energy dispersive x-ray spectroscopy (EDS) indicated that, unlike as would have been predicted based on prior art reports, no surface-blocking species are present on surface of nanorods prepared as described herein (FIG. 3F). Thus, the present invention provides novel nanorod compositions comprising nanorods substantially free of surface blocking species. Furthermore, the teachings of the present disclosure imply that nanorod synthesis using provided technologies utilizes a mechanism independent of facet-selective chemisorption. Thus, the present invention surprisingly provides technologies for anisotropic nanoparticle synthesis that do not require surface-blocking species; in some embodiments, provided methods do not utilize such species and provided nanoparticle compositions are substantially free of them.

Thus, the present Example describes production of gold nanoparticles with finely controlled shapes and sizes, synthesized by an inexpensive, green synthesis amenable to large-scale production. Unlike conventional methods that attempt to direct anisotropic GNP growth by means of facet-blocking additives, the present invention achieves shape control through a balance of growth and etching. Nanorods generated by methods described herein have the same morphology as those produced by the common Ag-free CTAB-mediated synthesis, suggesting that the same principles dictate anisotropic growth in both syntheses. However, nanoparticles produced by provided methods have surfaces that are not passivated by bulky stabilizing agents, making them ideal for surface-dependent applications like catalysis, SERS, and Localized Surface Plasmon Resonance sensing. The present invention therefore provides technologies and compositions particularly useful in such applications.

Materials and Methods:
Reagents
$H_2O_2$: Fluka 95321-100 ML Hydrogen peroxide solution 30%
$HAuCl_4$: Aldrich 520918-5G Gold(III) chloride trihydrate
NaOH: Sigma-Aldrich 55881-500G Sodium Hydroxide
$NaBH_4$: Fluka 71321-25G Sodium borohydride
PVP: Sigma-Aldrich PVP10-100G Polyvinylpyrrolidone
CTAB: Sigma H9151-25G Hexadecyltrimethylammonium bromide
Citrate: Sigma-Aldrich 54641-500G Sodium citrate tribasic dehydrate Synthesis of 3 nm Gold Nanoparticle Seeds—

100 µl of 25.4 mM $HAuCl_4$ was added to 10 mL of Millipore $H_2O$. 300 µL of 100 mM ice-cold $NaBH_4$ was added to this solution under vigorous stirring, which resulted in the immediate appearance of an orange-brown color. 41.6 mL of Millipore $H_2O$ was then added to achieve a 5× dilution. These seeds were used in all reactions without further treatment, though it was observed that neither the presence of citrate nor the removal of unreacted ions prevented the growth of any specific morphology.

Synthesis of 18 nm Gold Nanoparticle Seeds—

20 mL of $HAuCl_4$ was brought to a rolling boil under vigorous stirring. 2 mL of 1% (w/v) Sodium Citrate Tribasic was added to this solution and allowed to stir until a ruby-red color appeared. The mixture was allowed to cool to room temperature and the nanoparticles were washed once by centrifugation and re-suspended in 22 mL of Millipore $H_2O$.

Representative Protocols:

Nanoplates—

150 µL of as-prepared 3 nm seeds were added to 10 mL of Millipore $H_2O$. 150 µL of 25.4 mM $HAuCl_4$ was added, and the mixture was left undisturbed for 15 minutes. The reaction was then initiated by the addition of 100 µL of 0.3% $H_2O_2$ under stirring.

Nanorods—

1.5 mL of as-prepared 3 nm seeds were added to 8.50 mL of Millipore $H_2O$. 30 µL of 30% $H_2O_2$ was added to this mixture, and the reaction was initiated by the addition of 150 µL of 25.4 mM $HAuCl_4$ under vigorous stirring.

Nanorods (18 nm Seeds)—

300 µL of as-prepared 18 nm seeds were added to 9.70 mL of Millipore $H_2O$. 300 µL of 30% $H_2O_2$ was added to this mixture, and the reaction was initiated by the addition of 500 µL of 25.4 mM $HAuCl_4$ under vigorous stirring.

Nanostars—

150 µL of as-prepared 3 nm seeds were added to 9.85 mL of ice-cold Millipore $H_2O$. 150 µL of 25.4 mM $HAuCl_4$ was added to this mixture, and the reaction was initiated by adding a solution of 50 µL 1 M NaOH dissolved in 1 mL of 0.3% $H_2O_2$.

Thus, the present invention provides, and the present Example exemplifies, technologies that permit synthesis of monodisperse preparations of differently shaped gold nanoparticle cores (discs, plates, rods, spheres, squares, stars, etc., and particularly plates, rods, and/or stars) using different ratios of the same chemicals—specifically, gold chloride, hydrogen peroxide, water, and in some cases sodium hydroxide. The present invention provides, among other things, methods of performing such synthesis, compositions of nanoparticle cores prepared by such synthesis, as well as sets of reagents useful in such synthesis. In addition, the present invention provides methods for precisely controlling the shapes and sizes of the produced nanoparticles.

REFERENCES AND NOTES

1. B. K. Min, C. M. Friend, *Chem Rev* 107, 2709 (June, 2007).
2. K. M. Mayer, J. H. Hafner, *Chem Rev* 111, 3828 (June, 2011).
3. C. E. Talley et al., *Nano Lett* 5, 1569 (August, 2005).
4. W. L. Barnes, A. Dereux, T. W. Ebbesen, *Nature* 424, 824 (Aug. 14, 2003).
5. M. F. Kircher et al., *Nat Med* 18, 829 (May, 2012).
6. G. F. Paciotti et al., Drug Deliv 11, 169 (May-June, 2004).
7. K. L. Kelly, E. Coronado, L. L. Zhao, G. C. Schatz, *J Phys Chem B* 107, 668 (Jan. 23, 2003).
8. S. S. Shankar et al., *Nat Mater* 3, 482 (July, 2004).
9. M. L. Personick, M. R. Langille, J. Zhang, C. A. Mirkin, *Nano Lett* 11, 3394 (August, 2011).
10. P. S. Kumar, I. Pastoriza-Santos, B. Rodriguez-Gonzalez, F. J. Garcia de Abajo, L. M. Liz-Marzan, *Nanotechnology* 19, (Jan. 9, 2008).
11. M. Tsuji et al., *Colloid Surface A* 302, 587 (Jul. 20, 2007).
12. N. R. Jana, L. Gearheart, C. J. Murphy, *J Phys Chem B* 105, 4065 (May 17, 2001).
13. Y. G. Sun, Y. N. Xia, *Science* 298, 2176 (Dec. 13, 2002).
14. T. Niidome et al., *J Control Release* 114, 343 (Sep. 12, 2006).
15. Y. N. Xia, Y. J. Xiong, B. Lim, S. E. Skrabalak, *Angew Chem Int Edit* 48, 60 (2009).
16. A. R. Tao, S. Habas, P. D. Yang, *Small* 4, 310 (March, 2008).
17. J. Perez-Juste, L. M. Liz-Marzan, S. Carnie, D. Y. C. Chan, P. Mulvaney, *Adv Funct Mater* 14, 571 (Jim, 2004).
18. D. Seo et al., *JPhys Chem C* 112, 2469 (Feb. 21, 2008).
19. T. S. Sreeprasad, A. K. Samal, T. Pradeep, *Langmuir* 23, 9463 (Aug. 28, 2007).
20. K. Paclawski, K. Fitzner, Metall *Mater Trans B* 37, 703 (October, 2006).
21. L. L. Zhao et al., *J Phys Chem C* 113, 16645 (Sep. 24, 2009).
22. C. Lofton, W. Sigmund, *Adv Funct Mater* 15, 1197 (July, 2005).
23. Sun Y G, Xia Y N. Shape-controlled synthesis of gold and silver nanoparticles. *Science* 2002, 298(5601): 2176-2179.
24. Xia Y N, Xiong Y J, Lim B, Skrabalak S E. Shape-Controlled Synthesis of Metal Nanocrystals: Simple Chemistry Meets Complex Physics? *Angew Chem Int Edit* 2009, 48(1): 60-103.
25. Murphy C J, San T K, Gole A M, Orendorff C J, Gao J X, Gou L, et al. Anisotropic metal nanoparticles: Synthesis, assembly, and optical applications. *J Phys Chem B* 2005, 109(29): 13857-13870.
26. Grochola G, Snook I K, Russo S P. Computational modeling of nanorod growth. *Journal of Chemical Physics* 2007, 127(19): 13.
27. Kolb D M. Reconstruction phenomena at metal-electrolyte interfaces. *Progress in Surface Science* 1996, 51(2): 109-173.
28. Burton W K, Cabrera N, Frank F C. THE GROWTH OF CRYSTALS AND THE EQUILIBRIUM STRUCTURE OF THEIR SURFACES. *Philosophical Transactions of the Royal Society of London Series a-Mathematical and Physical Sciences* 1951, 243(866): 299-358.
29. Sugimoto T. Formation of monodispersed nano- and micro-particles controlled in size, shape, and internal structure. *Chem Eng Technol* 2003, 26(3): 313-321.
30. Bogels G, Buijnsters J G, Verhaegen S A C, Meekes H, Bennema P, Bollen D. Morphology and growth mechanism of multiply twinned AgBr and AgCl needle crystals. *Journal of Crystal Growth* 1999, 203(4): 554-563.
31. Hamilton D R, Seidensticker R G. PROPAGATION MECHANISM OF GERMANIUM DENDRITES. *J Appl Phys* 1960, 31(7): 1165-1168.
32. Liu X Y, Boek E S, Briels W J, Bennema P. Prediction of Crystal-Growth Morphology Based on Structural-Analysis of the Solid-Fluid Interface. *Nature* 1995, 374 (6520): 342-345.
33. Gibbs J. *Elementary Principles in Statistical Mechanics*. Charles Scribner's Sons: New York, USA, 1902.
34. Edgar J A, McDonagh A M, Cortie M B. Formation of Gold Nanorods by a Stochastic "Popcorn" Mechanism. *Acs Nano* 2012, 6(2): 1116-1125.
35. Almora-Barrios N, Novell-Leruth G, Whiting P, Liz-Marzan L M, Lopez N. Theoretical Description of the Role of Halides, Silver, and Surfactants on the Structure of Gold Nanorods. *Nano Lett* 2014, 14(2): 871-875.
36. Wulff G. On the question of speed of growth and dissolution of crystal surfaces. *Z Krystallogr Mineral* 1901, 34(5/6): 449-530.
37. Kashchiev D. *Nucleation: Basic Theory with Applications*. Butterworth-Heinemann, 2000.
38. Smoluchowski R. Anisotropy of the electronic work function of metals. *Physical Review* 1941, 60(9): 661-674.
39. Mamatkulov M, Filhol J S. Intrinsic Electrochemical and Strain Effects in Nanoparticles. *Journal of Physical Chemistry C* 2013, 117(5): 2334-2343.
40. Milek T, Zahn D. Molecular Simulation of Ag Nanoparticle Nucleation from Solution: Redox-Reactions Direct the Evolution of Shape and Structure. *Nano Lett* 2014, 14(8): 4913-4917.
41. Berg W F. Crystal growth from solutions. *Proceedings of the Royal Society of London Series a-Mathematical and Physical Sciences* 1938, 164(A916): 0079-0095.
42. Sugimoto T. GROWTH-MECHANISM AND SIZE DISTRIBUTION OF AGBR TABULAR GRAINS. *Photographic Science and Engineering* 1984, 28(4): 137-145.
43. Yu S H, Liu B, Mo M S, Huang R I, Liu X M, Qian Y T. General synthesis of single-crystal tungstate nanorods/nanowires: A facile, low-temperature solution approach. *Adv Funct Mater* 2003, 13(8): 639-647.
44. Xia X H, Xie S F, Liu M C, Peng H C, Lu N, Wang J G, et al. On the role of surface diffusion in determining the shape or morphology of noble-metal nanocrystals. *Proceedings of the National Academy of Sciences of the United States of America* 2013, 110(17): 6669-6673.
45. DuChene J S N, W.; Abendroth, J. M.; Sun, Q.; Zhao, W.; Huo, F.; Wei, W. D. Halide Anions as Shape-Directing Agents for Obtaining High-Quality Anisotropic Gold Nanostructures. *Chemistry of Materials* 2012, 25(8): 1392-1399.
46. Langille M R, Personick M L, Zhang J, Mirkin C A. Defining Rules for the Shape Evolution of Gold Nanoparticles. *J Am Chem Soc* 2012, 134(35): 14542-14554.
47. Mesgar M, Kaghazchi P, Jacob T, Pichardo-Pedrero E, Giesen M, Pichardo-Pedrero E, et al. Chlorine-Enhanced Surface Mobility of Au(100). *ChemPhysChem* 2013, 14(1): 233-236.
48. Myersbeaghton A K, Vvedensky D D. GENERALIZED BURTON-CABRERA-FRANK THEORY FOR GROWTH AND EQUILIBRATION ON STEPPED SURFACES. *Physical Review A* 1991, 44(4): 2457-2468.
49. Wang Y, Peng H C, Liu J Y, Huang C Z, Xia Y N. Use of Reduction Rate as a Quantitative Knob for Controlling the Twin Structure and Shape of Palladium Nanocrystals. *Nano Lett* 2015, 15(2): 1445-1450.
50. Xiong Y J, Chen J Y, Wiley B, Xia Y N, Aloni S, Yin Y D. Understanding the role of oxidative etching in the polyol synthesis of Pd nanoparticles with uniform shape and size. *J Am Chem Soc* 2005, 127(20): 7332-7333.
51. Lee, I., Delbecq, F., Morales, R., Albiter, M. A. & Zaera, F. Tuning selectivity in catalysis by controlling particle shape. *Nat. Mater.* 8, 132-138 (2009).
52. Andoy, N. M. et al. Single-Molecule Catalysis Mapping Quantifies Site-Specific Activity and Uncovers Radial Activity Gradient on Single 2D Nanocrystals. *J. Am. Chem. Soc.* 135, 1845-1852 (2013).
53. Xu, H. X., Aizpurua, J., Kall, M. & Apell, P. Electromagnetic contributions to single-molecule sensitivity in surface-enhanced Raman scattering. *Phys. Rev. E* 62, 4318-4324 (2000).
54. Jain, P. K., Huang, X. H., El-Sayed, I. H. & El-Sayed, M. A. Noble Metals on the Nanoscale: Optical and Photothermal Properties and Some Applications in Imaging, Sensing, Biology, and Medicine. *Acc. Chem. Res.* 41, 1578-1586 (2008).
55. Harmsen, S. et al. Surface-enhanced resonance Raman scattering nanostars for high-precision cancer imaging. *Sci. Transl. Med.* 7, 11 (2015).
56. Wang, S. et al. A highly efficient, clean-surface, porous platinum electrocatalyst and the inhibition effect of surfactants on catalytic activity. *Chemistry* 19, 240-8 (2013).
57. Wang, T., Hu, X. & Dong, S. Surfactantless Synthesis of Multiple Shapes of Gold Nanostructures and Their Shape-Dependent SERS Spectroscopy. *J. Phys. Chem. B* 110, 16930-16936 (2006).
58. Caswell, K. K., Bender, C. M. & Murphy, C. J. Seedless, Surfactantless Wet Chemical Synthesis of Silver Nanowires. *Nano Lett.* 3, 667-669 (2003).
59. Daniel, M. C. & Astruc, D. Gold nanoparticles: Assembly, supramolecular chemistry, quantum-size-related properties, and applications toward biology, catalysis, and nanotechnology. *Chem. Rev.* 104, 293-346 (2004).
60. Sugimoto, T. PREPARATION OF MONODISPERSED COLLOIDAL PARTICLES. *Adv. Colloid Interface Sci.* 28, 65-108 (1987).
61. Markov, I. V. *Crystal Growth for Beginners: Fundamentals of Nucleation, Crystal Growth, and Epitaxy*. (World Scientific: Singapore, 2003).
62. Kossel, W. Extending the Law of Bravais. *Nachr. Ges. Wiss. Gottingen* 135, 135-143 (1927).
63. Stranski, I. N. On the theory of crystal accretion. *Zeitschrift Fur Phys. Chemie—Stochiometrie Und Verwandtschaftslehre* 136, 259-278 (1928).
64. Kleiner A; Naderian, M; Mueller, J; Fantauzzi, D; Mesgar, M; Keith, J; Anton, J; Jacob, T, K. C.-V. Multiscale Modeling of Au-Island Ripening on Au(100). *Adv. Phys. Chem.* 2011, (2011).
65. Stoltze, P. SIMULATION OF SURFACE-DEFECTS. *J. Physics—Condensed Matter* 6, 9495-9517 (1994).
66. Bockris, J. O. & Oldfield, L. F. The oxidation-reduction reactions of hydrogen peroxide at inert metal electrodes and mercury cathodes. *Trans. Faraday Soc.* 51, 249-259 (1955).
67. Johnson, C. J., Dujardin, E., Davis, S. A., Murphy, C. J. & Mann, S. Growth and form of gold nanorods prepared by seed-mediated, surfactant-directed synthesis. *J. Mater. Chem.* 12, 1765-1770 (2002).
68. Tadjiki, S. ANYL 292-Preparative scale separation of nanoparticles using centrifugal SPLITT. *Abstr. Pap. Am. Chem. Soc.* 238, (2009).
69. Kirkland, A. I. et al. STRUCTURAL STUDIES OF TRIGONAL LAMELLAR PARTICLES OF GOLD AND SILVER. *Proc. R. Soc. London Ser. a-Mathematical Phys. Eng. Sci.* 440, 589-609 (1993).

Example 2: Removing Residual Chemical Species

In some embodiments, the present invention provides methodologies for preparing anisotropic nanoparticle cores (e.g., gold cores) that involve performing specific steps to remove residual chemical species. In some such embodiments, resulting nanoparticle compositions are substantially free of components such as halide ions, metal ions, oxidative species, and unreacted reagents, and combinations thereof; in some such embodiments, resulting nanoparticle compositions consist essentially of nanoparticles (e.g., nanoparticle cores) and water.

The present disclosure provides various different strategies for removing chemical species (e.g., unreacted species) from nanoparticle synthesis compositions, including both washing and dialysis technologies, as described below for nanostar preparation:

Washing—

Immediately after nanostars were synthesized, they were diluted to 150% of their original volume by the addition of ice-cold Millipore $H_2O$. The solution was then split into two separate centrifuge tubes and spun down for the minimal amount of time necessary to collect nanostars at the bottom of the tube at 8000 rpm (e.g., 4 minutes for 1 mL). The supernatant was removed, and a small volume of ice-cold Millipore $H_2O$ was added in order to enable effective redispersion of the nanostars via ultrasonication. Finally, the original reaction volume was obtained by dilution with ice-cold Millipore $H_2O$.

It was found that repeating this process multiple times resulted in aggregation, however it is very difficult to remove all residual reagent traces in one wash, thus shape-transformation is not prevented indefinitely by this method.

Dialysis—

Immediately after nanostars were synthesized, they were added to a 2,000 MWCO Slide-A-Lyzer dialysis cassette that was then placed into a large volume of Millipore $H_2O$ and subjected to slow stirring. The dialysis water was replaced periodically until residual chemical species were removed. After investigating the nanoparticle surface, no impurities were revealed to be present on the nanoparticle surface to suggest that cassette-particle stabilizing interactions (e.g., membrane leaching) occurred.

Example 3: Framework for Selecting Conditions to Achieve Particular Anisotropic Structures The present Example includes an analysis of the role of oxidative etching in growth of nanoparticle core structures from seeds, and provides a framework for selecting conditions to achieve production of particular desired anisotropic structures.

Some conventional methods have employed oxidative etching in order to achieve anisotropic growth. In general, utilized strategies involved either etching the small nanoparticle seeds so that only certain populations (e.g., single crystalline or single-twinned) remain, or blocking specific facets with surface passivating agents and then preferentially etching the unblocked facets. While these methods have proved effective in achieving some degree of shape control, they did not provide a thorough understanding or teaching of the effect that oxidative etching can have on nanoparticle formation. For example, the extent to which a non-passivated nanoparticle is affected by oxidative etching during synthesis has not been previously explored. Some aspects of the present invention encompass the recognition that this question represents an especially important unanswered issue in nanoparticle synthesis because many of the shape-controlled synthesis routes employ materials capable of oxidizing gold nanoparticles (e.g., even $HAuCl_4$ and $O_2$ in the presence of can etch nanoparticles). Furthermore, the ubiquitous CTAB synthesis incorporates very large concentrations of $Br^-$ and $CTA^+$, both of which stabilize $Au^+$, and therefore facilitate etching.

Without wishing to be bound by any particular theory, the present invention observes that oxidative etching is most likely to occur at the highly susceptible twin-boundaries. As this proceeds, there is a redistribution of surface area around the nanoparticle. Increased etching from an idealized decahedral seed results in a transition from a morphology with pentagonally twinned "ends" constituting all of the surface area to a rod-like particle with the majority of its surface area on side facets. As gold atoms add to this particle, monolayers would be expected to form fastest on the facets with the smallest surface area. This phenomenon imparts an increased growth rate at the end facets. Growth outward from the ends becomes progressively more favored as the ratio of side-facet surface area to end-facet surface area increases.

Structural and thermodynamic factors are also expected to contribute to activating one-dimensional growth. Large re-entrant grooves etched into a multiply twinned nanoparticle seed is likely to prevent transformation into a single crystalline seed. This would shift the equilibrium of crystallinity fluctuation to favor multiply twinned seeds. Additionally, it is widely accepted that the strain at twin boundaries of a pentagonally twinned nanoparticle should favor growth along the fivefold axis. This effect may be magnified in the presence of major grooves. Future simulations investigating the strain and surface charge distribution around a nanoparticle with major re-entrant grooves should reveal deeper insight into these and other effects favoring one-dimensional growth.

The present invention teaches that gold nanoplates, nanostars, and nanorods can be synthesized over a variety of conditions. Table 1 below indicates typical trends in the nanoparticle population as reaction conditions are varied:

TABLE 1

Trends in nanoparticle populations under different reaction conditions.

| $H_2O_2$ | $HAuCl_4$ | Seeds | NaOH | Plates | Rods | Spheres | Stars |
|---|---|---|---|---|---|---|---|
| 10 | 15 | 3 | 0 | Many | Few | Many | None |
| 100 | 15 | 3 | 0 | Many | Few | Many | None |
| 500 | 15 | 3 | 0 | Many | Few | Many | None |
| 10 | 15 | 15 | 0 | Many | Many | Many | None |
| 100 | 15 | 15 | 0 | Many | Many | Many | None |
| 500 | 15 | 15 | 0 | Many | Many | Many | None |
| 10 | 15 | 150 | 0 | Few | Many | Many | None |
| 100 | 15 | 150 | 0 | Few | Many | Many | None |
| 500 | 15 | 150 | 0 | Few | Many | Many | None |
| 100 | 15 | 3 | ≥2 | None | None | None | All |
| 100 | 15 | 15 | ≥2 | None | None | None | All |
| 100 | 15 | 150 | ≥2 | None | None | None | All |

In Table 1 above, the numerical values represent the volume in microliters of each reagent added to a 1 mL synthesis. $[H_2O_2]$=0.3% w/v (i.e., 1% v/v diluted from 30% stock), $[HAuCl_4]$=25.4 mM, [seeds]=as prepared. The presence of spheres (more properly, icosahedra and truncated icosahedra) in the reactions is a reflection of the fact that plates and rods form from singly or multiply twinned seeds, while spheres form from single crystalline seeds. As long as singly crystalline seeds were in solution, neither rods nor plates could be made with a 100% yield. Nanostars, however, can grow from any type of gold nanoparticle seed, so spheres were not observed in their syntheses (unless morphological transformation was allowed to proceed).

The present disclosure places these observations into a general framework of seed-mediated nanoparticle growth. The nanoparticle seeds present at the beginning of the reaction exist as a mixture of single crystalline, single-twinned, and multiply-twinned crystallinities that each have the potential to grow into distinct morphologies during the reduction of $HAuCl_4$. The icosahedra and decahedra present as byproducts grow from single crystalline seeds, the nanoplates are produced from single-twinned seeds, and the nanorods form from multiply twinned seeds. Under strong oxidative etching, the multiply-twinned seeds can be dissolved, leaving single-twinned and single crystalline seeds in higher ratios. This is why plates form in greater yields under highly oxidative conditions. Under moderately oxidative conditions, multiply-twinned seeds are not completely dissolved, but rather have grooves etched into the high-energy twin boundaries. This activates the seeds toward rod-like growth, explaining why nanorods require slightly less oxidative conditions than plates. Stars can be formed by branching from any type of seed, but require very rapid $HAuCl_4$ reduction. Thus, highly reductive conditions generate nanostars in virtually 100 percent morphological yield, despite growth from different seed crystallinities. In principal, the yield of a given morphology depends only on the percent of seeds that exist in the proper crystallinity, the amount of oxidative etching, and the rate of $HAuCl_4$ reduction.

Example 4: Multiplexed Imaging with Differently Shaped Nanoparticles

Differently shaped metallic nanoparticles as described herein can be used in any of a variety of applications. In some embodiments, provided differently shaped metallic nanoparticles can be used for multiplexed immunostaining on an electron microscope (e.g., using EM; transmission EM (TEM), scanning EM (SEM). Embodiments of the present invention in which silica coatings are applied to provided nanoparticle cores can add yet another level of multiplexing capability. In some embodiments, utilized preparations of nanoparticles comprise cores of the same shape coated with silica layers of different thicknesses; in some embodiments, utilized preparations of nanoparticles comprise cores of different shapes coated with silica layers of comparable or identical thickness; in some embodiments, utilized preparations of nanoparticles comprise cores of different shapes and silica layers of different thicknesses.

Among other things, EM multiplexing capabilities provided by and/or practiced in accordance with the present invention allow studying of relative expression and localization of targets of interest at the molecular (nano) level. For example, such capabilities add nanoscale dimensions to studies of protein-protein interactions, protein-antibody interactions, binding kinetics, etc., each of which can all be studied in real time.

Immunostaining by gold nanoparticle-antibody conjugates is a widely used technique to counterstain targets of interest. However, prior to the present invention, technologies had not been developed for identifying multiple targets in a TEM/SEM sample. The present invention, however, provides populations of differently-shaped and/or otherwise differentially detectable (e.g., by virtue of thickness of a coating such as a silica coating) nanoparticles. Those of ordinary skill in the art, reading this disclosure, will appreciate that such differentially detectable nanoparticles can be conjugated to ligands for (e.g., antibodies that bind specifically to) different targets of interest, and that populations of such differentially detectable, differently conjugated nanoparticles can be used to simultaneously or sequentially detect multiple targets in the same sample, site, or organism of interest. In some embodiments, expression and/or localization patterns (including relative expression levels in one or more locations and changes thereto that may occur over time) can be assessed.

Alternatively or additionally, conjugation of both members of an interacting pair (or multiple members of an interacting set) to differently detectable nanoparticles as provided by the present invention permits analysis of binding/assembly kinetics in real time, for example using a TEM.

Example 5: Exemplary Catalysis Reactions Using Anisotropic Nanoparticles

The present Example describes certain catalysis reactions utilizing anisotropic nanoparticles as described herein.

Figure 4:
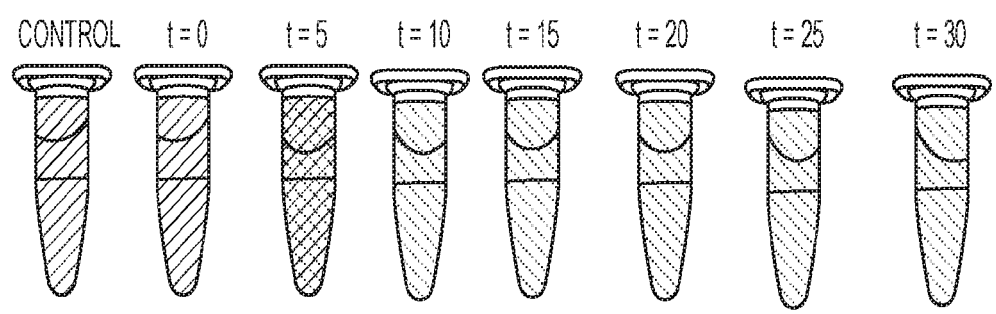
FIG. 4 illustrates conversion of resazurin to resarufin.

For example, FIG. 4 illustrates conversion of resazurin to resazurin. 25 µL of 5 mM resazurin was added to 375 µL of 0.25 nM gold nanostars in pH=7.3 MES buffer. At the indicated time points, 500 µL of pH=7.3 MES buffer was added to the reaction and the supernatant was isolated after centrifugation at 8,000 rpm for four minutes. The catalytic conversion of the weakly fluorescent, blue resazurin to the strongly fluorescent resarufin is easily followed by eye. The control of resazurin and hydroxylamine without gold nanostars does not react, even after several hours (shown on the left in FIG. 4). The reaction in the presence of gold nanostars was followed every five minutes after initiation and was observed to complete after 15 minutes.

Figure 5:
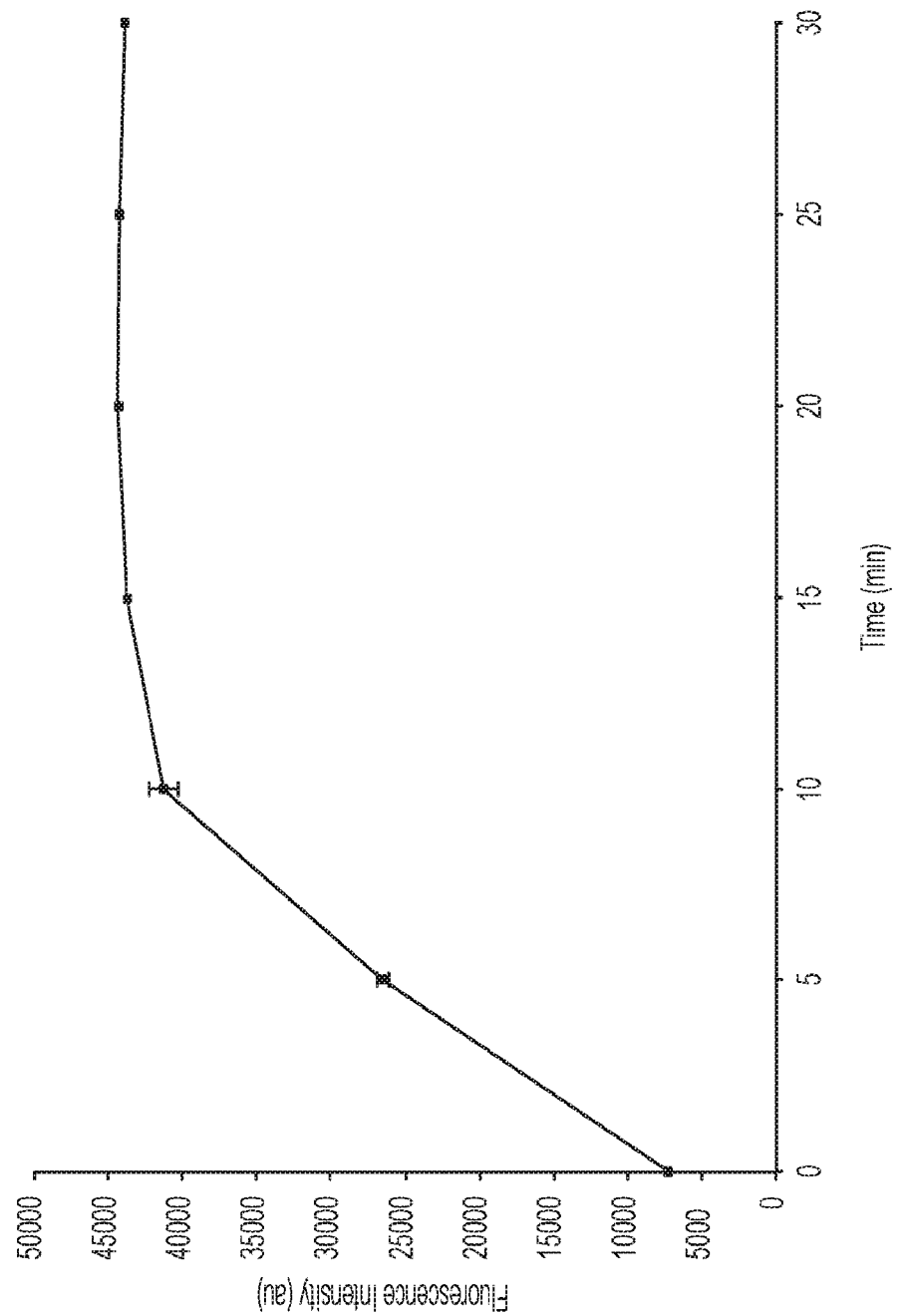
FIG. 5 depicts catalysis of resazurin and hydroxylamine in the presence of gold nanostars.
Figure 6:
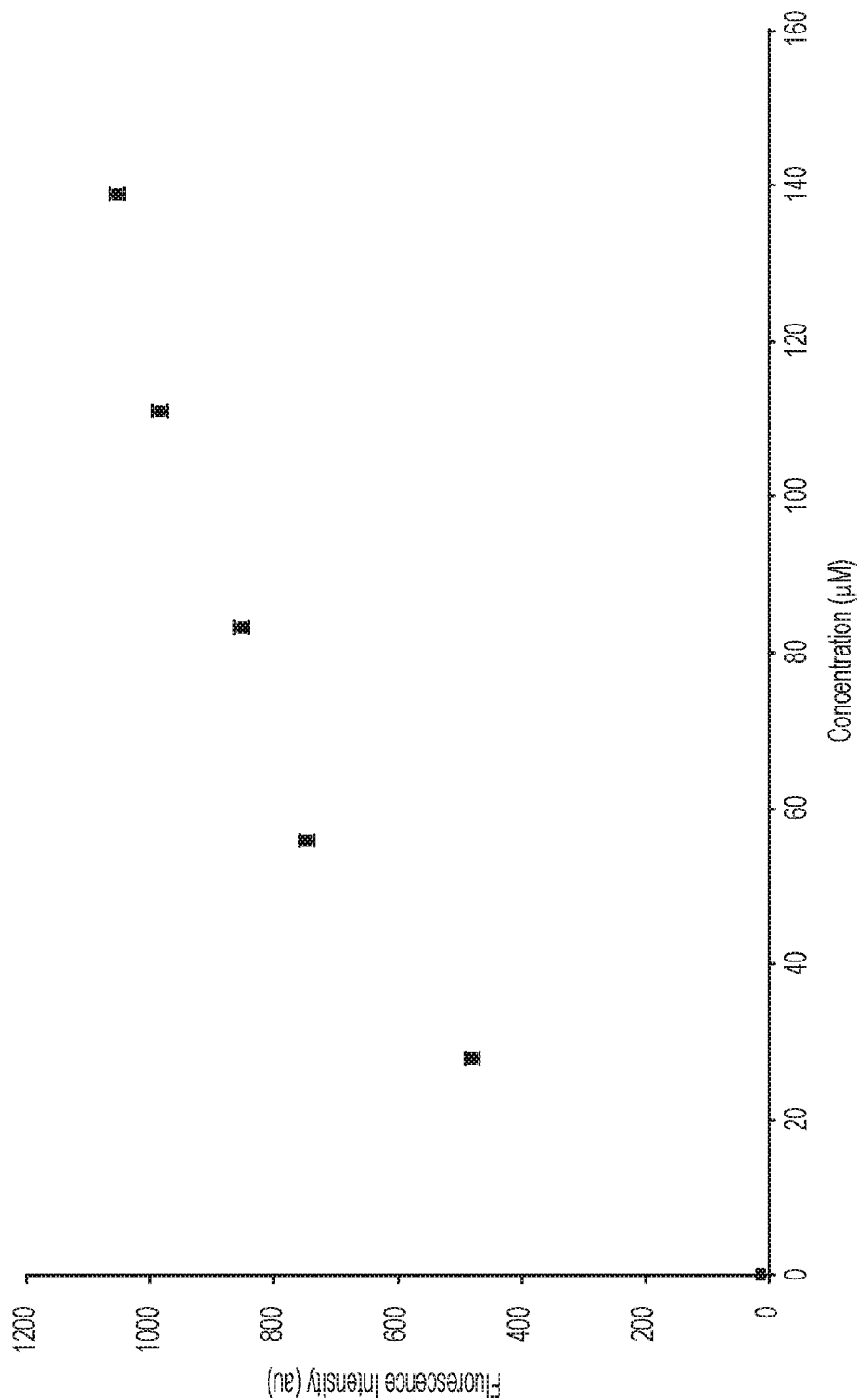
FIG. 6 presents a calibration curve for fluorescence intensity of resazurin versus concentration.
Figure 7:
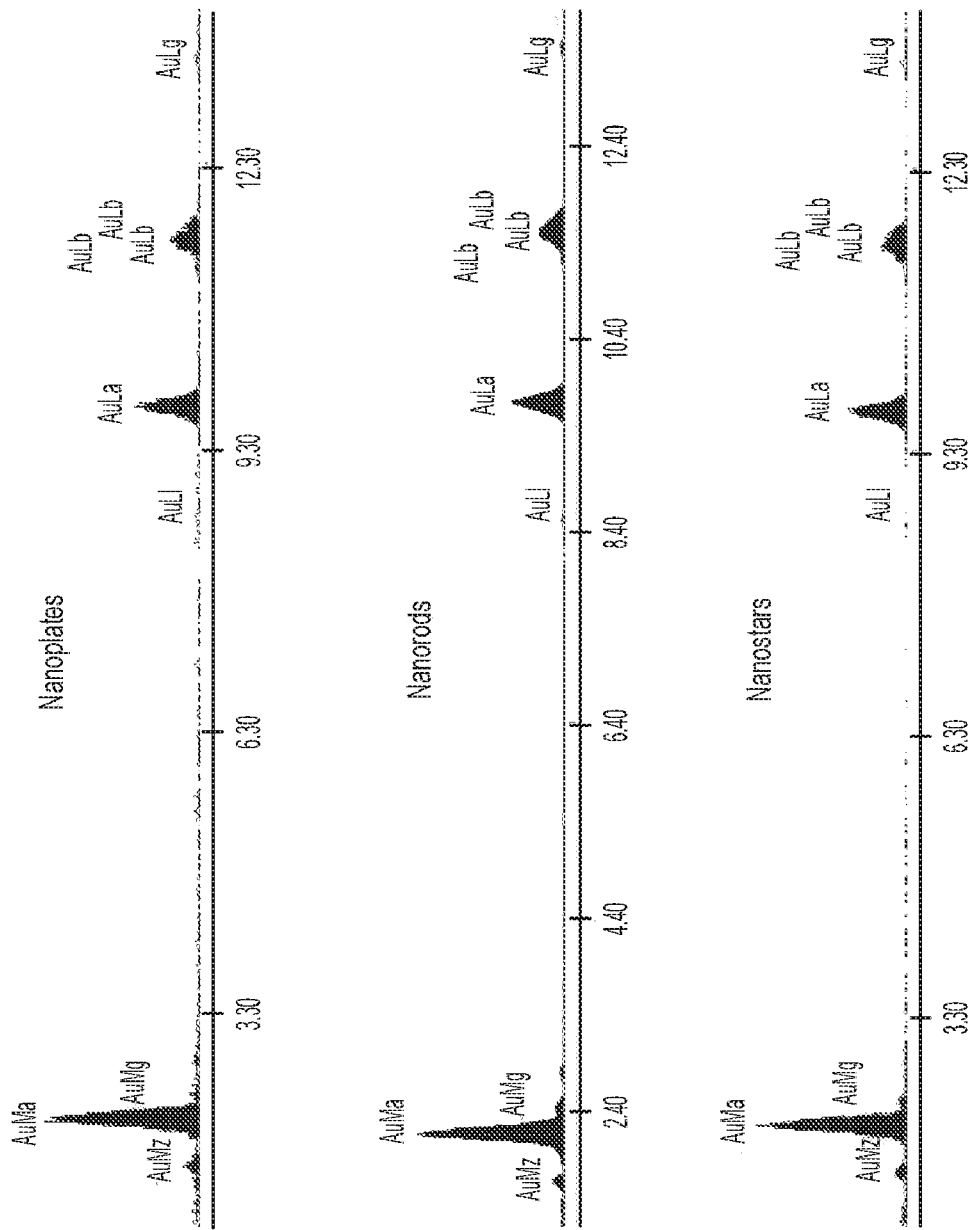
FIG. 7 shows energy dispersive x-ray spectra of gold nanoplates, nanorods, and nanostars. Only gold peaks are registered for all morphologies, indicating that capping-agent directed growth is unlikely.
Figure 8:
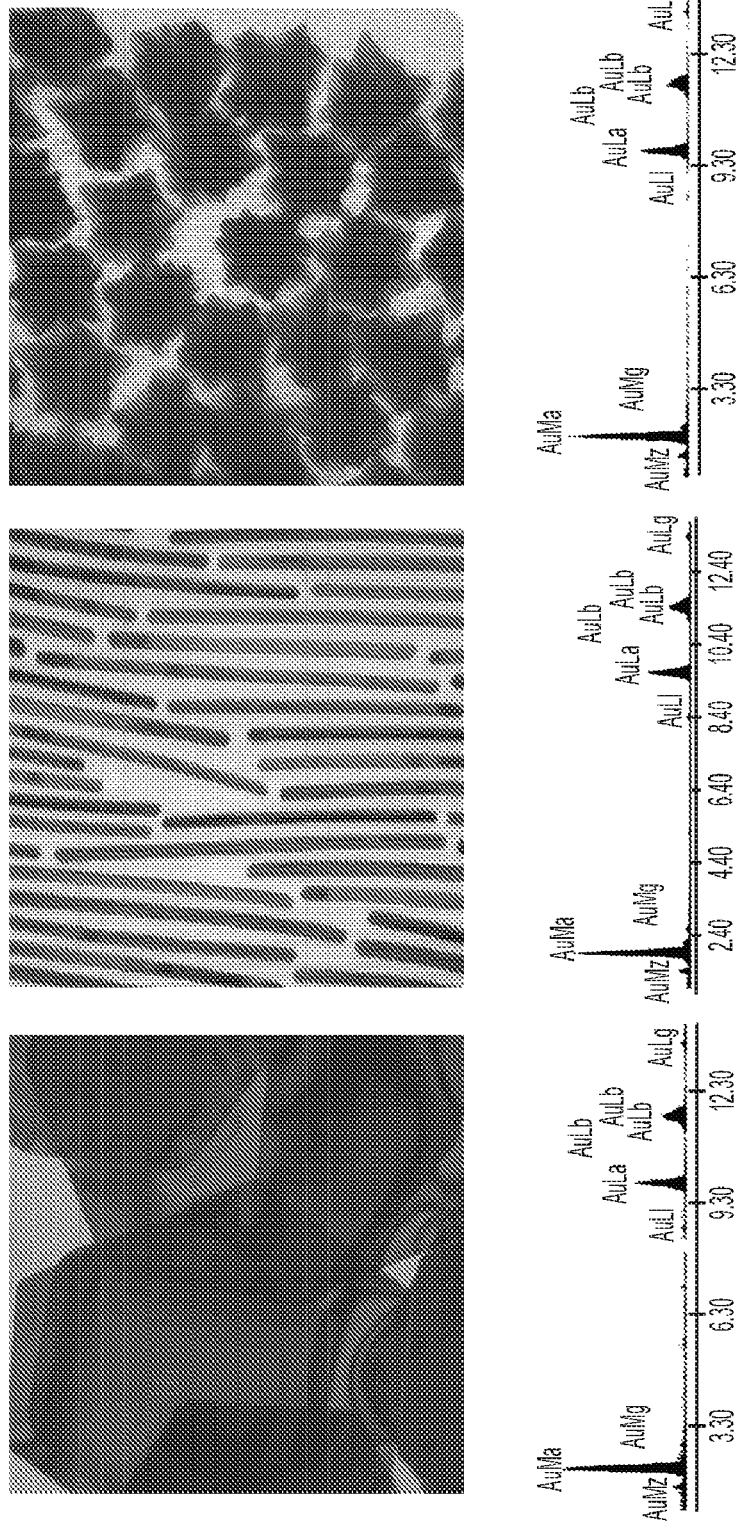
FIG. 8 presents dispersive x-ray spectra of gold nanoplates, nanorods, and nanostars. Only gold peaks are registered for all morphologies, indicating that capping-agent directed growth is unlikely.
Figure 9:
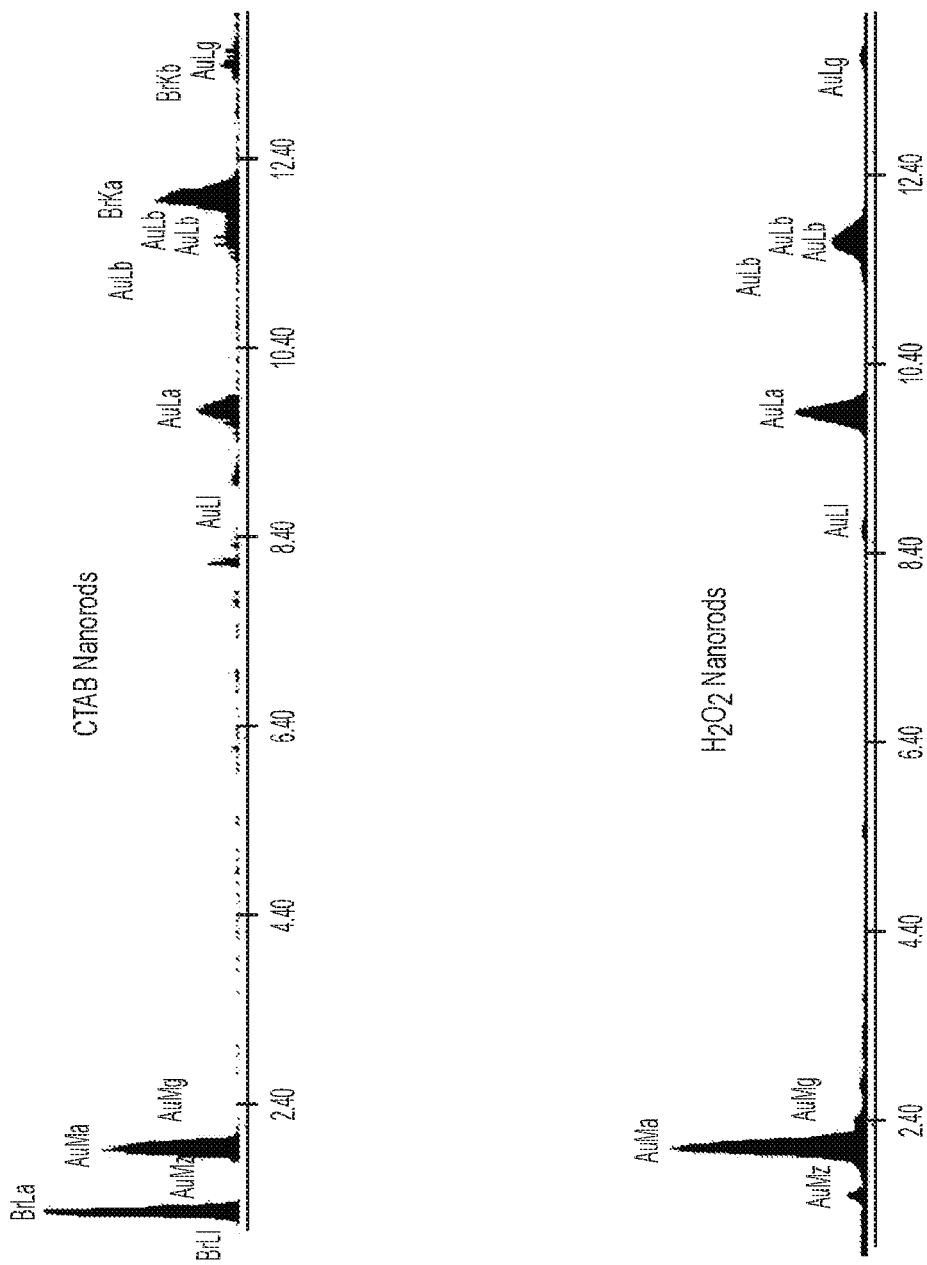
FIG. 9 shows energy dispersive x-ray spectra of gold nanorods prepared by the Ag-free CTAB-mediated method, and the hydrogen peroxide-mediated method. The CTAB particles were washed and the background counts were subtracted, indicating that the bromide peaks are coming from the nanoparticle surface. In contrast, the spectra of the nanorods from the peroxide-mediated synthesis demonstrate only Au peaks.
Figure 10:
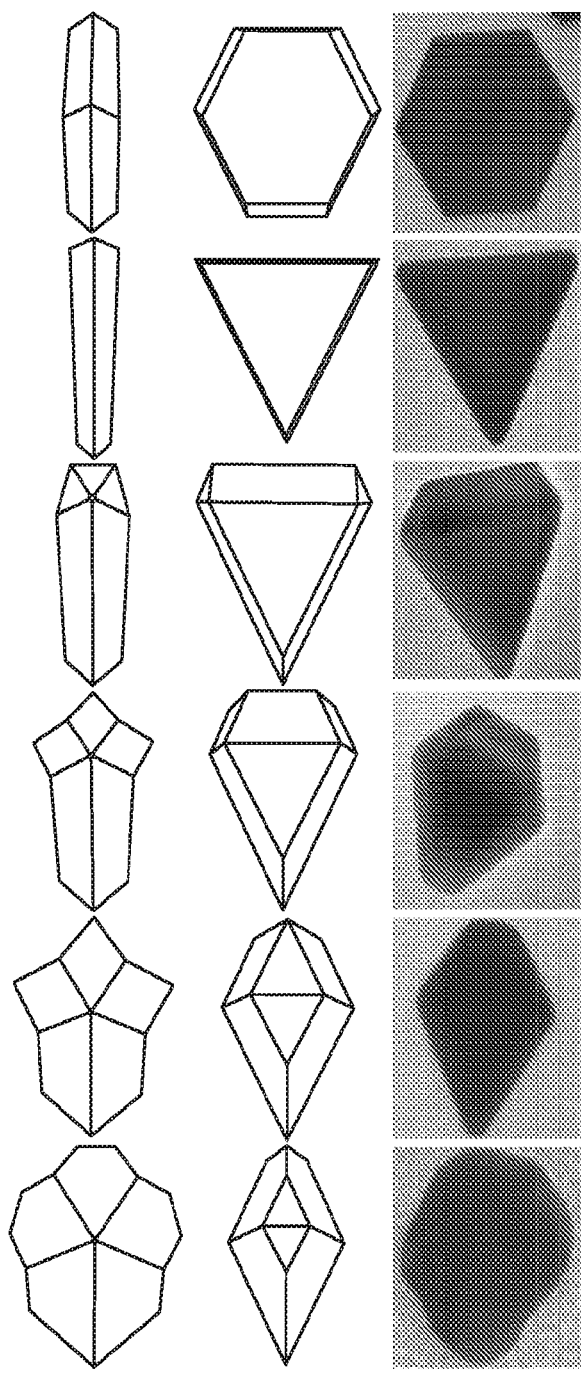
FIG. 10 presents images illustrating crystallographic growth mechanism of nanoplates. Eight distinct morphologies are presented which depict stages in the crystallographic mechanism of nanoplate formation. For each stage, a transmission electron micrograph (left) is provided, along with renderings representing the morphology as viewed from the side (middle) and top (right) of the pseudo-five-fold symmetry axis. This crystallographic mechanism can be explained by oxidative etching of one of the five twin boundaries proceeding more slowly than the other four, and thus resulting in an asymmetric extension of the nanoparticle parallel to a single twin plane. As the extent of etching increases among the four twin boundaries (1-6), the nanoparticle approaches a truncated bitetrahedral geometry (i.e., triangular nanoplate). All exposed facets of this geometry are {111}, and etching is most favored to proceed from the vertices inward because the vertices have the fewest neighboring atoms (i.e., are the least tightly bound to the particle surface) and their removal exposes {100} facets which oxidize more easily than {111}. As the triangular nanoplate etches inward from its edges (7 and 8), it approaches a hexagonal nanoplate geometry. Vertex etching can be continued further until pseudo-circular discs are formed. This crystallographic mechanism is probably complementary to other nanoplate growth mechanisms, rather than the exclusive route to their formation. Perhaps it is the explanation for the formation of singly-twinned seeds, which are employed in other growth mechanisms.
Figure 11:
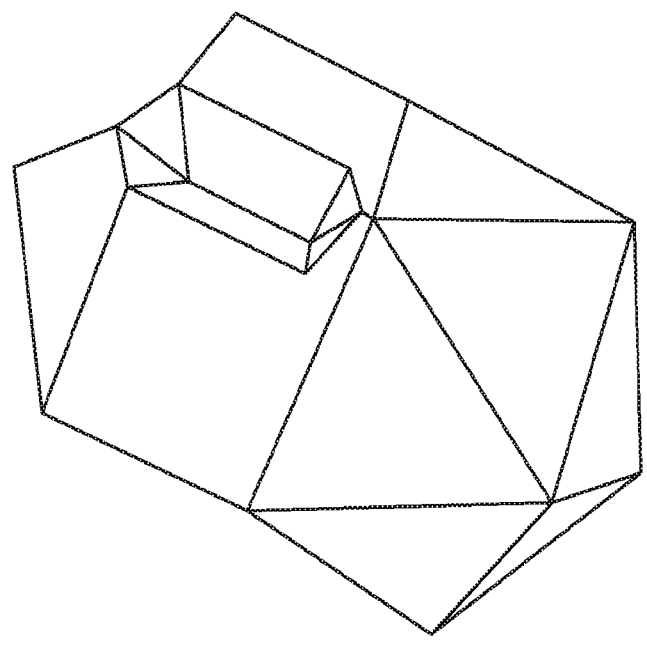
FIG. 11 presents HRTEM of partial nanorod. A nanoparticle possessing major grooves halfway down its longest axis demonstrates nanorod symmetry where the grooves are present and pseudo-icosahedral symmetry where the grooves are absent. This is a strong example of oxidative etching activating anisotropic growth. HRTEM is shown on the left with corresponding rendering on the right.
Figure 11:
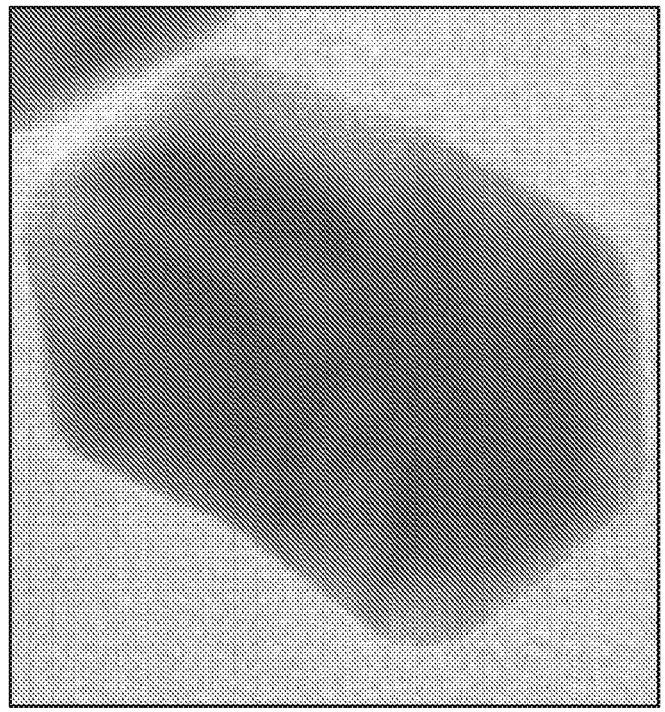
Figure 12:
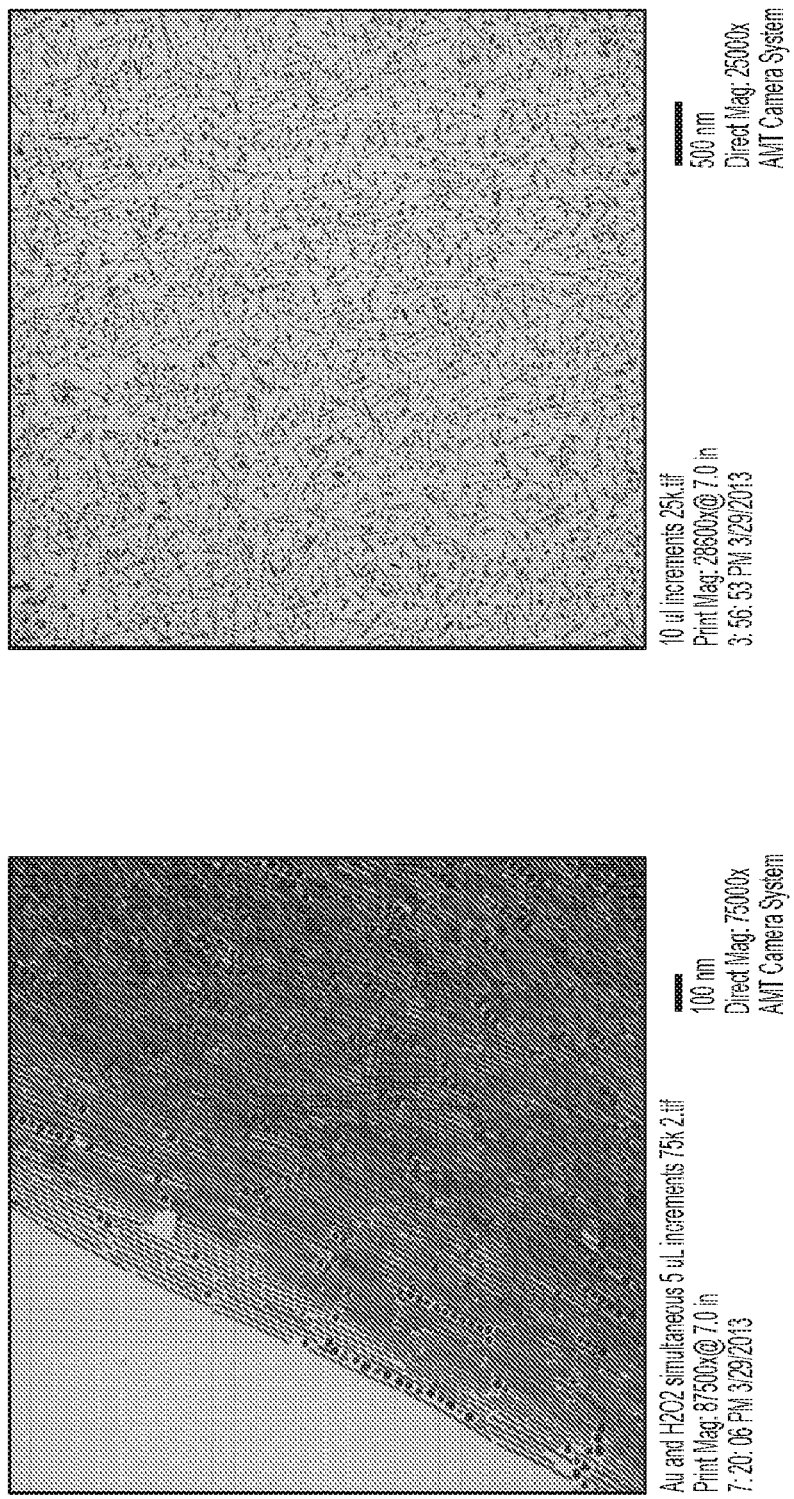
FIG. 12 shows images illustrating yield of nanorods. High aspect ratio nanorods were synthesized by adding 50 µL of 25 mM $HAuCl_4$ to a solution of 60 µL seeds and 3 µL 30% $H_2O_2$ in 1 mL $H_2O$. The $HAuCl_4$ was added in increments of 10 µL over the course of 10 min. In order to achieve particle separation sufficient for determining morphological yield, 300 µL of 2% PVP (MW10,000) was added to the nanoparticle mixture after the reaction had completed and the nanoparticles were centrifuged at 10000 rpm for 5 minutes then re-dispersed in water. Accurate quantification of morphological yield can be difficult because different shapes and sizes of nanoparticles have a tendency to accumulate in high concentrations at certain locations and low concentrations at others (e.g., nanorods and nanoplates appear in high concentration at the edges of the evaporated sample region). The scale bar is 2 microns.
Figure 13:
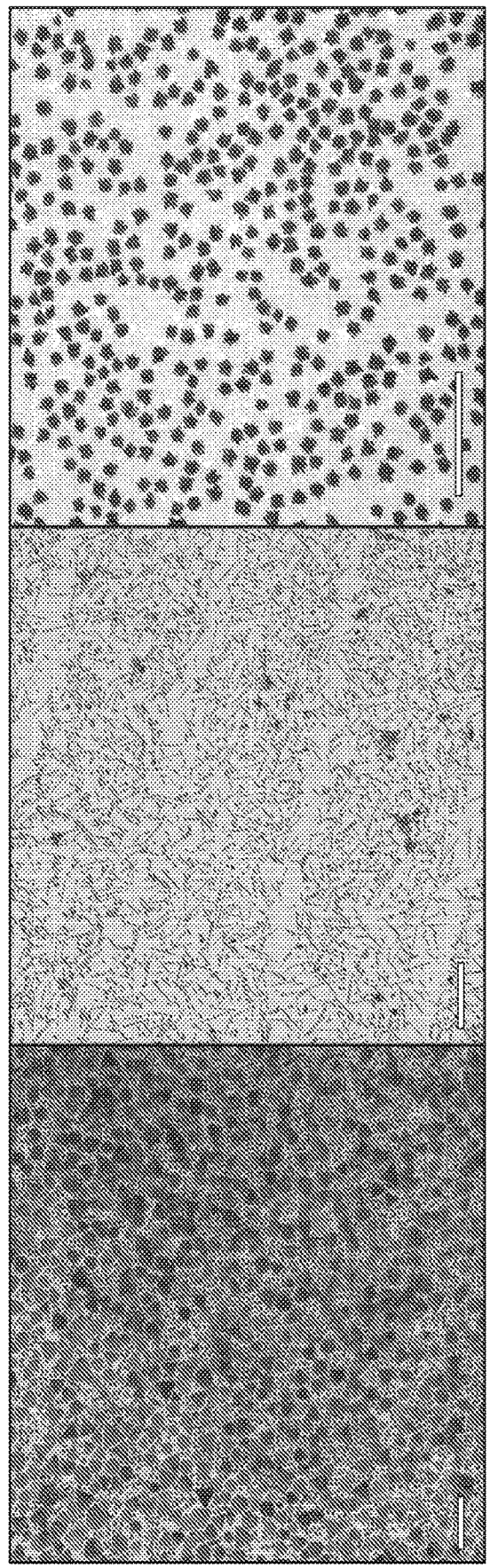
FIG. 13 illustrates typical yields before purification for various morphologies of anisotropic metal nanoparticles as described herein. The scale bar is 500 nm for plates and rods. The scale bar is 200 nm for stars. Increasing the concentration of multiply-twinned or singly twinned seeds in the initial population increases the yield of nanorods or nanoplates, respectively.
Figure 14:
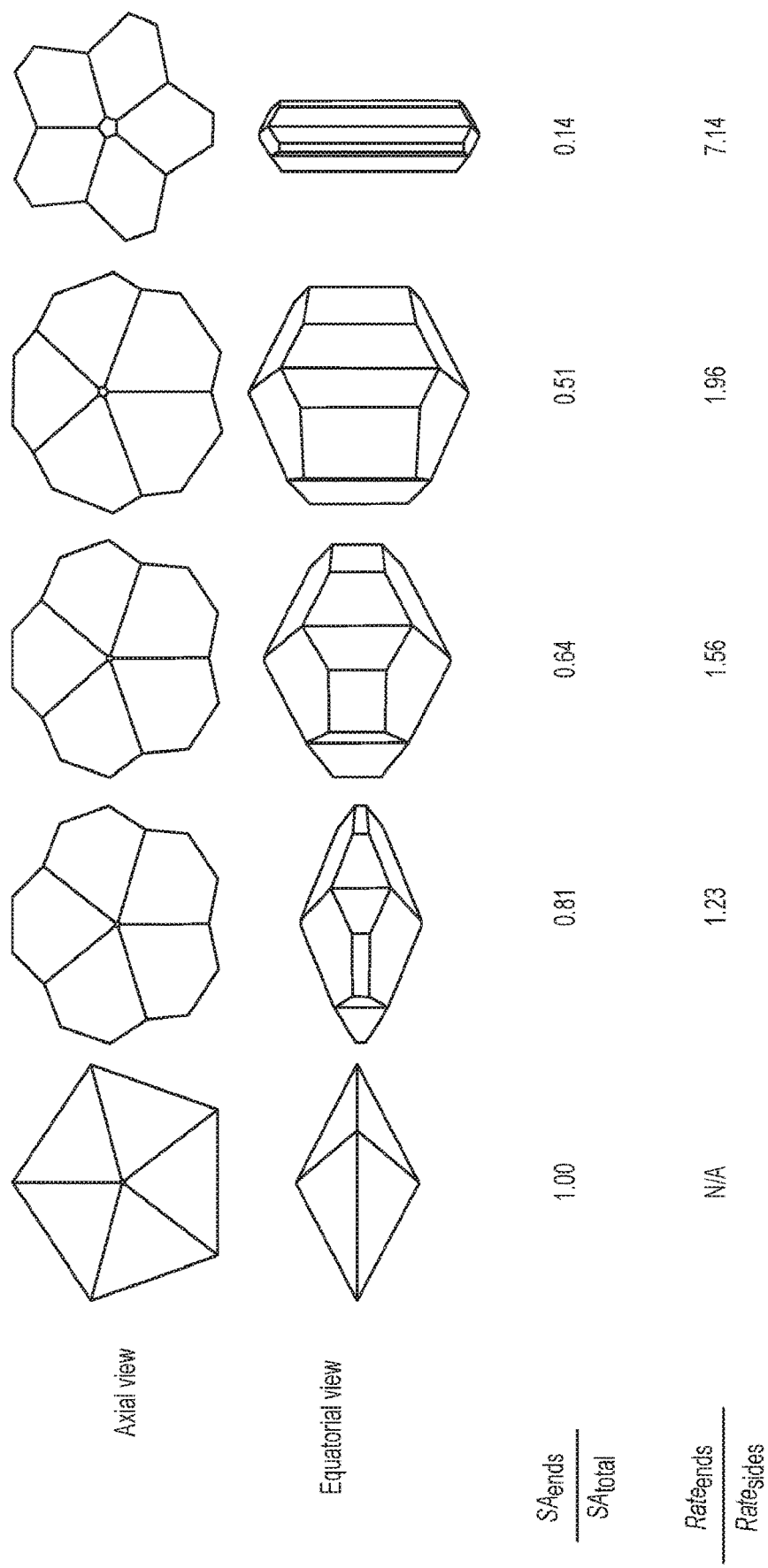
FIG. 14 illustrates distribution of surface area as a function of etching. As etching proceeds, the proportion of surface area at the pentagonally-twinned ends to surface area of the side facets (SAends:SAsides) decreases. According to the surface area limited approach, a decrease in the surface area of a given facet corresponds to an increase in the growth rate normal to that facet because the number of atoms required to form a monolayer decreases. Therefore, when oxidative etching of the pentagonally-twinned particle proceeds as depicted, the particle becomes increasingly activated toward asymmetric growth parallel to the five-fold axis.

FIG. 5 depicts catalysis of resazurin and hydroxylamine in the presence of gold nanostars. The fluorescence intensity at an excitation wavelength of 571 nm and emission wavelength of 584 nm was followed every five minutes after reaction initiation. The conversion completed after approximately 15 minutes. The fluorescence intensity of the control reaction of resazurin and hydroxylamine in the absence of gold nanostars did not exceed 2,500 au over the course of several hours. Error bars represent results of triplicate data. FIG. 6 presents a calibration curve for fluorescence intensity of resazurin versus concentration. At the highest concentration (equal to the starting concentration of resazurin in the catalytic reactions) the intensity was only 1,053 au.

Example 6: Comparison of Shape-Controlled Syntheses

As described herein, FIG. 22 shows a schematic comparing shape-controlled syntheses. As described herein, conventional synthetic methods for shape-controlled nanoparticle formation typically use surface-blocking groups to drive growth in the direction of the least encumbered facets. This technique leaves the surface largely blocked by species such as surfactants or polymers that diminish the effectiveness of the nanoparticles for various applications.

In contrast, methods described herein use reactions free of surfactants and polymers to generate nanoparticles with unblocked surfaces that are optimal for surface-dependent applications like catalysis and SERS.

Example 7: Confirming Benign Environmental Impact of Exemplary Nanoparticles

The present Example demonstrates that gold nanoparticles as described herein have various desirable properties including, for example, low cytotoxicity and/or superior performance (e.g., catalytic activity and surface enhancement to Raman scattering) compared to similar nanoparticles fabricated from surfactant (e.g., cetyltrimethylammonium bromide, CTAB) or polymer (e.g., thiolated polyethylene glycol) coatings.

For example, as presented herein, absence of surfactants and polymers allows nanoparticle surfaces to be more accessible to molecules in solution, thereby potentially enhancing performance in surface-area-dependent applications. For instance, catalytic efficiency and surface enhancement to Raman scattering of nanoparticles synthesized by the methods described herein demonstrated markedly superior performance when compared to similar nanoparticles made with surfactant (cetyltrimethylammonium bromide, CTAB) or polymer (thiolated polyethylene glycol) coatings (FIGS. 23A-23C). The surfactant-free nanoparticles also obviate post-synthetic detoxification (e.g., removal of CTAB) for biomedical applications since they are non-toxic.

In some embodiments, theoretical and/or experimental findings presented herein are broadly applicable in the design of improved nanoparticle syntheses and understanding of (nano)crystal growth mechanisms.

Moreover, preferential growth of nanoplates at slow reduction kinetics fits well with the theoretical framework presented herein. SAED of nanoplates reveals the forbidden $1/3\{22\bar{4}\}$ reflection (FIGS. 33A and 33B) characteristic of parallel twin boundaries known to create re-entrant grooves on the nanoplate side facets, which are typically $\{100\}$. Inspection of FIG. 24F reveals that $\{100\}$ facets grow under nucleation-limited growth at very slow nucleation rates, but then transition to diffusion-limited growth at higher nucleation rates (experimental rates are below the red contour line). The re-entrant grooves are known to have a strong catalytic effect for monolayer nucleation, but offer less preference when growth is limited by diffusion of growth units. Without wishing to be bound to any theory, this could explain why plates become considerably less anisotropic as reduction kinetics increase. The lack of nanorod formation at the lowest reduction kinetics appears to result from multiply twinned seeds attaining structural defects other than re-entrant grooves on {111} facets, such that the symmetry-breaking event that initiates nanorod growth does not occur.

Example 8: Confirming Results of Presented Theoretical Framework

The present Example demonstrates that a theoretical framework can be used to relate the observed crystal growth rate to the rate-limiting process controlling growth.

In this Example, for instance, crystal growth was monitored by three distinct steps: nucleation of a monolayer, diffusion of growth units to a step front, and incorporation of growth units into binding sites at the step front (FIGS. 24A-24F). As described herein, the classical theory of crystal growth can be expanded by removing outdated mathematical simplifications, and by unifying the previously disparate theoretical approaches of nucleation-, diffusion-, and incorporation reaction-limited modelling. In some embodiments, as presented herein, a theoretical approach includes a thermodynamic modeling approach. In some embodiments, as presented herein, a theoretical approach includes a kinetics modeling approach. Those skilled in the art understand that crystal growth can be modeled by thermodynamic and/or kinetics modelling approaches.

The theoretical framework presented herein uses literature values of diffusion activation energies and atomic vibrational frequencies at different lattice sites to identify ranges of nucleation rates and diffusional flux that correspond to nucleation-limited, diffusion-limited, and reaction-limited growth. An exemplary theoretical framework and all explicit calculations are provided herein.

It is noted that the provided theoretical framework applies generally to other nanoparticle systems. In some embodiments, for instance as presented in this Example, the theoretical framework is applied to AuNPs.

The presented theoretical results indicated that AuNP growth tends to be nucleation- or diffusion-limited at experimental growth rates (FIGS. 24E and 24F). The experimental range of growth rates characteristic to polyhedral particles (e.g., rods, plates, icosahedra, etc.)—or everything to the left of the red contour line in FIG. 24E—falls primarily within the nucleation-limited regime for {111} facets. Under nucleation-limited growth, facets which most strongly promote the nucleation of monolayers (e.g., facilitate clustering of atoms on the surface) grow fastest. It is well known that monolayers form fastest on surfaces that exhibit surface defects, such as re-entrant grooves that corral growth units into stable surface clusters. Without wishing to be bound to any theory, we propose that shape-controlled growth of AuNPs can be achieved by rationally distributing surface defects in the directions where fastest growth is desired.

As described herein, a reduction system for the presented framework is subject to many considerations. For example, formation of surface defects on metal nanoparticles is a sensitive function of redox potential. Moreover, the reduction rate of metal complexes can dictate the crystalline structure of the resulting nanoparticles. For at least these reasons, without wishing to be bound to any theory, the reducing agent employed in surfactant-free syntheses would have to exhibit a finely tunable reduction potential ranging from oxidative to highly reductive values in order to enable shape-control. Additionally, without wishing to be bound to any theory, the reducing agent should be small and not form particularly strong bonds with the nanoparticle, such that it does not passivate the surface. As described herein, it was found that hydrogen peroxide satisfied all of the desirable criteria, as its reduction potential can be easily tuned by pH and its molecular interactions with gold surfaces are not sufficiently strong to result in passivation.

Example 9: Confirming Shape-Controlled Synthesis of Gold Nanoparticles without Surfactants The present Example demonstrates that technologies provided herein permit synthesis of gold nanoparticles of various morphologies. For example, after testing various combinations of $HAuCl_4$, $H_2O_2$, NaOH, and 4 nm gold nanoparticle seeds, protocols, such as those described herein, were shown to generate four AuNP morphologies: nanostars, nanospheres, nanorods, and nanoplates (FIGS. 25A-25C, FIG. 27). For instance, nanostars and nanospheres formed under the fastest reduction kinetics (i.e., ≥1.35×10$^{-4}$ M s$^{-1}$) (FIGS. 28 and 29). Both morphologies demonstrate an intermediate state exhibiting protrusions from a central core. When the conditions are sufficiently reductive the protrusions are metastable and can be preserved indefinitely by dialysis to achieve nanostars (FIGS. 30A-30F, FIGS. 31A-31D). Slightly more oxidative conditions cause the protrusions to ripen, yielding nanospheres. As described herein, the symmetric development of protrusions mitigates any inherent anisotropy in the initial seed defect structure. When the reduction rate falls just below 7.26×10$^{-6}$ M s$^{-1}$, nanorods become the dominant anisotropic shape. Decreasing the reduction rate further to 9.34×10$^{-8}$ M s$^{-1}$ yields nanoplates as the primary product, and additional decreases in reduction kinetics generate heavily defected nanoparticles.

Formation of gold nanorods from this simple reaction is surprising, as they are the prototypical shape thought to require surfactants for synthesis. Although their yield (approximately 20%) was low with respect to the best surfactant-mediated synthesis, it is considerably higher than any other surfactant-free method previously reported. It is noted that the early surfactant-mediated approach (e.g., without Ag$^+$) generated 4% yields of gold nanorods. As described herein, synthesis technologies as provided herein can be combined with purification techniques such as centrifugal split-flow thin cell (C-SPLITT) separation to obtain high-yield dispersions of nanorods.

Example 10: Confirming Growth Mechanism of Gold Nanorods

The present Example demonstrates a growth mechanism analysis for gold nanorods as described herein.

For example, the present disclosure documents a nanorod formation mechanism both theoretically and experimentally. Selected area electron diffraction (SAED) analyses revealed an internal five-fold twin structure consistent with previously reported gold nanorods exhibiting slow-growing {100} side facets and fast-growing {111} end facets (FIG. 21). As an experimental growth rate of approximately 10 nm s$^{-1}$ from the {111} facets could possibly fall in either the nucleation- or diffusion-limited regimes, in some embodiments, Monte Carlo statistical simulations of nucleation- and diffusion-limited growth are calculated. Diffusion-limited growth was determined to be unstable with respect to realistic fluctuations in experimental conditions: a temporary decrease in the flux of atoms to the nanoparticle would result in dissolution, and a temporary increase would cause nanostar formation (FIG. 26A). Nucleation-limited growth was found to be stable with respect to realistic fluctuations in experimental conditions (FIG. 26B), making it a viable rate-limiting step according to the presented theoretical framework.

The present Example provides experimental corroboration of a nucleation-limited growth mechanism by high-resolution transmission electron microscopy (HRTEM). Re-entrant grooves were discovered on the {111} end facets, but not on the {100} side facets (FIG. 26C). The re-entrant grooves can increase monolayer nucleation rates, which explain why the end facets grow faster than the sides. Eucentric sample tilting was often required to resolve the structures, but they were clearly and consistently observed. The need for high resolution imaging at the proper orientation may explain the lack of previous reports for these structures on metal nanorods.

The observed nanorod dimensions were fit to a simple nucleation-limited growth model. It was found that the best fit to data occurs for a seed beginning anisotropic growth at a diameter of 7.5 nm and exhibiting a 76:1 ratio of {111} to {100} nucleation rates (FIG. 24D). It was found that there was no particularly good fit to data for the 4 nm starting seed diameter, indicating that an active symmetry-breaking step—presumably the formation of re-entrant grooves—may occur for nanorods to grow in the presented methods.

Example 11: Exemplary Protocols

Materials

Hydrogen peroxide (TraceSELECT; Sigma Aldrich) and all other chemicals were ordered from Sigma-Aldrich with the highest purity available and used as received. In all cases 18.2 MΩ·cm water was used. Slide-A-Lyzer 2K Dialysis Cassettes G2 were ordered from Thermo Scientific and used in all dialysis experiments.

Gold Nanoparticle Characterization

HRTEM analyses, bright and dark field images from FIGS. 26A-26D, FIGS. 32A-32F, and 32A-32B, and electron diffraction were performed on 200 kV JEOL 2100F High-Resolution Transmission Electron Microscopes from Brookhaven National Laboratory and Hunter College. TEM bright field images from FIGS. 25A and 25B, 27, 30A-30F, and 31A-31D were acquired using a JEOL 1200 EX-II TEM at Memorial Sloan Kettering Cancer Center. EDS was obtained with EDAX hardware and software from the JEOL 2100F HRTEM at Hunter College. Nanoparticle concentrations were determined by nanoparticle tracking analysis (Nanosight; Salisbury, United Kingdom). Nanoparticle separations were performed by Postnova Analytics Inc. (Salt Lake City, Utah, USA) using centrifugal split-flow thin fractionation (C-SPLITT).

Gold Nanoparticle Synthesis 3.5 nm Gold Seeds—

3.5 nm seeds were synthesized by a modification of the standard $NaBH_4$ method. Briefly, 100 µL of 25.4 mM $HAuCl_4$ was added to 10 mL of $H_2O$, then 300 µL of 100 mM ice-cold NaBH4 was added to this solution under vigorous stirring. The formation of seeds could be monitored by the immediate appearance of an orange-brown color. These seeds were used in all reactions without further treatment. It was observed that the seeds were susceptible to aggregation over time due to the lack of strong capping agents. The conventional seed preparation that adds sodium citrate into the borohydride reduction can be supplemented for increased seed stability and all of the same product morphologies can still be obtained.

It was observed that dialysis of the seeds in a 2,000 Da molecular weight cut-off cassette to remove unreacted ions did not prevent the formation of any morphologies, nor did the addition of citrate to the seed synthesis. Therefore, the influence of the capping agents present on the seeds was treated as negligible in the described syntheses.

Nanoplates—

150 µL of as-prepared 3 nm seeds were added to 9.85 mL of $H_2O$. 150 µL of 25.4 mM HAuCl4 was added to the mixture and the reaction was initiated by the addition of 200 µL of 0.3% (v/v) $H_2O_2$ under stirring.

Nanorods—

600 µL of as-prepared 3 nm seeds were added to 9.40 mL of $H_2O$. 30 µL of 30% $H_2O_2$ was added to this mixture and the reaction was initiated by the addition of 300 µL of 25.4 mM $HAuCl_4$ under vigorous stirring. Results were obtained by adding the $HAuCl_4$ in increments of 30 µL every 2-3 seconds.

Nanospheres—

30 µL of as-prepared 3 nm seeds were added to 9.97 mL of ice-cold $H_2O$. 150 µL of 25.4 mM $HAuCl_4$ was added to this mixture and the reaction was initiated by adding a solution of 15 µL 1 M NaOH dissolved in 1 mL of 0.3% $H_2O_2$. The balance between NaOH and seed concentration is very sensitive during sphere formation. In some embodiments, for example, when the synthesis begins with the appearance of a blue color, less NaOH should be used. In some embodiments, for example, when rods or other anisotropic polyhedra are observed in the products, more NaOH should be used. Addition of chloride or bromide before reduction of $HAuCl_4$ improves the symmetry of the spheres.

Nanostars—

30 µL of as-prepared 3 nm seeds were added to 9.97 mL of ice-cold $H_2O$. 150 µL of 25.4 mM $HAuCl_4$ was added to this mixture and the reaction was initiated by adding a solution of 50 µL 1 M NaOH dissolved in 1 mL of 0.3% $H_2O_2$. Some syntheses generate stars that transform more rapidly than others, but this can be controlled to an extent by consideration of the oxidation potential generated during $HAuCl_4$ reduction. In general, the amount of NaOH added should be the minimal amount necessary to generate stars, and increasing the pH beyond this point results in increasingly rapid transformation.

Procedure for Removing Residual Chemical Species

Washing—

Immediately after the nanostars are synthesized they are diluted to 150% of their original volume by the addition of ice-cold $H_2O$. The solution is then split into two separate centrifuge tubes and spun down for the minimal amount of time necessary to collect the nanostars at the bottom of the tube at 8000 rpm (e.g. approximately 4 minutes). The supernatant is removed and a small volume of ice-cold $H_2O$ is added in order to enable effective redispersion of the nanostars via ultrasonication. Finally, the original reaction volume is obtained by dilution with ice-cold $H_2O$.

In some embodiments, repeating this process multiple times can result in aggregation; however it is difficult to remove all residual reagent traces in one wash, thus shape-transformation is not prevented indefinitely by the methods described herein.

Dialysis—

Immediately after the nanostars are synthesized they are added to a 2,000 Da MWCO Slide-A-Lyzer dialysis cassette that is then placed into a large volume of $H_2O$ and subjected to slow stirring. The dialysis water is replaced periodically until residual chemical species are removed. The present Examples did not reveal the presence of any impurities on the nanoparticle surface to suggest that cassette-derived particle stabilizing effects (e.g. membrane polymer leaching) occurred.

Catalysis

The catalytic reduction of resazurin to resorufin mediated by hydroxylamine in the presence versus absence of gold nanoparticles serves as an assay for their efficacy as catalysts. 1 µL of 5 mM resazurin was added to 100 µL of 33 pM gold nanoparticle mixtures (25% rods, 25% plates, and 50% spheres) and 150 mM hydroxylamine in 10 mM pH=7.3 MES buffer. At the desired time point, the sample was centrifuged at 10,000 rpm for three minutes and 80 µL of the supernatant was removed, then added to 200 µL of pH=7.3 MES buffer in a clear-bottom 96 well plate. The fluorescence intensity at an excitation wavelength of 571 nm and emission wavelength of 584 nm was followed every ten minutes after reaction initiation. The fluorescence intensity of the control reaction of resazurin and hydroxylamine in the absence of gold nanostars remains virtually constant indicating that resazurin is not being converted into resorufin (data not shown). All experiments were performed in triplicate and measured under identical conditions.

Surface-Enhanced Raman Scattering

Surfactant-free (i.e., from the present synthetic methods), CTAB-coated, and PEG-SH-coated mixtures of 25% rods, 25% plates, and 50% spheres were compared for surface-enhanced Raman scattering (SERS) measurements of the common dye IR-792. 2.0 µL of $2\times10^{-5}$ M IR-792 was added to 100 µL of 0.50 nM aqueous nanoparticle samples and allowed to stir for 15 minutes at room temperature. SERS spectra were then recorded by a Raman spectrometer (Renishaw, Gloucestershire, UK) with 785 nm laser excitation at 3 mW/cm$^2$ for 1 s. No aggregation was present in any of the samples, insuring that the SERS intensity was not complicated by the presence of aggregation-induced hotspots.

Monte Carlo Calculations:

Distributions of nanorod growth rates from nucleation-limited and diffusion-limited hypotheses were generated in Matlab. Nucleation rate and flux (i.e. diffusion rate) were modeled as normally distributed random variables. The mean nucleation rate and flux were chosen to be the values that that give the experimental growth rate (i.e. 10 nm/s from {111} facets) under nucleation-limited and diffusion limited hypotheses, respectively. The standard deviation was set to be 1% of the mean. The input distributions were randomly sampled 106 times in order to generate the output facet growth rate distributions shown in FIGS. 26A and 26B. An exemplary framework of such calculations are provided in Example 12.

Example 12: Exemplary Derivation of General Theory of Metal Nanocrystal Growth

In some embodiments, crystal growth is kinetic. In some embodiments, crystal growth is thermodynamic. One skilled in the art, reading the present disclosure, will understand that crystal growth can be modeled by thermodynamic and/or kinetic equations.

Overview of Theoretical Framework

This Example presents an exemplary theoretical framework describing crystal growth originating from seed crystals exhibiting well-defined facets. Growth is assumed to begin with nucleation of a two-dimensional (2D) island and proceed by step flow (i.e. lateral growth) of the nucleus into a partial monolayer. The step flow is fueled by the incorporation of monomer growth units that adsorb onto the step and diffuse to binding sites. The completion of a net monolayer occurs when the 2D nucleus spreads a distance $\lambda=h_f-h_i$. If the surface is terraced, then multiple partial monolayers spread simultaneously and $\lambda$ will be less than the length of the facet. The distance $\lambda$ will also decrease as the number of 2D nuclei on a terrace increases. The goal of this theoretical framework is to develop an expression for facet growth rates (i.e. asymptotic growth rates) as a function of the expected time for 2D monolayer nucleation, the flux of growth units to the step front, and the jumping rates of adsorbed growth units. This rate expression can be used to determine the regimes of nucleation-limited, diffusion-limited, and reaction-limited growth.

Mathematical Approach

The expected time for net monolayer completion—the time required for a facet to increase its average height by one monolayer—was determined by summing the expected time for nucleation and the expected time for partial monolayer spread of a distance 2. The expected time for nucleation is treated as a known input, thus the primary calculation in this framework is the expected time for a step to become completely filled (henceforth called step completion).

The expected time for step completion is a function of the number of growth units in the step, the flux of growth units to the step front, and the activation energies for jumping into and along the step. In the following sections, the theoretical framework was outlined by developing expressions for the expected times of growth unit arrival, one-dimensional (1D) step nucleation, and growth unit incorporation into binding sites. The latter process is divided into three separate mechanisms. The mechanism with the lowest expected time for step completion is defined to be the operating mechanism for the corresponding input parameters.

Expected Time of Growth Unit Arrival

Let the arrival of growth units at each site be modeled as a renewal process. Once growth units arrive at the step front, they diffuse into the step by a single jump. If the growth units are adsorbed on the surface, the rate at which they jump into the step is characterized by the vibrational frequency of the growth unit and activation energy of the jump. Growth units diffusing directly from solution into the step will have a different prefactor and activation energy than those corresponding to jumping into the step from a surface site. If the expected time for growth unit arrivals via diffusion, $E(T_{diff})$, is small compared to the expected time for jumps into the step, then the frequency of arrivals at each site can be well approximated by the asymptotic rate of the renewal process, $R_{diff}$:

$$R_{diff} = \frac{1}{E(T_{diff})} \quad \text{Eq. 28}$$

Assuming that the expected time for growth unit arrival is constant along the step front, the arrival rate of growth units summed over x sites is $xR_{diff}$, and the expected arrival time is:

$$E(T_{diff})_x = \frac{1}{xR_{diff}} \quad \text{Eq. 29}$$

When the arrival time is slow on the scale of incorporation into the step, it can be modeled as a rare event, which is well approximated by an exponential distribution. Such distributions have the characteristic relationship:

$$R_{diff} = \frac{1}{E(T_{diff})} \qquad \text{Eq. 30}$$

Which yields the same result for the expected arrival time over x sites:

$$E(T_{diff})_x = \frac{1}{xR_{diff}} \qquad \text{Eq. 31}$$

Let F denote the flux of growth units per nm per second to the step front, and let the length of a step unit, $a_\parallel$, be defined by the length, L, of the step and number, N, of growth units in the step:

$$F \equiv \text{flux in}\left(\frac{\text{units}}{\text{nm}\cdot\text{s}}\right) \qquad \text{Eq. 32}$$

$$a_\parallel = \frac{L}{N} \qquad \text{Eq. 33}$$

The flux of growth units per step site per second is $$Fa_\parallel = \text{flux in}\left(\frac{\text{units}}{\text{site}\cdot\text{s}}\right) \qquad \text{Eq. 34}$$

Thus, the following relation is presented that holds for arrival times that are either small or large with respect to the expected time for jumping into the step:

$$E(T_{diff}) = \frac{1}{Fa_\parallel} \qquad \text{Eq. 35}$$

$$E(T_{diff})_x = \frac{1}{xFa_\parallel} \qquad \text{Eq. 36}$$

In this theoretical framework, it is assumed for simplicity that the expected time for growth unit arrival is well approximated by the reciprocal of the rate of growth unit arrival throughout the entire range of input flux values considered.

There is an interest in seeded (nano)crystal syntheses that proceed via reduction of a metal precursor by a weak reducing agent. Such syntheses are autocatalytic wherein the seed surface plays an essential role in catalyzing the reduction of metal atom precursors. In the present treatment, therefore, it is considered that the rate of direct growth unit diffusion from solution into binding sites as negligible, since they must first interact with the surface before converting to the atomic form that is ultimately incorporated into the crystal. Application of this theory to systems wherein the direct diffusion from solution into binding sites is not negligible require modification of the equation for $E(T_{diff})_x$ to incorporate solution-to-binding site flux.

Expected Time of 1D Nucleation

The binding of a growth unit into an empty step is herein considered to constitute the process of one-dimensional (1D) nucleation. The term nucleation in this context refers to the beginning of 1D growth (i.e. along the step), rather than the attainment of a thermodynamic critical nucleus. Because a growth unit adsorbed to a step can detach before bonding to additional growth units in the step, it is important to consider whether or not the detachment rate should be used to modify the expected time for 1D nucleation. When the incorporation rate of a second growth unit is fast (e.g., more than an order of magnitude larger) with respect to the detachment of the first growth unit, the detachment rate can be neglected to a good approximation.

Let $E(T_{diff})_x$ denote the expected time for a growth unit to arrive at any one of x sites one jump away from a step site. The expected time for 1D nucleation will be a function of both $E(T_{diff})_x$ and the expected time for a growth unit to jump into a step site. Because a single surface jump is characterized by a large number of attempts (vibrational motion) and a low probability of success during each attempt, jumps can be treated into step sites as Poisson processes. As such, they are exponentially distributed, and the expected time of the process equals the reciprocal of the jump rate.

The Arrhenius rate, $R_{Arrh}$, of a surface diffusion process is given by:

$$R_{Arrh} = v_{ij}e^{-\frac{E_{ij}}{\kappa T}} \qquad \text{Eq. 37}$$

Where $v_{ij}$ is the component of vibrational frequency of the growth unit along the ij-direction, $E_{ij}$ is the activation energy for jumping from i to j, $\kappa$ is Boltzmann's constant, and T is the absolute temperature. If the jump is defined to occur in a particular direction, then an additional factor, $p_{ij}$, must be included to account for the probability of jumping in the direction of interest:

$$R_{ij} = p_{ij}v_{ij}e^{-\frac{E_{ij}}{\kappa T}} \qquad \text{Eq. 38}$$

For surface jumps, $p_{ij}$ is well approximated as the reciprocal of the number of lattice sites that an adatom can reach in a single jump (e.g. $p_{ij}$=1/3 for {111} and 1/4 for {100}, etc.}. The expected time for a single jump is therefore:

$$E(T_1)_{ij} = \frac{1}{R_{ij}} \qquad \text{Eq. 39}$$

$$E(T_1)_{ij} = \left(p_{ij}v_{ij}e^{-\frac{E_{ij}}{\kappa T}}\right)^{-1} \qquad \text{Eq. 40}$$

Let the subscripts L, U, K, and S denote the lower terrace, upper terrace, kink, and non-kink step sites, respectively. The expected time, $E(T_1)$, for jumps from the lower and upper terraces to the kink and non-kink step sites are given by:

$$E(T_1)_{LK} = \frac{1}{R_{LK}} \qquad \text{Eq. 41}$$

$$E(T_1)_{UK} = \frac{1}{R_{UK}} \qquad \text{Eq. 42}$$

$$E(T_1)_{LS} = \frac{1}{R_{LS}} \qquad \text{Eq. 43}$$

$$E(T_1)_{US} = \frac{1}{R_{US}} \qquad \text{Eq. 44}$$

Let $P_j$ denote the probability that a growth unit arriving at the step front lands in site j, and let $E(T_{step}|j)$ denote the expected time for a growth unit to jump from site j into the adjacent step site, provided the growth unit arrives at site j. The expected time for 1D nucleation is given by:

$$E(T_{1D}) = E(T_{diff})_x + \sum_{j=1}^{x} P_j E(T_{step}|j) \qquad \text{Eq. 45}$$

When the probability of arriving at each site j is equal and growth units arrive from both the upper and lower terraces, this becomes:

$$E(T_{1D}) = E(T_{diff})_x + \frac{1}{2}\left(\frac{1}{R_{LS}} + \frac{1}{R_{US}}\right) \qquad \text{Eq. 46}$$

Expected Time of Incorporation—Step Adsorption and Diffusion

Let m denote the total number of step sites at the edge of a partial monolayer, as illustrated in FIGS. 34A and 34B:

m=number of step sites

The number of sites one jump from the step is a function of the facet index and step structure. Herein, it is assumed without loss of generality that there are 2m sites one jump away from step sites, corresponding to m sites on both the lower and upper terraces:

2m=number of sites one jump away

Upon 1D nucleation, the step is fragmented into segments of length less than m on either side of the incorporated growth unit (i.e. the 1D nucleus). Because step completion proceeds independently on either side of the 1D nucleus, the expected time for completion of the largest fragment. It is denoted the number of sites in the largest fragment by n (FIG. 34B). Given a step comprising m available sites for 1D nucleation, if a growth unit adsorbs at site j $\in$(1, 2, . . . , m), n is defined as:

n=maximum(m−j, j−1)

The step fragment comprises one kink binding site—the site adjacent to the 1D nucleus—and n−1 non-kink step sites. When the expected time for step diffusion to the kink binding site is less than the expected time for an additional growth unit to jump into the step, the step diffusion process can be modeled by a continuous time Markov chain (CTMC). In particular, an n−1×n−1 infinitesimal generator matrix, typically called a Q-matrix, can be constructed. The Q-matrix, taken here to be positive dominant, has the form:

$$Q = \begin{vmatrix} R_1 & -R_{1,2} & 0 & 0 & 0 & 0 & 0 & 0 \\ -R_{2,1} & R_2 & -R_{2,3} & 0 & 0 & 0 & 0 & 0 \\ 0 & -R_{3,2} & R_3 & -R_{3,4} & 0 & 0 & 0 & 0 \\ 0 & 0 & -R_{4,3} & R_4 & -R_{4,5} & 0 & 0 & 0 \\ 0 & 0 & 0 & -R_{5,4} & R_5 & -R_{5,6} & 0 & 0 \\ 0 & 0 & 0 & 0 & -R_{6,5} & R_6 & -R_{6,7} & 0 \\ 0 & 0 & 0 & 0 & 0 & -R_{7,6} & R_7 & -R_{7,8} \\ 0 & 0 & 0 & 0 & 0 & 0 & -R_{8,7} & R_8 \end{vmatrix} \qquad \text{Eq. 47}$$

Where $R_{ij}$ is the rate of jumping from i to j, and $R_i$ is the total rate of jumping out of site i. Here n−1=8 was arbitrarily chosen for illustrative purposes.

The expected time, $E(T_{bind})$, for a growth unit in a step to reach the binding site from each initial step site is obtained by inverting the Q-matrix, and summing the entries in each row:

$$\text{ones}(n-1, 1) = \begin{pmatrix} 1 \\ \vdots \\ 1 \end{pmatrix} \qquad \text{Eq. 48}$$

$$M = Q^{-1}\text{ones}(n-1, 1) \qquad \text{Eq. 49}$$

Entry $M_{(j)}$ gives the expected time of step diffusion to the binding site for a growth unit beginning in the step site j jumps from the kink binding site. The complete list of expected times to arrive at the binding site from any step site are given by the column vector $E(T_{bind})$, where the first entry corresponds to a growth unit that is already in the binding site, the second entry corresponds to the position one jump away, and so on:

$$E(T_{bind}) = \begin{bmatrix} 0 \\ M(1) \\ \vdots \\ M(n-1) \end{bmatrix} \qquad \text{Eq. 50}$$

The column vector of expected times for jumping from the terrace into each step site is given by:

$$E(T_{step}) = \left(\frac{1}{2n}\right) \begin{bmatrix} \frac{1}{R_{L_0 S_0}} + \frac{1}{R_{U_0 S_0}} \\ \frac{1}{R_{L_1 S_1}} + \frac{1}{R_{U_1 S_1}} \\ \vdots \\ \frac{1}{R_{L_{n-1} S_{n-1}}} + \frac{1}{R_{U_{n-1} S_{n-1}}} \end{bmatrix} \qquad \text{Eq. 51}$$

Where the coefficient 1/2n is the probability that an atom impinging upon the step front arrives at the specific site $L_j$ or $U_j$ (e.g. if there are 2n=18 sites one jump away from the step, each has probability=1/18 that an impinging adatom arrives at that specific site). Here it is assumed that each site has equal likelihood of adatom arrival. For convenience, a column vector is constructed with n entries, rather than 2n, where each entry equals the sum of the contribution from the corresponding upper terrace and lower terrace sites. If the probability of growth unit arrival is different for lower terrace versus upper terrace sites then each site must be given its own entry and corresponding probability of arrival in the $E(T_{step})$ column vector.

The expected time of the growth unit incorporation reaction, $E(T_{rxn})$, was determined by summing all entries in the two column vectors, $E(T_{step})$ and $E(T_{bind})$.

$$E(T_{step} + T_{bind}) = \left(\frac{1}{2n}\right) \begin{bmatrix} \frac{1}{R_{L_0 S_0}} + \frac{1}{R_{U_0 S_0}} \\ \frac{1}{R_{L_1 S_1}} + \frac{1}{R_{U_1 S_1}} \\ \vdots \\ \frac{1}{R_{L_{n-1} S_{n-1}}} + \frac{1}{R_{U_{n-1} S_{n-1}}} \end{bmatrix} + \begin{bmatrix} 0 \\ M(1) \\ \vdots \\ M(n-1) \end{bmatrix} \quad \text{Eq. 52}$$

$$\text{ones}(1, n) = [1, 1, \dots, 1] \quad \text{Eq. 53}$$

$$E(T_{rxn}) = \text{ones}(1, n) E(T_{step} + T_{bind}) \quad \text{Eq. 54}$$

$$E(T_{rxn}) = [1, 1, \dots, 1] \begin{bmatrix} \left(\frac{1}{n}\right)\left\{0 + \frac{1}{2R_{L_0 S_0}} + \frac{1}{2R_{U_0 S_0}}\right\} \\ \left(\frac{1}{n}\right)\left\{M(1) + \frac{1}{2R_{L_1 S_1}} + \frac{1}{2R_{U_1 S_1}}\right\} \\ \vdots \\ \left(\frac{1}{n}\right)\left\{M(n-1) + \frac{1}{2R_{L_{n-1} S_{n-1}}} + \frac{1}{2R_{U_{n-1} S_{n-1}}}\right\} \end{bmatrix} \quad \text{Eq. 55}$$

Given a flux of F atoms per nm per second to the step front, the expected time for adatom arrival is:

$$E(T_{diff})_{2n} = \frac{1}{2n a_{\parallel} F} \quad \text{Eq. 56}$$

The expected time for growth unit incorporation, $E(T_{inc})$, which corrects for the detachment of atoms during growth, is given by:

$$E(T_{inc}) = \left\{\frac{(R_{KL})^{-1}[E(T_{diff})_{2n} + E(T_{rxn})]}{(R_{KL})^{-1} - [E(T_{diff})_{2n} + E(T_{rxn})]}\right\} \quad \text{Eq. 57}$$

The derivation of the correction factor is provided at the end of the theoretical framework. The expected time for step fragment completion, $E(T_{fragment})$, is obtained repeating the calculation of $E(T_{inc})$ after each new atom is added into the step until all sites have been filled:

$$E(T_{fragment}) = \sum_{k=1}^{n} E(T_{diff})_{2k} + \text{ones}(1, k)\left[\frac{1}{k} E(T_{step} + T_{bind})_k\right] \quad \text{Eq. 58}$$

Because the 1D nucleation event can occur at any one of the m available sites, the initial growth unit adsorption must be randomized in order to arrive at the expected time for step completion. The resulting equation gives the expected time for completion of an entire row (i.e. entire step), $E(T_{row})$, according to the mechanism depicted in FIG. 34C:

$$E(T_{row})_{mech.1} = \left(E(T_{diff})_{2m} + \frac{1}{2R_{LS}} + \frac{1}{2R_{US}}\right) + \frac{1}{m}\sum_{j=1}^{m}\left\{\sum_{k=1}^{n} E(T_{diff})_{2k} + \text{ones}(1, k)\left[\frac{1}{k} E(T_{step} + T_{bind})_k\right]\right\} \quad \text{Eq. 59}$$

$$E(T_{step} + T_{bind})_{k=1} = \frac{1}{2}\left(\frac{1}{R_{LK}} + \frac{1}{R_{UK}}\right) \quad \text{Eq. 60}$$

-continued $$E(T_{step} + T_{bind})_{k=2} = \begin{bmatrix} \frac{1}{4}\left(\frac{1}{R_{LK}} + \frac{1}{R_{UK}}\right) \\ \frac{1}{4}\left(\frac{1}{R_{LS}} + \frac{1}{R_{US}} + \frac{2}{R_{SK}}\right) \end{bmatrix} \quad \text{Eq. 61}$$

$$E(T_{step} + T_{bind})_{k \geq 3} = \left(\frac{1}{k}\right) \begin{bmatrix} \frac{1}{2}\left(\frac{1}{R_{LK}} + \frac{1}{R_{UK}}\right) \\ M(1) + \frac{1}{2}\left(\frac{1}{R_{LS}} + \frac{1}{R_{US}}\right) \\ \vdots \\ M(k-1) + \frac{1}{2}\left(\frac{1}{R_{LS}} + \frac{1}{R_{US}}\right) \end{bmatrix} \quad \text{Eq. 62}$$

Recall that n=maximum(m−j, j−1).

Expected Time of Incorporation—Direct Step Binding

When the arrival of growth units into the step becomes sufficiently fast, the mechanism of incorporation no longer includes diffusion along the step (FIG. 34D). The threshold where the incorporation mechanism changes from step adsorption and diffusion to direct step binding (i.e. incorporation without diffusion within the step) can be approximated by comparing the expected time for growth units to jump into the step and the expected time for growth units to diffuse to the kink. In particular, the mechanism changes when the expected time for a growth unit to diffuse to a kink is greater than the expected time for a second growth unit to jump into the step.

The expected time to complete a row of step atoms, $E(T_{row})$, via direct step binding is determined by summing the expected times for consecutive arrival and step adsorption events. For a step with m available binding sites prior to 1D nucleation it is presented:

$$E(T_{row})_{mech.2} = \sum_{k=0}^{m-1} E(T_{diff})_{2(m-k)} + \frac{1}{2}\left(\frac{1}{R_{LS}} + \frac{1}{R_{US}}\right)_k \quad \text{Eq. 63}$$

Where the subscript k on the last term indicates that the expected time for jumping into the step can change as the number of adsorbed growth units in the step changes. When the activation energy for incorporation into the step does not depend strongly on the number of adsorbed growth units then the following approximation can be used:

$$E(T_{row})_{mech.2} = \sum_{k=0}^{m-1} E(T_{diff})_{2(m-k)} + \left(\frac{m}{2}\right)\left(\frac{1}{R_{LS}} + \frac{1}{R_{US}}\right) \quad \text{Eq. 64}$$

Note that because the step does not complete symmetrically outward from the 1D nucleation site it is not sufficient to consider only the completion of the largest step fragment of n sites. Notice also that the detachment rate has been neglected because step completion occurs very rapidly with respect to growth unit detachment.

Expected Time of Incorporation—Direct Kink Binding

As the expected time for growth unit arrival at the step front approaches zero, incorporation into the step becomes reaction limited. When the activation energy for direct incorporation into a kink site is significantly lower than that for direct incorporation into a non-kink step site, the minimum expected time for step completion will occur via direct kink binding. That is, after 1D nucleation, growth units will exclusively incorporate into the step by jumping from the terraces into the kink binding sites. Because this mechanism creates symmetric kink propagation from the initial 1D nucleation site, the expected time for step completion equals the expected time for the largest step fragment of n sites. Thus, the expected time equals the expected time for 1D nucleation randomized over the m possible nucleation sites plus the expected time for n consecutive kink binding events:

$$E(T_{row})_{mech.3} = \left(E(T_{diff})_m + \frac{1}{2R_{LS}} + \frac{1}{2R_{US}}\right) + \quad \text{Eq. 65}$$
$$\frac{1}{m}\sum_{j=1}^{m}\left\{n\left[E(T_{diff})_2 + \frac{1}{2}\left(\frac{1}{R_{LK}} + \frac{1}{R_{UK}}\right)\right]\right\}$$

$$n = \text{maximum}(m - j, j - 1)$$

Expected Time of Step Completion

The expected time to complete a row of step atoms is a function of the incorporation mechanism and flux of growth units to the step front, as described above. Here the six step completion equations are presented: the three growth mechanism from above, each with an expression for a system wherein growth units arrive from the lower and upper terraces and a system wherein growth units arrive exclusively from the lower terrace. If the expected time for step diffusion to kink binding sites is less than the expected time for a second growth unit to jump into the step, then mechanism 1 (i.e. step adsorption and diffusion) is used. Otherwise, the expected time for step completion via mechanisms 2 and 3 are both computed and the minimum expected time is selected. This processes is repeated from the initial step—corresponding to the edge of the 2D critical nucleus— to the final step, defined as the step that completes a net monolayer.

The six expressions considered are:

Mechanism 1, Upper and Lower Terrace $$E(T_{row})_{mech.1} = \left(E(T_{diff})_{2m} + \frac{1}{2R_{LS}} + \frac{1}{2R_{US}}\right) + \quad \text{Eq. 66}$$
$$\frac{1}{m}\sum_{j=1}^{m}\left\{\sum_{k=1}^{n} E(T_{diff})_{2k} + \text{ones}(1,k)\left[\frac{1}{k}E(T_{step} + T_{bind})_k\right]\right\}$$

$$E(T_{step} + T_{bind})_{k=1} = \frac{1}{2}\left(\frac{1}{R_{LK}} + \frac{1}{R_{UK}}\right) \quad \text{Eq. 67}$$

$$E(T_{step} + T_{bind})_{k=2} = \begin{bmatrix} \frac{1}{4}\left(\frac{1}{R_{LK}} + \frac{1}{R_{UK}}\right) \\ \frac{1}{4}\left(\frac{1}{R_{LS}} + \frac{1}{R_{US}} + \frac{2}{R_{SK}}\right) \end{bmatrix} \quad \text{Eq. 68}$$

$$E(T_{step} + T_{bind})_{k \geq 3} = \left(\frac{1}{k}\right)\begin{bmatrix} \frac{1}{2}\left(\frac{1}{R_{LK}} + \frac{1}{R_{UK}}\right) \\ M(1) + \frac{1}{2}\left(\frac{1}{R_{LS}} + \frac{1}{R_{US}}\right) \\ \vdots \\ M(k-1) + \frac{1}{2}\left(\frac{1}{R_{LS}} + \frac{1}{R_{US}}\right) \end{bmatrix} \quad \text{Eq. 69}$$

Mechanism 1, Lower Terrace Only $$E(T_{row})_{mech.1L} = \left(E(T_{diff})_m + \frac{1}{R_{LS}}\right) + \quad \text{Eq. 70}$$
$$\frac{1}{m}\sum_{j=1}^{m}\left\{\sum_{k=1}^{n} E(T_{diff})_k + \text{ones}(1,k)[E(T_{step} + T_{bind})_k]\right\}$$

$$E(T_{step} + T_{bind})_{k=1} = \frac{1}{R_{LK}} \quad \text{Eq. 71}$$

$$E(T_{step} + T_{bind})_{k=2} = \begin{bmatrix} \frac{1}{2R_{LK}} \\ \frac{1}{2}\left(\frac{1}{R_{LS}} + \frac{1}{R_{SK}}\right) \end{bmatrix} \quad \text{Eq. 72}$$

$$E(T_{step} + T_{bind})_{k \geq 3} = \left(\frac{1}{k}\right)\begin{bmatrix} \frac{1}{2}\frac{1}{R_{LK}} \\ M(1) + \frac{1}{R_{LS}} \\ \vdots \\ M(k-1) + \frac{1}{R_{LS}} \end{bmatrix} \quad \text{Eq. 73}$$

Mechanism 2, Upper and Lower Terrace $$E(T_{row})_{mech.2} = \sum_{k=0}^{m-1} E(T_{diff})_{2(m-k)} + \left(\frac{m}{2}\right)\left(\frac{1}{R_{LS}} + \frac{1}{R_{US}}\right) \quad \text{Eq. 74}$$

Mechanism 2, Lower Terrace Only $$E(T_{row})_{mech.2L} = \sum_{k=0}^{m-1} E(T_{diff})_{(m-k)} + \frac{m}{R_{LS}} \quad \text{Eq. 75}$$

Mechanism 3, Upper and Lower Terrace $$E(T_{row})_{mech.3} = \left(E(T_{diff})_m + \frac{1}{2R_{LS}} + \frac{1}{2R_{US}}\right) + \frac{1}{m}\sum_{j=1}^{m}\left\{n\left[E(T_{diff})_2 + \frac{1}{2}\left(\frac{1}{R_{LK}} + \frac{1}{R_{UK}}\right)\right]\right\} \quad \text{Eq. 76}$$

$$n = \text{maximum}(m - j, j - 1)$$

Mechanism 3, Lower Terrace Only $$E(T_{row})_{mech.3L} = \left(E(T_{diff})_m + \frac{1}{R_{LS}}\right) + \frac{1}{m}\sum_{j=1}^{m}\left\{n\left[E(T_{diff})_1 + \frac{1}{R_{LK}}\right]\right\} \quad \text{Eq. 77}$$

$$n = \text{maximum}(m - j, j - 1)$$

Formula for Step Size as a Function of Partial Monolayer Radius

In order to employ the expected time for step completion to determine the expected time for layer completion, an expression for the number of step sites as a function of the partial monolayer size must be derived. If step flow via the completion of consecutive single steps is considered, then the geometry of the partial monolayer and the symmetry of its growth (e.g. a triangle growing from three edges, a triangle growing from one edge, etc.) will be the primary factors in developing an expression for the number of step sites, m(h), as a function of the length, h, of the partial monolayer. Because there is an interest in growth originating from the corners of triangular {111} facets (i.e. symmetry of growth on {111} nanorod facets), an expression for a triangular partial monolayer growing from one edge is used:

$$m(h+1) = m(h) + 1 \quad \text{Eq. 78}$$

When alternative geometries and growth symmetries are used, the appropriate expression is likely to change. The form of the recursion formula will only change by the value of the constant for many relevant cases.

Expected Time of Net Monolayer Completion

Once the expected time for step completion and the formula for the number of step sites as a function of partial monolayer size are known, the expected time of net monolayer completion is straightforward to compute. Using the example of a triangular partial monolayer spreading from one edge, it can be seen that the $m^{th}$ step requires m growth units for completion. The expected time for monolayer completion can therefore be determined by summing the expected time for step completion over the total number of steps required to complete a net monolayer:

Mechanism 1, Upper and Lower Terrace $$E(T_{monolayer})_{mech.1} = \sum_{m=h_i}^{h_f}\left[E(T_{diff})_{2m} + \frac{1}{2}\left(\frac{1}{R_{LS}} + \frac{1}{R_{US}}\right) + \frac{1}{m}\sum_{j=1}^{m}\left\{\sum_{k=1}^{n}E(T_{diff})_{2k} + \text{ones}(1, k)[E(T_{step} + T_{bind})_k]\right\}\right] \quad \text{Eq. 79}$$

$$E(T_{step} + T_{bind})_{k=1} = \frac{1}{2}\left(\frac{1}{R_{LK}} + \frac{1}{R_{UK}}\right) \quad \text{Eq. 80}$$

$$E(T_{step} + T_{bind})_{k=2} = \begin{bmatrix} \frac{1}{4}\left(\frac{1}{R_{LK}} + \frac{1}{R_{UK}}\right) \\ \frac{1}{4}\left(\frac{1}{R_{LS}} + \frac{1}{R_{US}} + \frac{2}{R_{SK}}\right) \end{bmatrix} \quad \text{Eq. 81}$$

$$E(T_{step} + T_{bind})_{k \geq 3} = \left(\frac{1}{k}\right)\begin{bmatrix} \frac{1}{2}\left(\frac{1}{R_{LK}} + \frac{1}{R_{UK}}\right) \\ M(1) + \frac{1}{2}\left(\frac{1}{R_{LS}} + \frac{1}{R_{US}}\right) \\ \vdots \\ M(k-1) + \frac{1}{2}\left(\frac{1}{R_{LS}} + \frac{1}{R_{US}}\right) \end{bmatrix} \quad \text{Eq. 82}$$

Mechanism 1, Lower Terrace Only $$E(T_{monolayer})_{mech.1L} = \sum_{m=h_i}^{h_f}\left[\left(E(T_{diff})_m + \frac{1}{R_{LS}}\right) + \frac{1}{m}\sum_{j=1}^{m}\left\{\sum_{k=1}^{n}E(T_{diff})_k + \text{ones}(1, k)[E(T_{step} + T_{bind})_k]\right\}\right] \quad \text{Eq. 83}$$

$$E(T_{step} + T_{bind})_{k=1} = \frac{1}{R_{LK}} \quad \text{Eq. 84}$$

$$E(T_{step} + T_{bind})_{k=2} = \begin{bmatrix} \frac{1}{2R_{LK}} \\ \frac{1}{2}\left(\frac{1}{R_{LS}} + \frac{1}{R_{SK}}\right) \end{bmatrix} \quad \text{Eq. 85}$$

$$E(T_{step} + T_{bind})_{k \geq 3} = \left(\frac{1}{k}\right)\begin{bmatrix} \frac{1}{R_{LK}} \\ M(1) + \frac{1}{R_{LS}} \\ \vdots \\ M(k-1) + \frac{1}{R_{LS}} \end{bmatrix} \quad \text{Eq. 86}$$

Mechanism 2, Upper and Lower Terrace $$E(T_{monolayer})_{mech.2} = \sum_{m=h_i}^{h_f}\left[\sum_{k=0}^{m-1}E(T_{diff})_{2(m-k)} + \left(\frac{m}{2}\right)\left(\frac{1}{R_{LS}} + \frac{1}{R_{US}}\right)\right] \quad \text{Eq. 87}$$

Mechanism 2, Lower Terrace Only $$E(T_{monolayer})_{mech.2L} = \sum_{m=h_i}^{h_f}\left[\sum_{k=0}^{m-1}E(T_{diff})_{(m-k)} + \frac{m}{R_{LS}}\right] \quad \text{Eq. 88}$$

Mechanism 3, Upper and Lower Terrace $$E(T_{monolayer})_{mech.3} = \sum_{m=h_i}^{h_f}\left[\left(E(T_{diff})_{2m} + \frac{1}{2R_{LS}} + \frac{1}{2R_{US}}\right) + \quad \text{Eq. 89}$$

-continued $$\frac{1}{m}\sum_{j=1}^{m}\left\{n\left[E(T_{\textit{diff}})_2 + \frac{1}{2}\left(\frac{1}{R_{LK} + \frac{1}{R_{UK}}}\right)\right]\right\}$$

$n = \text{maximum}(m - j, j - 1)$

Mechanism 3, Lower Terrace Only $$E(T_{monolayer})_{mech.3L} = \qquad \text{Eq. 90}$$

$$\sum_{m=h_i}^{h_f}\left[\left(E(T_{\textit{diff}})_m + \frac{1}{R_{LS}}\right) + \frac{1}{m}\sum_{j=1}^{m}\left\{n\left[E(T_{\textit{diff}})_1 + \frac{1}{R_{LK}}\right]\right\}\right]$$

$n = \text{maximum}(m - j, j - 1)$

Asymptotic Growth Rate Normal to Surface

Although the expected time for net monolayer completion has a clear meaning and strong mathematical foundation, it is much more common to experimentally measure and report crystal growth "rates". Although the rate of a process has an intuitive colloquial meaning, it is important to articulate exactly which rate is referenced when attempting to provide a meaningful mathematical expression. Because there is no reason to assume that the time for monolayer completion should be an exponentially distributed random variable, it cannot be assumed that the "rate" of monolayer completion is defined as the reciprocal of the expected time for monolayer completion. It is, however, reasonable to consider the asymptotic rate of monolayer formation over growth of several tens of nanometers. In this case, monolayer formation can be treated as a renewal process, and thus the expected time for layer formation as constant. This requires the assumption that the expected time for nucleation and the flux of growth units per step site per second are constant throughout the timeframe of crystal growth. Note, however, that a seed crystal growing from time $t_1$ to $t_2$ and another seed crystal growing from time $t_3$ to $t_4$ can be subject to different nucleation rates and flux. The (asymptotic) rate of crystal growth, $R_{hkl}$, normal to a facet with Miller indices hkl and monolayer height $d_{hkl}$ is defined as:

$$R_{hkl} = \frac{d_{hkl}}{E(T_{monolayer})_{hkl}} \qquad \text{Eq. 91}$$

The units of $R_{hkl}$ are nm per second, and the logarithm of this rate as a function of nucleation rate and growth unit flux is used to generate the crystal growth contour plots reported in the main text. The advantage of using this expression is that it can be compared to experimental measurements and alternative rate expressions commonly found in the literature. It should be noted, however, that working instead with the expected time for monolayer formation provides the advantages of a slightly less restricted mathematical foundation and distinct contributions from the expected times of 2D nucleation and partial monolayer spread.

Derivation of the Correction Factor for the Detachment of Growth Units

Suppose one would like to know the expected time for a step fragment of n unfilled sites to be completely filled, one site at a time. If the expected time for one atom to fill a binding site is $E(t_{att})$, then the expected time, $E(t_{n,att})$, for n binding events is:

$$E(t_{n,att}) = nE(t_{att}) \qquad \text{Eq. 92}$$

If detachment of atoms from binding sites did not occur, then $E(t_n)$ would be the expected time for the step fragment comprising n atoms to be completed. In reality, however, atoms detach from binding sites at a rate of $R_{det}$. Because the detachment is a Poisson process, the expected time for an atom to detach, $E(t_{det})$, is:

$$E(t_{det}) = \frac{1}{R_{det}} \qquad \text{Eq. 93}$$

From the expected times for incorporation and detachment of atoms at binding sites, the expected number of attachments, $N_{att}$, and detachments, $N_{det}$, from time t=0 to τ can be written:

$$N_{att}(\tau) = \frac{\tau}{E(t_{att})} \qquad \text{Eq. 94}$$

$$N_{det}(\tau) = \frac{\tau}{E(t_{det})} \qquad \text{Eq. 95}$$

The number of attachments minus the number of detachments gives the net number of atoms incorporated, $N_{inc}$. The net number of atoms incorporated in time τ, is:

$$N_{inc}(\tau) = N_{att}(\tau) - N_{det}(\tau) \qquad \text{Eq. 96}$$

$$N_{inc}(\tau) = \frac{\tau}{E(t_{att})} - \frac{\tau}{E(t_{det})} \qquad \text{Eq. 97}$$

$$N_{inc}(\tau) = \frac{\tau[E(t_{det}) - E(t_{att})]}{E(t_{att})E(t_{det})} \qquad \text{Eq. 98}$$

Setting τ=1s gives the net number of atoms incorporated per second:

$$N_{inc}\left(\frac{\text{atoms}}{s}\right) = \frac{[E(t_{det}) - E(t_{att})]}{E(t_{att})E(t_{det})} \qquad \text{Eq. 99}$$

In order to determine the expected time, in seconds, for an atom to be incorporated, $E(t_{inc})$, the reciprocal of $N_{inc}$ is taken:

$$E(t_{inc}) = \frac{1}{N_{inc}} \qquad \text{Eq. 100}$$

$$E(t_{inc}) = \frac{E(t_{att})E(t_{det})}{[E(t_{det}) - E(t_{att})]} \qquad \text{Eq. 101}$$

$$E(t_{inc}) = \left\{\frac{E(t_{det})}{[E(t_{det}) - E(t_{att})]}\right\}E(t_{att}) \qquad \text{Eq. 102}$$

The expected time, $E(t_{n,inc})$, for n sites to be filled (i.e. $N_{att}-N_{det}=n$), is therefore given by:

$$E(t_{n,inc}) = nE(t_{inc}) \qquad \text{Eq. 103}$$

$$E(t_{n,inc}) = \left\{ \frac{E(t_{det})}{[E(t_{det}) - E(t_{att})]} \right\} nE(t_{att}) \qquad \text{Eq. 104}$$

It is seen in the last expression, that the net time for n sites to be filled is equal to the expected time of attachment, multiplied by the ratio $$\left\{ \frac{E(t_{det})}{[E(t_{det}) - E(t_{att})]} \right\} = \left\{ \frac{\frac{1}{R_{det}}}{\left[\frac{1}{R_{det}} - E(t_{att})\right]} \right\} \qquad \text{Eq. 105}$$

Alternatively, it can derived that this factor from the rates of attachment, detachment, and the net rate of incorporation:

$$R_{inc} = R_{att} - R_{det} \qquad \text{Eq. 106}$$

If it is assumed that the incorporation of growth units is well modeled by a renewal process wherein the asymptotic rate of attachment gives a good approximation to the experimental rate of attachment, the theorem can be applied:

$$\lim_{t \to \infty} \frac{N_{att}}{t} = \frac{1}{E(t_{att})} \qquad \text{Eq. 107}$$

$$R_{att} = \frac{N_{att}}{t} \qquad \text{Eq. 108}$$

$$R_{att} = \frac{1}{E(t_{att})} \qquad \text{Eq. 109}$$

$$R_{inc} = \frac{1}{E(t_{att})} - R_{det} \qquad \text{Eq. 110}$$

Then the expected time for n sites to be filled is given by:

$$R_{inc} E(t_{n,inc}) = n \qquad \text{Eq. 111}$$

$$E(t_{n,inc}) = \frac{n}{R_{inc}} \qquad \text{Eq. 112}$$

$$E(t_{n,inc}) = \frac{n}{\left[\frac{1}{E(t_{att})} - R_{det}\right]} \qquad \text{Eq. 113}$$

$$E(t_{n,inc}) = \frac{n}{\left[\frac{1}{E(t_{att})} - \frac{1}{E(t_{det})}\right]} \qquad \text{Eq. 114}$$

$$E(t_{n,inc}) = \frac{n}{\left[\frac{E(t_{det}) - E(t_{att})}{E(t_{att})E(t_{det})}\right]} \qquad \text{Eq. 115}$$

$$E(t_{n,inc}) = \frac{E(t_{att})E(t_{det})n}{E(t_{det}) - E(t_{att})} \qquad \text{Eq. 116}$$

$$E(t_{n,inc}) = \left[\frac{E(t_{det})}{E(t_{det}) - E(t_{att})}\right] nE(t_{att}) \qquad \text{Eq. 117}$$

Which again defines the expected time for incorporation as the expected time of attachment, multiplied by the ratio $$\left\{ \frac{E(t_{det})}{E(t_{det}) - E(t_{att})} \right\} = \left\{ \frac{\frac{1}{R_{det}}}{\left[\frac{1}{R_{det}} - E(t_{att})\right]} \right\} \qquad \text{Eq. 118}$$

OTHER EMBODIMENTS AND EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

What is claimed is:

1. A method of preparing anisotropic metallic nanoparticle cores, the method comprising steps of:
   (1) preparing metal seeds by providing a first reaction mixture comprising:
      a metal precursor complex;
      water; and
      a first reducing agent; and
   (2) providing a second reaction mixture comprising:
      metal seeds prepared in step (1);
      at least one of a metal hydroxide or a metal salt;
      a second reducing agent; and
      an oxidizing agent;
      wherein the first and second reaction mixtures are each substantially free of surface-associated surfactants, polymers, underpotential deposition species, nitrogen-containing species, sulfur-containing species, and phosphorus-containing species; and
   (3) maintaining the second reaction mixture under conditions sufficient to achieve production of anisotropic metallic nanoparticle cores of a selected morphology.

2. The method of claim 1, wherein fusion of two or more metal seeds prepared in step (1) forms grooves on the metal seeds.

3. The method of claim 1, wherein the anisotropic metallic nanoparticle cores comprise gold.

4. The method of claim 1, wherein the selected morphology is a nanostar morphology, a nanoplate morphology, or a nanorod morphology.

5. The method of claim 1, wherein the oxidizing agent is configured to oxidize the metal seed such that growth of the anisotropic metallic nanoparticle cores is activated in a selected direction.

6. The method of claim 1, wherein the oxidizing agent and the second reducing agent are the same species.

7. The method of claim 6, wherein the oxidizing agent and the second reducing agent is hydrogen peroxide.

8. The method of claim 1, wherein the step of providing comprises providing a first reaction mixture further comprising a base, so that the selected morphology is a nanostar morphology.

9. The method of claim 8, wherein the metal salt is metal chloride, and the step of maintaining comprises maintaining at a metal chloride/metal seed ratio sufficient to yield a nanostar mean diameter with a length less than 1000 nm.

10. The method of claim 8 further comprising a step, performed after the step of maintaining, of removing halide ions, metal ions, oxidative species, and any other residual ions, atoms, and/or compounds in solution so that the anisotropic metallic nanoparticle cores are stabilized.

11. A method of preparing anisotropic metallic nanoparticle cores, the method comprising steps of:
   providing a reaction mixture comprising:
   metal seeds;
   at least one of a metal hydroxide or a metal salt;
   a reducing agent; and
   an oxidizing agent, wherein the reaction mixture is substantially free of surface-associated surfactants, polymers, underpotential deposition species, nitrogen-containing species, sulfur-containing species, and phosphorus-containing species; and
   maintaining the reaction mixture under conditions sufficient to achieve production of anisotropic metallic nanoparticle cores of a selected morphology.

12. The method of claim 11, wherein fusion of the two or more metal seeds forms grooves on the metal seeds.

13. The method of claim 11, wherein the selected morphology is a nanostar morphology, a nanoplate morphology, or a nanorods morphology.

14. The method of claim 11 further comprising a step of preparing the metal seeds, which step comprises:
   (1) providing a first reaction mixture comprising:
   a metal precursor complex;
   water; and
   a first reducing agent; and
   (2) maintaining the first reaction mixture under conditions appropriate for metal seed formation.

15. The method of claim 11, wherein the step of maintaining comprises maintaining the reaction mixture for at least 30 minutes such that the selected morphology is a nanoplate morphology.

16. The method of claim 11, wherein the metal salt is metal chloride, and the step of maintaining comprises maintaining a metal chloride/metal seed ratio sufficient to yield a nanoplate morphology and a nanoplate edge length within the range of greater than or equal to 20 nm to less than 1000 nm, where longer edge lengths correspond to larger chloride/seed ratios.

17. The method of claim 11, wherein the metal salt is metal chloride, and the step of providing comprises adding peroxide to the metal seeds, and the step of maintaining comprises maintaining a peroxide/metal chloride ratio sufficient to yield anisotropic metallic nanoparticle cores with a nanorod morphology.

18. The method of claim 17, wherein the method does not involve multiple seeding steps, and the anisotropic metallic nanoparticle cores with a nanorod morphology have an aspect ratio greater than 20.

19. The method of claim 11, wherein the oxidizing agent and the reducing agent are the same species.

20. The method of claim 19, wherein the oxidizing agent and the reducing agent is hydrogen peroxide.

* * * * *